(12) United States Patent
Blau et al.

(10) Patent No.: US 8,852,579 B2
(45) Date of Patent: Oct. 7, 2014

(54) METHODS OF INDUCING TISSUE REGENERATION

(75) Inventors: Helen M. Blau, Menlo Park, CA (US); Kostandin Pajcini, Philadelphia, PA (US); Jason Pomerantz, Mill Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/394,798

(22) PCT Filed: Nov. 17, 2010

(86) PCT No.: PCT/US2010/057102
§ 371 (c)(1),
(2), (4) Date: Mar. 14, 2012

(87) PCT Pub. No.: WO2011/063039
PCT Pub. Date: May 26, 2011

(65) Prior Publication Data
US 2012/0171174 A1     Jul. 5, 2012

Related U.S. Application Data

(60) Provisional application No. 61/281,575, filed on Nov. 18, 2009.

(51) Int. Cl.
*A61K 35/12* (2006.01)
*C12Q 1/02* (2006.01)
*C12N 5/00* (2006.01)
*C12N 5/077* (2010.01)

(52) U.S. Cl.
CPC .......... *C12N 5/0658* (2013.01); *C12N 2501/40* (2013.01); *C12N 2501/405* (2013.01)
USPC ............ 424/93.7; 435/325; 435/377; 435/29; 435/375

(58) Field of Classification Search
CPC .................... C12N 2501/405; C12N 2501/40; C12N 5/0658
USPC ................... 424/93.7; 435/29, 325, 377, 375
See application file for complete search history.

(56) References Cited

U.S. PATENT DOCUMENTS

| | | | |
|---|---|---|---|
| 5,324,654 A | 6/1994 | Bredesen | |
| 5,831,067 A | 11/1998 | Strauss et al. | |
| 6,326,201 B1 | 12/2001 | Fung et al. | |
| 2003/0022831 A1 | 1/2003 | Rothbard et al. | |
| 2003/0032593 A1 | 2/2003 | Wender et al. | |
| 2003/0083256 A1 | 5/2003 | Rothbard et al. | |
| 2003/0220334 A1 | 11/2003 | Wender et al. | |
| 2004/0087016 A1* | 5/2004 | Keating et al. | 435/366 |
| 2008/0014182 A1* | 1/2008 | Efrat | 424/93.7 |
| 2008/0187917 A1 | 8/2008 | Morrison et al. | |
| 2008/0227738 A1 | 9/2008 | Keating et al. | |
| 2009/0142841 A1 | 6/2009 | Occhiodoro et al. | |
| 2009/0258423 A1 | 10/2009 | Dugas et al. | |
| 2009/0305987 A1 | 12/2009 | Thayer et al. | |
| 2010/0278789 A1 | 11/2010 | Efrat et al. | |
| 2010/0330049 A1 | 12/2010 | Bouwens et al. | |
| 2012/0295854 A1 | 11/2012 | Blau et al. | |
| 2013/0052267 A1 | 2/2013 | Blau et al. | |

FOREIGN PATENT DOCUMENTS

| WO | WO 2010/108126 A2 | 9/2010 |
|---|---|---|
| WO | WO 2010/108126 A3 | 2/2011 |

OTHER PUBLICATIONS

Leduc et al. p14ARF promotes RB accumulation through inhibition of its Tip60-dependent acetylation. Oncogene (2006) 25, 4147-4154.*
Ohtani et al. The p16INK4a-RB pathway : molecular link between cellular senescence and tumor suppression. J. Med. Invest. 51 : 146-153, Aug. 2004.*
Blais; et al., "Retinoblastoma tumor suppressor protein-dependent methylation of histone H3 lysine 27 is associated with irreversible cell cycle exit", J. Cell Biol. (2007), 179:1399-1412.
Camarda; et al., "pRb-independent mechanism preserves the postmitotic state in terminally differentiated skeletal muscle cells", J. Cell Biology (2004), 167(3):417-423.
Chang; et al., "ARF promotes accumulation of retinoblastoma protein through inhibition of MDMS", Oncogene (2007), 26(32):4627-4634.
Gu; et al., "Interaction of myogenic factors and the retinoblastoma protein mediates muscle cell commitment and differentiation", Cell (1993), 72:309-324.
Levi; et al., "Stem cells use distinct self-renewal programs at different ages", Cold Spring Harb. Symp. Quant. Biol. (2008), 73:539-553.
Pajcini; et al., "Transient Inactivation of Rb and ARF Yields Regenerative Cells from Postmitotic Mammalian Muscle". Cell Stem Cell (2010), 7(2):198-213.
Puri; et al., "Class I histone deacetylases sequentially interact with MyoD and pRb during skeletal myogenesis", Mol. Cell (2001), 8:885-897.
Sharpless; et al., "The INK4A/ARF locus and its two gene products", Curr. Opin. Genet. Dev. (1999), 9:22-30.
Sharpless; et al., "How stem cells age and why this makes us grow old", Nat. Rev. Mol. Cell Biol. (2007), 8:703-713.

(Continued)

*Primary Examiner* — Taeyoon Kim
(74) *Attorney, Agent, or Firm* — Bozicevic, Field & Francis LLP; Pamela J. Sherwood

(57) ABSTRACT

Methods are provided for producing cells within a lineage (lineage restricted cells) from post-mitotic differentiated cells of the same lineage ex vivo and in vivo, and for treating a subject in need of tissue regeneration therapy by employing these lineage-restricted cells. In addition, the production of lineage restricted cells from postmitotic tissues derived from patients with diseases allows for a characterization of pathways that have gone awry in these diseases and for screening of drugs that will ameliorate or correct the defects as a means of novel drug discovery. Also provided are kits for performing these methods.

15 Claims, 22 Drawing Sheets

(56) References Cited

OTHER PUBLICATIONS

Sherr; et al., "p53-Dependent and -independent functions of the Arf tumor suppressor", Cold Spring Harb. Symp. Quant. Biol. (2005), 70:129-137.
Tanaka; et al., "Newt Myotubes Reenter the Cell Cycle by Phosphorylation of the Retinoblastoma Protein", J. Cell Biol. (1997), 136(1):155-165.
Zacksenhaus; et al., "pRb controls proliferation, differentiation, and death of skeletal muscle cells and other lineages during embryogenesis", Genes Dev. (1996), 10:3051-3064.
"International Search Report and Written Opinion of the International Searching Authority", International Searching Authority, Jan. 14, 2011, PCT/US10/57102.
Voorhoeve; et al. "The tumor-suppressive functions of the human INK4A locus", Cancer Cell (Oct. 2003), 4(4):311-319.
Blau, et al. Re"evolutionary" regenerative medicine. JAMA. 2011; 305:87-88.
Burns, et al. Diabetes mellitus: a potential target for stem cell therapy. Curr Stem Cell Res Ther. May 2006;1(2):255-66.
Danos, et al. Safe and efficient generation of recombinant retroviruses with amphotropic and ecotropic host ranges. Proc Natl Acad Sci U S A. Sep. 1988;85(17):6460-4.
Degregori, et al. Distinct roles for E2F proteins in cell growth control and apoptosis. Proc Natl Acad Sci U S A. Jul. 8, 1997;94(14):7245-50.
Doyonnas, et al. Hematopoietic contribution to skeletal muscle regeneration by myelomonocytic precursors. PNAS. 2004; 101(37):13507-13512.
Duckmanton, et al. A single-cell analysis of myogenic dedifferentiation induced by small molecules. Chem Biol. Oct. 2005;12(10):1117-26.
Dugas, et al. Functional genomic analysis of oligodendrocyte differentiation. J Neurosci. Oct. 25, 2006;26(43):10967-83.
Futaki, et al. Structural variety of membrane permeable peptides. Curr Protein Pept Sci. Apr. 2003;4(2):87-96.
Graham, et al. Isolation, culture, and characterization of human intestinal smooth muscle cells. Methods Mol Med. 2003;78:417-23.
Ieda, et al. Direct reprogramming of fibroblasts into functioning cardiomyocytes by defined factors. Cell. 2010; 142:375-386.
Lowe, et al. Tumor suppression by Ink4a-Arf: progress and puzzles. Curr Opin Genet Dev. Feb. 2003;13(1):77-83.
Miller, et al. Generation of helper-free amphotropic retroviruses that transduce a dominant-acting, methotrexate-resistant dihydrofolate reductase gene. Mol Cell Biol. Mar. 1985;5(3):431-7.
Miller, et al. Redesign of retrovirus packaging cell lines to avoid recombination leading to helper virus production. Mol Cell Biol. Aug. 1986;6(8):2895-902.
Mitcheson, et al. Cultured adult cardiac myocytes: future applications, culture methods, morphological and electrophysiological properties. Cardiovasc Res. Aug. 1998;39(2):280-300.
Pajcini, et al. Myoblasts and macrophages share molecular components that contribute to cell-cell fusion. J Cell Biol. Mar. 10, 2008;180(5):1005-19.
Pear, et al. Production of high-titer helper-free retroviruses by transient transfection. Proc Natl Acad Sci U S A. Sep. 15, 1993;90(18):8392-6.
Pomerantz, et al. Reprogramming to a muscle fate by fusion recapitulates differentiation. Journal of Cell Science. 2009; 122(7):1045-1053.
Rando, et al. Primary mouse myoblast purification, characterization, and transplantation for cell-mediated gene therapy. J Cell Biol. Jun. 1994;125(6):1275-87.
Rosania, et al. Myoseverin, a microtubule-binding molecule with novel cellular effects. Nat Biotechnol. Mar. 2000;18(3):304-8.
Rosenblatt, et al. Culturing satellite cells from living single muscle fiber explants. In Vitro Cell Dev Biol Anim. Nov. 1995;31(10):773-9.
Sage, et al. Targeted disruption of the three Rb-related genes leads to loss of G(1) control and immortalization. Genes Dev. Dec. 1, 2000;14(23):3037-50.
Schneider, et al. Reversal of terminal differentiation mediated by p107 in Rb-/-muscle cells. Science. Jun. 3, 1994;264(5164):1467-71.
Siow, et al. Vascular smooth muscle cells : isolation, culture, and characterization. Methods Mol Med. 2001;46:237-45.
Springer, et al. Not the usual suspects: the unexpected sources of tissue regeneration. The Journal of Clinical Investigation. 2001; 107(11):1355-1356.
Ventura, et al. of p53 function leads to tumour regression in vivo. Nature. Feb. 8, 2007;445(7128):661-5. Epub Jan. 24, 2007.
Viatour, et al. Hematopoietic stem cell quiescence is maintained by compound contributions of the retinoblastoma gene family. Cell Stem Cell. Oct. 9, 2008;3(4):416-28.
Vierbuchen, et al. Direct conversion of fibroblasts to functional neurons by defined factors. Nature. 2010; 463:1035-1042.
Wender, et al. The design, synthesis, and evaluation of molecules that enable or enhance cellular uptake: peptoid molecular transporters. Proc Natl Acad Sci U S A. Nov. 21, 2000;97(24):13003-8.
Office action dated Oct. 17, 2012 for U.S. Appl. No. 13/492,679.

* cited by examiner

SEQUENCE LISTING

```
<160> NUMBER OF SEQ ID NOS: 36

<210> SEQ ID NO 1
<211> LENGTH: 4772
<212> TYPE: DNA
<213> ORGANISM: homo sapiens

<400> SEQUENCE: 1
gctcagttgc cgggcggggg agggcgcgtc cggttttct caggggacgt tgaaattatt      60
tttgtaacgg gagtcgggag aggacggggc gtgcccgac gtgcgcgcgc gtcgtcctcc     120
ccggcgctcc tccacagctc gctggctccc gccgcggaaa ggcgtcatgc cgcccaaaac     180
cccccgaaaa acggccgcca ccgccgccgc tgccgccgcg gaaccccgg caccgccgcc     240 gccgccccct cctgaggagg acccagagca ggacagcggc ccggaggacc tgcctctcgt     300
caggcttgag tttgaagaaa cagaagaacc tgatttact gcattatgtc agaaattaaa     360
gataccagat catgtcagag agagagcttg gttaacttgg gagaaagttt catctgtgga     420
tggagtattg ggaggttata ttcaaaagaa aaaggaactg tggggaatct gtatctttat     480
tgcagcagtt gacctagatg agatgtcgtt cacttttact gagctacaga aaaacataga     540
```

```
aatcagtgtc cataaattct ttaacttact aaaagaaatt gataccagta ccaaagttga    600
taatgctatg tcaagactgt tgaagaagta tgatgtattg tttgcactct tcagcaaatt    660
ggaaaggaca tgtgaactta tatatttgac acaacccagc agttcgatat ctactgaaat    720
aaattctgca ttggtgctaa aagtttcttg gatcacattt ttattagcta aaggggaagt    780
attacaaatg gaagatgatc tggtgatttc atttcagtta atgctatgtg tccttgacta    840
ttttattaaa ctctcacctc ccatgttgct caaagaacca tataaaacag ctgttatacc    900
cattaatggt tcacctcgaa cacccaggcg aggtcagaac aggagtgcac ggatagcaaa    960
acaactagaa aatgatacaa gaattattga agttctctgt aaagaacatg aatgtaatat   1020
agatgaggtg aaaaatgttt atttcaaaaa ttttatacct tttatgaatt ctcttggact   1080
tgtaacatct aatggacttc cagaggttga aaatctttct aaacgatacg aagaaattta   1140
tcttaaaaat aaagatctag atgcaagatt attttttggat catgataaaa ctcttcagac   1200
tgattctata gacagttttg aaacacagag aacaccacga aaaagtaacc ttgatgaaga   1260
ggtgaatgta attcctccac acactccagt taggactgtt atgaacacta ccaacaatt    1320 aatgatgatt ttaaattcag caagtgatca accttcagaa atctgatttt cctattttaa   1380
caactgcaca gtgaatccaa agaaagtat actgaaaaga gtgaaggata taggatacat    1440
ctttaaagag aaatttgcta aagctgtggg acagggttgt gtcgaaattg gatcacagcg   1500
atacaaactt ggagttcgct tgtattaccg agtaatggaa tccatgctta aatcagaaga   1560
agaacgatta tccattcaaa atttagcaa acttctgaat gacaacattt ttcatatgtc    1620
tttattggcg tgcgctcttg aggttgtaat ggccacatat agcagaagta catctcagaa   1680
tcttgattct ggaacagatt tgtctttccc atggattctg aatgtgctta atttaaaagc   1740
ctttgatttt tacaaagtga tcgaaagttt tatcaaagca gaaggcaact tgacaagaga   1800
aatgataaaa catttagaac gatgtgaaca tcgaatcatg gaatcccttg catggctctc   1860
agattcacct ttatttgatc ttattaaaca atcaaaggac cgagaaggac caactgatca   1920
ccttgaatct gcttgtcctc ttaatcttcc tctccagaat aatcacactg cagcagatat   1980
gtatctttct cctgtaagat ctccaaagaa aaaaggttca actacgcgtg taaattctac   2040
tgcaaatgca gagacacaag caacctcagc cttccagacc cagaagccat gaaatctac    2100 ctctctttca ctgttttata aaaagtgta tcggctagcc tatctccggc taaatacact    2160
ttgtgaacgc cttctgtctg agcacccaga attagaacat atcatctgga cccttttcca   2220
gcacaccctg cagaatgagt atgaactcat gagagacagg catttggacc aaattatgat   2280
gtgttccatg tatggcatat gcaaagtgaa gaatatagac cttaaattca aaatcattgt   2340
aacagcatac aaggatcttc ctcatgctgt tcaggagaca ttcaaacgtg ttttgatcaa   2400
agaagaggag tatgattcta ttatagtatt ctataactcg gtcttcatgc agagactgaa   2460
aacaaatatt ttgcagtatg cttccaccag gcccectacc ttgtcaccaa tacctcacat   2520
tcctcgaagc ccttacaagt ttcctagttc acccttacgg attcctggag ggaacatcta   2580 tatttcacccc ctgaagagtc catataaaat ttcagaaggt ctgccaacac caacaaaaat   2640
gactccaaga tcaagaatct tagtatcaat tggtgaatca ttcgggactt ctgagaagtt   2700
ccagaaaata aatcagatgg tatgtaacag cgaccgtgtg ctcaaaagaa gtgctgaagg   2760 aagcaacccct cctaaaccac tgaaaaaact acgctttgat attgaaggat cagatgaagc   2820
agatggaagt aaacatctcc caggagagtc caaatttcag cagaaactgg cagaaatgac   2880
```

```
ttctactcga acacgaatgc aaaagcagaa aatgaatgat agcatggata cctcaaacaa    2940
ggaagagaaa tgaggatctc aggaccttgg tggacactgt gtacacctct ggattcattg    3000
tctctcacag atgtgactgt ataactttcc caggttctgt ttatggccac atttaatatc    3060
ttcagctctt tttgtggata taaaatgtgc agatgcaatt gtttgggtga ttcctaagcc    3120
acttgaaatg ttagtcattg ttatttatac aagattgaaa atcttgtgta aatcctgcca    3180
tttaaaaagt tgtagcagat tgtttcctct tccaaagtaa aattgctgtg ctttatggat    3240
agtaagaatg gccctagagt gggagtcctg ataacccagg cctgtctgac tactttgcct    3300
tcttttgtag catataggtg atgtttgctc ttgtttttat taatttatat gtatattttt    3360
ttaatttaac atgaacaccc ttagaaaatg tgtcctatct atcttccaaa tgcaatttga    3420
ttgactgccc attcaccaaa attatcctga actcttctgc aaaaatggat attattagaa    3480
attagaaaaa aattactaat tttacacatt agatttttatt ttactattgg aatctgatat    3540
actgtgtgct tgtttttataa aattttgctt ttaattaaat aaaagctgga agcaaagtat    3600
aaccatatga tactatcata ctactgaaac agatttcata cctcagaatg taaaagaact    3660
tactgattat tttcttcatc caacttatgt ttttaaatga ggattattga tagtactctt    3720
ggttttttata ccattcagat cactgaattt ataaagtacc catctagtac ttgaaaaagt    3780
aaagtgttct gccagatctt aggtatagag gaccctaaca cagtatatcc caagtgcact    3840
ttctaatgtt tctgggtcct gaagaattaa gatacaaatt aattttactc cataaacaga    3900
ctgttaatta taggagcctt aatttttttt tcatagagat ttgtctaatt gcatctcaaa    3960
attattctgc cctccttaat ttgggaaggt ttgtgttttc tctggaatgg tacatgtctt    4020
ccatgtatct tttgaactgg caattgtcta tttatctttt attttttttaa gtcagtatgg    4080
tctaacactg gcatgttcaa agccacatta tttctagtcc aaaattacaa gtaatcaagg    4140
gtcattatgg gttaggcatt aatgtttcta tctgattttg tgcaaaagct tcaaattaaa    4200
acagctgcat tagaaaaaga ggcgcttctc ccctccccta cacctaaagg tgtatttaaa    4260
ctatcttgtg tgattaactt atttagagat gctgtaactt aaaatagggg atatttaagg    4320
tagcttcagc tagcttttag gaaaatcact ttgtctaact cagaattatt tttaaaaaga    4380
aatctggtct tgttagaaaa caaaatttta ttttgtgctc atttaagttt caaacttact    4440
attttgacag ttattttgat aacaatgaca ctagaaaact tgactccatt tcatcattgt    4500
ttctgcatga atatcataca aatcagttag ttttttaggtc aagggcttac tatttctggg    4560
tcttttgcta ctaagttcac attagaatta gtgccagaat tttaggaact tcagagatcg    4620
tgtattgaga tttcttaaat aatgcttcag atattattgc tttattgctt ttttgtattg    4680
gttaaaactg tacatttaaa attgctatgt tactattttc tacaattaat agtttgtcta    4740
ttttaaaata aattagttgt taagagtctt aa                                  4772
```

<210> SEQ ID NO 2
<211> LENGTH: 928
<212> TYPE: PRT
<213> ORGANISM: homo sapiens

<400> SEQUENCE: 2

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
        20                  25                  30

Pro Glu Gln Asp Ser Gly Pro Glu Asp Leu Pro Leu Val Arg Leu Glu

```
                35              40              45
Phe Glu Glu Thr Glu Glu Pro Asp Phe Thr Ala Leu Cys Gln Lys Leu
 50                  55                  60

Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys Lys
                 85                  90                  95

Glu Leu Trp Gly Ile Cys Ile Phe Ile Ala Ala Val Asp Leu Asp Glu
                100                 105                 110

Met Ser Phe Thr Phe Thr Glu Leu Gln Lys Asn Ile Glu Ile Ser Val
                115                 120                 125

His Lys Phe Phe Asn Leu Leu Lys Glu Ile Asp Thr Ser Thr Lys Val
                130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
                180                 185                 190

Val Ser Trp Ile Thr Phe Leu Leu Ala Lys Gly Glu Val Leu Gln Met
                195                 200                 205

Glu Asp Asp Leu Val Ile Ser Phe Gln Leu Met Leu Cys Val Leu Asp
210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
                260                 265                 270

Ile Ile Glu Val Leu Cys Lys Glu His Glu Cys Asn Ile Asp Glu Val
                275                 280                 285

Lys Asn Val Tyr Phe Lys Asn Phe Ile Pro Phe Met Asn Ser Leu Gly
                290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
                340                 345                 350

Thr Gln Arg Thr Pro Arg Lys Ser Asn Leu Asp Glu Glu Val Asn Val
                355                 360                 365

Ile Pro Pro His Thr Pro Val Arg Thr Val Met Asn Thr Ile Gln Gln
                370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
                435                 440                 445

Gly Val Arg Leu Tyr Tyr Arg Val Met Glu Ser Met Leu Lys Ser Glu
                450                 455                 460
```

-continued

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

-continued

```
Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
        900                 905                 910

Lys Gln Lys Met Asn Asp Ser Met Asp Thr Ser Asn Lys Glu Glu Lys
    915                 920                 925

<210> SEQ ID NO 3
<211> LENGTH: 4270
<212> TYPE: DNA
<213> ORGANISM: homo sapiens

<400> SEQUENCE: 3
gcaggtggtt gtgggtagcg cgcctgggag ggagaaagaa gtcgggggcc gtggcgcgca        60
gcccgcgggg cctgaaggga tgttcgagga caagccccac gctgaggggg cggcggtggt       120
cgccgcagcc ggggaggcgc tacaggccct gtgccaggag ctgaacctgg acgaggggag       180
cgcggccgaa gccctggacg acttactgc catccgaggc aactacagcc tagagggaga       240
agttacacac tggttggcat gttcattata tgttgcatgc cgcaaaagca ttattcccac       300
ggttggaaag ggtatcatgg aaggcaactg tgtttcactt accagaatac tacgttcagc       360
taaattaagt ttaatacaat ttttagtaa atgaagaaa tggatggaca tgtcaaatct       420
accacaagaa tttcgtgaac gtatagaaag gctagagaga aattttgagg tgtctactgt       480
aatattcaaa aaatatgagc caattttttt agatatattt caaaatccat atgaagaacc       540
accaaagtta ccacgaagcc ggaagcgag gaggattcct tgcagtgtta aggatctgtt       600 taattctgt tggacacttt tgtttatac taagggtaat tttcggatga ttggggatga       660
cttagtaaac tcttatcatt tacttctatg ctgcttggat ctgatttttg ccaatgcgat       720
tatgtgccca aatagacaag acttgctaaa tccatcattt aaaggtttac catctgattt       780
tcatactgct gactttacgg cttctgaaga gccaccctgc atcattgctg tactgtgtga       840
actgcatgat ggacttctcg tagaagcaaa aggaataaag gagcactact ttaagccata       900
tatttcaaaa ctcttttgaca ggaagatatt aaaaggagaa tgcctcctgg accttttcaag      960 ttttactgat aatagcaaag cagtgaataa ggagtatgaa gagtatgttc taactgttgg       1020
tgattttgat gagaggatct ttttgggagc agacgcagaa gaggaaattg gaacacctcg       1080
aaagttcact cgtgacaccc cattaggaa actgacagca caggctaatg tggagtataa       1140
ccttcaacag cactttgaaa aaaaaggtc atttgcacct tctaccccac tgaccggacg       1200
gagatattta cgagaaaaag aagcagtcat tactcctgtt gcatcagcca cccaaagtgt       1260
gagccggtta cagagtattg tggctggtct gaaaaatgca ccaagtgacc aacttataaa       1320 tattttgaa tcttgtgtgc gtaatcctgt ggaaacatt atgaaatac taaaggaat       1380 aggagagact ttctgtcaac actatactca atcaacagat gaacagccag atctcacat       1440 agactttgct gtaaacagac taaagctggc agaaatttg tattataaaa tactagagac       1500
tgtaatggtt caggaaacac gaagacttca tggaatggac atgtcagttc tttagagca       1560 agatatattt catcgttcct tgatggcttg ttgtttggaa attgtgctct ttgcctatag       1620
ctcacctcgt acttttcctt ggattattga agttctcaac ttgcaaccat tttacttta       1680 taaggttatt gaggtggtga tccgctcaga agagggctc tcaagggaca tggtgaaaca       1740
cctaaacagc attgaagaac agattttgga gagtttagca tggagtcacg attctgcact       1800
gtgggaggct ctccaggttt ctgcaaacaa agttcctacc tgtgaagaag ttatattccc       1860
```

```
aaataacttt gaaacaggaa atggaggaaa tgtgcaggga catcttcccc tgatgccaat    1920
gtctcctcta atgcacccaa gagtcaagga agttcgaact gacagtggga gtcttcgaag    1980
agatatgcaa ccattgtctc caatttctgt ccatgaacgc tacagttctc ctaccgcagg    2040
gagtgctaag agaagactct ttggagagga ccccccaaag gaaatgctta tggacaagat    2100
cataacagaa ggaacaaaat tgaaaatcgc tccttcttca agcattactg ctgaaaatgt    2160 atcaattta cctggtcaaa ctcttctaac aatggccaca gccccagtaa caggaacaac    2220
aggacataaa gttacaattc cattacatgg tgtcgcaaat gatgctggag agatcacact    2280
gatacctctt tccatgaata caaatcagga gtccaaagtc aagagtcctg tatcacttac    2340
tgctcattca ttaattggtg cttctccaaa acagaccaat ctgactaaag cacaagaggt    2400
acattcaact ggaataaaca ggccaaagag aactgggtcc ttagcactat tttacagaaa    2460
ggtctatcat ttggcaagtg tacgcttacg tgatctatgt ctaaaactgg atgtttcaaa    2520
tgagttacga aggaagatat ggacgtgttt tgaattcact ttagttcact gtcctgatct    2580
aatgaaagac aggcatttgg atcagctcct cctttgtgcc ttttatatca tggcaaaggt    2640
aacaaaagaa gaaagaactt ttcaagaaat tatgaaaagt tataggaatc agccccaagc    2700
taatagtcac gtatatagaa gtgttctgct gaaaagtatt ccaagagaag ttgtggcata    2760
taataaaaat ataatgatg actttgaaat gatagattgt gacttagaag atgctacaaa    2820
aacacctgac tgttccagtg gaccagtgaa agaggaaaga ggtgatctta taaaatttta    2880
caatacaata tatgtaggaa gagtgaagtc atttgcactg aaatacgact ggcgaatca    2940 ggaccatatg atggatgctc caccactctc tcctttttcca catattaaac aacagccagg    3000
ctcaccacgc cgcatttccc agcagcactc catttatatt tccccgcaca agaatgggtc    3060
aggccttaca ccaagaagcg ctctgctgta caagttcaat ggcagccctt ctaagagttt    3120
gaaagatatc aacaacatga taaggcaagg tgagcagaga accaagaagc gagtaatagc    3180
catcgatagt gatgcagaat cccctgccaa acgcgtctgt caagaaaatg atgacgtttt    3240
actgaaacga ctacaggatg ttgtcagtga agagcaaat cattaatgtt gttcttgttt    3300
ctatgataaa agcactttca gattgttctg cagaaagttg gagctctgtc cttcaaacct    3360
tttagcccta tagatgataa atatcactgg gttataagaa aaattgcac aaaaattatg    3420 tgcttttaa aatatttatc caaatgtag ttgacagaga tgtatttga gttggattgg    3480 aaaggaatat tttaagtgcc ttttaaaaat actaatagtc cggccaggcg ctgtggctca    3540
cgcctgtaat cccaggactt tgggaggcca aggcgggcag atcaccggag gtcaggagtt    3600
cgagaccagc ctgaccaaca tggagaaacc ccatctctac taaaaataca aaattagccg    3660
ggtgtggtgg cgcatgcctg taatcccagc tacttgggag gctgaggcag aattgcttga    3720
acccaggaag cggaggttgt ggtgagccaa ggttgcgcca ctgcactcca gcctgggcaa    3780
caagagtaaa actccatctc aaaaaatata tatatatata taaatagga attttttta    3840 atgtttgctc cttgagtttt caagatgaaa taaggagaaa cccataact ttttagctct    3900 cttttaaaaa taaatgtctc cttctgtgtt ctgtaatatg aggataaata atctactttt    3960
gatagcatgc tttgagatat ttgtattctt aatttaatat tgaaggaagg ggttggttcc    4020
catagtacct ggccagaggg ttatatacca tcctgtctct ggcccactgt ggtaattcca    4080
catccaggta ccaccgccat tcagagttgt ctcacccctt ctcgtgcctt ttctctcctt    4140
gagctttata aacagatttg tacctgagcc ccagtgctac actcatcctt gctttccagc    4200
cctaagccat ctcagcctga tgtcacaacc caataaatgg ggcactttct tcttttgtaa    4260
```

-continued

```
actattatca                                              4270
```

<210> SEQ ID NO 4
<211> LENGTH: 1068
<212> TYPE: PRT
<213> ORGANISM: homo sapiens

<400> SEQUENCE: 4

| Met | Phe | Glu | Asp | Lys | Pro | His | Ala | Glu | Gly | Ala | Val | Val | Ala | Ala |
|---|---|---|---|---|---|---|---|---|---|---|---|---|---|---|
| 1 | | | | 5 | | | | | 10 | | | | | 15 |

Ala Gly Glu Ala Leu Gln Ala Leu Cys Gln Glu Leu Asn Leu Asp Glu
             20                  25                  30

Gly Ser Ala Ala Glu Ala Leu Asp Asp Phe Thr Ala Ile Arg Gly Asn
         35                  40                  45

Tyr Ser Leu Glu Gly Glu Val Thr His Trp Leu Ala Cys Ser Leu Tyr
 50                  55                  60

Val Ala Cys Arg Lys Ser Ile Ile Pro Thr Val Gly Lys Gly Ile Met
65                  70                  75                  80

Glu Gly Asn Cys Val Ser Leu Thr Arg Ile Leu Arg Ser Ala Lys Leu
                 85                  90                  95

Ser Leu Ile Gln Phe Phe Ser Lys Met Lys Lys Trp Met Asp Met Ser
            100                 105                 110

Asn Leu Pro Gln Glu Phe Arg Glu Arg Ile Glu Arg Leu Glu Arg Asn
        115                 120                 125

Phe Glu Val Ser Thr Val Ile Phe Lys Lys Tyr Glu Pro Ile Phe Leu
    130                 135                 140

Asp Ile Phe Gln Asn Pro Tyr Glu Glu Pro Pro Lys Leu Pro Arg Ser
145                 150                 155                 160

Arg Lys Gln Arg Arg Ile Pro Cys Ser Val Lys Asp Leu Phe Asn Phe
                165                 170                 175

Cys Trp Thr Leu Phe Val Tyr Thr Lys Gly Asn Phe Arg Met Ile Gly
            180                 185                 190

Asp Asp Leu Val Asn Ser Tyr His Leu Leu Leu Cys Cys Leu Asp Leu
        195                 200                 205

Ile Phe Ala Asn Ala Ile Met Cys Pro Asn Arg Gln Asp Leu Leu Asn
    210                 215                 220

Pro Ser Phe Lys Gly Leu Pro Ser Asp Phe His Thr Ala Asp Phe Thr
225                 230                 235                 240

Ala Ser Glu Glu Pro Pro Cys Ile Ile Ala Val Leu Cys Glu Leu His
                245                 250                 255

Asp Gly Leu Leu Val Glu Ala Lys Gly Ile Lys Glu His Tyr Phe Lys
            260                 265                 270

Pro Tyr Ile Ser Lys Leu Phe Asp Arg Lys Ile Leu Lys Gly Glu Cys
        275                 280                 285

Leu Leu Asp Leu Ser Ser Phe Thr Asp Asn Ser Lys Ala Val Asn Lys
    290                 295                 300

Glu Tyr Glu Glu Tyr Val Leu Thr Val Gly Asp Phe Asp Glu Arg Ile
305                 310                 315                 320

Phe Leu Gly Ala Asp Ala Glu Glu Ile Gly Thr Pro Arg Lys Phe
                325                 330                 335

Thr Arg Asp Thr Pro Leu Gly Lys Leu Thr Ala Gln Ala Asn Val Glu
            340                 345                 350

Tyr Asn Leu Gln Gln His Phe Glu Lys Lys Arg Ser Phe Ala Pro Ser
        355                 360                 365

-continued

```
Thr Pro Leu Thr Gly Arg Arg Tyr Leu Arg Glu Lys Glu Ala Val Ile
    370                 375                 380

Thr Pro Val Ala Ser Ala Thr Gln Ser Val Ser Arg Leu Gln Ser Ile
385                 390                 395                 400

Val Ala Gly Leu Lys Asn Ala Pro Ser Asp Gln Leu Ile Asn Ile Phe
                405                 410                 415

Glu Ser Cys Val Arg Asn Pro Val Glu Asn Ile Met Lys Ile Leu Lys
            420                 425                 430

Gly Ile Gly Glu Thr Phe Cys Gln His Tyr Thr Gln Ser Thr Asp Glu
        435                 440                 445

Gln Pro Gly Ser His Ile Asp Phe Ala Val Asn Arg Leu Lys Leu Ala
    450                 455                 460

Glu Ile Leu Tyr Tyr Lys Ile Leu Glu Thr Val Met Val Gln Glu Thr
465                 470                 475                 480

Arg Arg Leu His Gly Met Asp Met Ser Val Leu Leu Glu Gln Asp Ile
                485                 490                 495

Phe His Arg Ser Leu Met Ala Cys Cys Leu Glu Ile Val Leu Phe Ala
            500                 505                 510

Tyr Ser Ser Pro Arg Thr Phe Pro Trp Ile Ile Glu Val Leu Asn Leu
        515                 520                 525

Gln Pro Phe Tyr Phe Tyr Lys Val Ile Glu Val Ile Arg Ser Glu
    530                 535                 540

Glu Gly Leu Ser Arg Asp Met Val Lys His Leu Asn Ser Ile Glu Glu
545                 550                 555                 560

Gln Ile Leu Glu Ser Leu Ala Trp Ser His Asp Ser Ala Leu Trp Glu
                565                 570                 575

Ala Leu Gln Val Ser Ala Asn Lys Val Pro Thr Cys Glu Glu Val Ile
            580                 585                 590

Phe Pro Asn Asn Phe Glu Thr Gly Asn Gly Asn Val Gln Gly His
        595                 600                 605

Leu Pro Leu Met Pro Met Ser Pro Leu Met His Pro Arg Val Lys Glu
    610                 615                 620

Val Arg Thr Asp Ser Gly Ser Leu Arg Arg Asp Met Gln Pro Leu Ser
625                 630                 635                 640

Pro Ile Ser Val His Glu Arg Tyr Ser Ser Pro Thr Ala Gly Ser Ala
                645                 650                 655

Lys Arg Arg Leu Phe Gly Glu Asp Pro Pro Lys Glu Met Leu Met Asp
            660                 665                 670

Lys Ile Ile Thr Glu Gly Thr Lys Leu Lys Ile Ala Pro Ser Ser Ser
        675                 680                 685

Ile Thr Ala Glu Asn Val Ser Ile Leu Pro Gly Gln Thr Leu Leu Thr
    690                 695                 700

Met Ala Thr Ala Pro Val Thr Gly Thr Thr Gly His Lys Val Thr Ile
705                 710                 715                 720

Pro Leu His Gly Val Ala Asn Asp Ala Gly Glu Ile Thr Leu Ile Pro
                725                 730                 735

Leu Ser Met Asn Thr Asn Gln Glu Ser Lys Val Lys Ser Pro Val Ser
            740                 745                 750

Leu Thr Ala His Ser Leu Ile Gly Ala Ser Pro Lys Gln Thr Asn Leu
        755                 760                 765

Thr Lys Ala Gln Glu Val His Ser Thr Gly Ile Asn Arg Pro Lys Arg
    770                 775                 780
```

```
Thr Gly Ser Leu Ala Leu Phe Tyr Arg Lys Val Tyr His Leu Ala Ser
785                 790                 795                 800

Val Arg Leu Arg Asp Leu Cys Leu Lys Leu Asp Val Ser Asn Glu Leu
                805                 810                 815

Arg Arg Lys Ile Trp Thr Cys Phe Glu Phe Thr Leu Val His Cys Pro
            820                 825                 830

Asp Leu Met Lys Asp Arg His Leu Asp Gln Leu Leu Leu Cys Ala Phe
            835                 840                 845

Tyr Ile Met Ala Lys Val Thr Lys Glu Glu Arg Thr Phe Gln Glu Ile
        850                 855                 860

Met Lys Ser Tyr Arg Asn Gln Pro Gln Ala Asn Ser His Val Tyr Arg
865                 870                 875                 880

Ser Val Leu Leu Lys Ser Ile Pro Arg Glu Val Val Ala Tyr Asn Lys
                885                 890                 895

Asn Ile Asn Asp Asp Phe Glu Met Ile Asp Cys Asp Leu Glu Asp Ala
                900                 905                 910

Thr Lys Thr Pro Asp Cys Ser Ser Gly Pro Val Lys Glu Glu Arg Gly
            915                 920                 925

Asp Leu Ile Lys Phe Tyr Asn Thr Ile Tyr Val Gly Arg Val Lys Ser
            930                 935                 940

Phe Ala Leu Lys Tyr Asp Leu Ala Asn Gln Asp His Met Met Asp Ala
945                 950                 955                 960

Pro Pro Leu Ser Pro Phe Pro His Ile Lys Gln Gln Pro Gly Ser Pro
                965                 970                 975

Arg Arg Ile Ser Gln Gln His Ser Ile Tyr Ile Ser Pro His Lys Asn
                980                 985                 990

Gly Ser Gly Leu Thr Pro Arg Ser Ala Leu Leu Tyr Lys Phe Asn Gly
                995                 1000                1005

Ser Pro Ser Lys Ser Leu Lys Asp Ile Asn Asn Met Ile Arg Gln Gly
        1010                1015                1020

Glu Gln Arg Thr Lys Lys Arg Val Ile Ala Ile Asp Ser Asp Ala Glu
1025                1030                1035                1040

Ser Pro Ala Lys Arg Val Cys Gln Glu Asn Asp Asp Val Leu Leu Lys
                1045                1050                1055

Arg Leu Gln Asp Val Val Ser Glu Arg Ala Asn His
                1060                1065

<210> SEQ ID NO 5
<211> LENGTH: 3371
<212> TYPE: DNA
<213> ORGANISM: homo sapiens

<400> SEQUENCE: 5
gcaggtggtt gtgggtagcg cgcctgggag ggagaaagaa gtcgggggcc gtggcgcgca      60
gcccgcgggg cctgaaggga tgttcgagga caagccccac gctgaggggg cggcggtggt     120
cgccgcagcc ggggaggcgc tacaggccct gtgccaggag ctgaacctgg acaggggag      180 cgcggccgaa gccctggacg actttactgc catccgaggc aactacagcc tagagggaga     240
agttacacac tggttggcat gttcattata tgttgcatgc cgcaaaagca ttattcccac     300
ggttggaaag ggtatcatgg aaggcaactg tgtttcactt accagaatac tacgttcagc     360
taaattaagt ttaatacaat ttttagtaa aatgaagaaa tggatggaca tgtcaaatct      420
accacaagaa tttcgtgaac gtatagaaag gctagagaga aattttgagg tgtctactgt     480
aatattcaaa aaatatgagc caattttttt agatatattt caaaatccat atgaagaacc     540
```

```
accaaagtta ccacgaagcc ggaagcagag gaggattcct tgcagtgtta aggatctgtt    600
taatttctgt tggacacttt ttgtttatac taagggtaat tttcggatga ttggggatga    660
cttagtaaac tcttatcatt tacttctatg ctgcttggat ctgattttg ccaatgcgat     720 tatgtgccca aatagacaag acttgctaaa tccatcattt aaaggtttac catctgattt    780
tcatactgct gactttacgg cttctgaaga gccaccctgc atcattgctg tactgtgtga    840
actgcatgat ggacttctcg tagaagcaaa aggaataaag gagcactact ttaagccata    900
tatttcaaaa ctcttttgaca ggaagatatt aaaaggagaa tgcctcctgg acctttcaag   960
ttttactgat aatagcaaag cagtgaataa ggagtatgaa gagtatgttc taactgttgg   1020
tgattttgat gagaggatct ttttgggagc agacgcagaa gaggaaattg gaacacctcg   1080
aaagttcact cgtgacaccc cattaggaa actgacagca caggctaatg tggagtataa    1140
ccttcaacag cactttgaaa aaaaaggtc atttgcacct tctaccccac tgaccggacg    1200
gagatattta cgagaaaaag aagcagtcat tactcctgtt gcatcagcca cccaaagtgt   1260
gagccggtta cagagtattg tggctggtct gaaaaatgca ccaagtgacc aacttataaa   1320 tattttgaa tcttgtgtgc gtaatcctgt ggaaaacatt atgaaaatac taaaaggaat    1380
aggagagact ttctgtcaac actatactca atcaacagat gaacagccag atctcacat    1440 agactttgct gtaaacagac taagctggc agaaattttg tattataaaa tactagagac    1500
tgtaatggtt caggaaacac gaagacttca tggaatggac atgtcagttc ttttagagca   1560
agatatattt catcgttcct tgatggcttg ttgtttggaa attgtgctct ttgcctatag   1620
ctcacctcgt acttttcctt ggattattga agttctcaac ttgcaaccat tttactttta   1680
taaggttatt gaggtggtga tccgctcaga gaggggctc tcaagggaca tggtgaaaca    1740
cctaaacagc attgaagaac agattttgga gagtttagca tggagtcacg attctgcact   1800
gtgggaggct ctccaggttt ctgcaaacaa agttcctacc tgtgaagaag ttatattccc   1860
aaataacttt gaaacaggaa atggaggaaa tgtgcaggga catcttcccc tgatgccaat   1920
gtctcctcta atgcacccaa gagtcaagga agttcgaact gacagtggga gtcttcgaag   1980
agatatgcaa ccattgtctc caatttctgt ccatgaacgc tacagttctc ctaccgcagg   2040
gagtgctaag agaagactct ttggagagga ccccccaaag gaaatgctta tggacaagat   2100
cataacagaa ggaacaaaat tgaaaatcgc tccttcttca agcattactg ctgaaaatgt   2160 atcaattta cctggtcaaa ctcttctaac aatggccaca gccccagtaa caggaacaac   2220
aggacataaa gttacaattc cattacatgg tgtcgcaaat gatgctggag agatcacact   2280
gatacctctt tccatgaata caaatcagga gtccaaagtc aagagtcctg tatcacttac   2340
tgctcattca ttaattggtg cttctccaaa acagaccaat ctgactaaag cacaagaggt   2400
acattcaact ggaataaaca ggccaaagag aactgggtcc ttagcactat tttacagaaa   2460
ggtctatcat ttggcaagtg tacgcttacg tgatctatgt ctaaaactgg atgtttcaaa   2520
tgagttacga aggaagatat ggacgtgttt tgaattcact ttagttcact gtcctgatct   2580
aatgaaagac aggcatttgg atcagctcct cctttgtgcc ttttatatca tggcaaaggt   2640
aacaaaagaa gaaagaactt tcaagaaat tatgaaaagt tataggaatc agccccaagc   2700
taatagtcac gtatatagaa gtgttctgct gaaaagtatt ccaagagaag ttgtggcata   2760
taataaaaat ataaatgatg actttgaaat gatagattgt gacttagaag atgctacaaa   2820
aacacctgac tgttccagtg gaccagtgaa agaggaaaga ggtgatctta taaaattta    2880
```

-continued

```
caatacaata tatgtaggaa gagtgaagtc atttgcactg aaatacgact tggcgaatca    2940
ggaccatatg atggatgctc caccactctc tccttttcca catattaaac aacagccagg    3000
ctcaccacgc cgcatttccc agcagcactc catttatatt tccccgcaca agaatgggtc    3060
aggccttaca ccaagaagcg ctctgctgta caagttcaat ggcagccctt ctaaggtaag    3120
gtgaataggc taaaagttgg atttcagatt aacagtcagt aactgttaat cctgcctctt    3180
tttttttttt tcttttttgg ccaagttact actatactaa taaaatatga aatgttaact    3240
atgaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa a                                                         3371

<210> SEQ ID NO 6
<211> LENGTH: 1014
<212> TYPE: PRT
<213> ORGANISM: homo sapiens

<400> SEQUENCE: 6

Met Phe Glu Asp Lys Pro His Ala Glu Gly Ala Ala Val Val Ala Ala
 1               5                  10                  15

Ala Gly Glu Ala Leu Gln Ala Leu Cys Gln Glu Leu Asn Leu Asp Glu
                20                  25                  30

Gly Ser Ala Ala Glu Ala Leu Asp Asp Phe Thr Ala Ile Arg Gly Asn
            35                  40                  45

Tyr Ser Leu Glu Gly Glu Val Thr His Trp Leu Ala Cys Ser Leu Tyr
        50                  55                  60

Val Ala Cys Arg Lys Ser Ile Ile Pro Thr Val Gly Lys Gly Ile Met
    65                  70                  75                  80

Glu Gly Asn Cys Val Ser Leu Thr Arg Ile Leu Arg Ser Ala Lys Leu
                85                  90                  95

Ser Leu Ile Gln Phe Phe Ser Lys Met Lys Lys Trp Met Asp Met Ser
               100                 105                 110

Asn Leu Pro Gln Glu Phe Arg Glu Arg Ile Glu Arg Leu Glu Arg Asn
           115                 120                 125

Phe Glu Val Ser Thr Val Ile Phe Lys Lys Tyr Glu Pro Ile Phe Leu
       130                 135                 140

Asp Ile Phe Gln Asn Pro Tyr Glu Glu Pro Pro Lys Leu Pro Arg Ser
145                 150                 155                 160

Arg Lys Gln Arg Arg Ile Pro Cys Ser Val Lys Asp Leu Phe Asn Phe
               165                 170                 175

Cys Trp Thr Leu Phe Val Tyr Thr Lys Gly Asn Phe Arg Met Ile Gly
           180                 185                 190

Asp Asp Leu Val Asn Ser Tyr His Leu Leu Cys Cys Leu Asp Leu
       195                 200                 205

Ile Phe Ala Asn Ala Ile Met Cys Pro Asn Arg Gln Asp Leu Leu Asn
   210                 215                 220

Pro Ser Phe Lys Gly Leu Pro Ser Asp Phe His Thr Ala Asp Phe Thr
225                 230                 235                 240

Ala Ser Glu Glu Pro Pro Cys Ile Ile Ala Val Leu Cys Glu Leu His
               245                 250                 255

Asp Gly Leu Leu Val Glu Ala Lys Gly Ile Lys Glu His Tyr Phe Lys
           260                 265                 270

Pro Tyr Ile Ser Lys Leu Phe Asp Arg Lys Ile Leu Lys Gly Glu Cys
       275                 280                 285
```

-continued

```
Leu Leu Asp Leu Ser Ser Phe Thr Asp Asn Ser Lys Ala Val Asn Lys
        290                 295                 300

Glu Tyr Glu Glu Tyr Val Leu Thr Val Gly Asp Phe Asp Glu Arg Ile
305                 310                 315                 320

Phe Leu Gly Ala Asp Ala Glu Glu Ile Gly Thr Pro Arg Lys Phe
                325                 330                 335

Thr Arg Asp Thr Pro Leu Gly Lys Leu Thr Ala Gln Ala Asn Val Glu
            340                 345                 350

Tyr Asn Leu Gln Gln His Phe Glu Lys Lys Arg Ser Phe Ala Pro Ser
        355                 360                 365

Thr Pro Leu Thr Gly Arg Arg Tyr Leu Arg Glu Lys Glu Ala Val Ile
370                 375                 380

Thr Pro Val Ala Ser Ala Thr Gln Ser Val Ser Arg Leu Gln Ser Ile
385                 390                 395                 400

Val Ala Gly Leu Lys Asn Ala Pro Ser Asp Gln Leu Ile Asn Ile Phe
                405                 410                 415

Glu Ser Cys Val Arg Asn Pro Val Glu Asn Ile Met Lys Ile Leu Lys
                420                 425                 430

Gly Ile Gly Glu Thr Phe Cys Gln His Tyr Thr Gln Ser Thr Asp Glu
            435                 440                 445

Gln Pro Gly Ser His Ile Asp Phe Ala Val Asn Arg Leu Lys Leu Ala
450                 455                 460

Glu Ile Leu Tyr Tyr Lys Ile Leu Glu Thr Val Met Val Gln Glu Thr
465                 470                 475                 480

Arg Arg Leu His Gly Met Asp Met Ser Val Leu Leu Glu Gln Asp Ile
                485                 490                 495

Phe His Arg Ser Leu Met Ala Cys Cys Leu Glu Ile Val Leu Phe Ala
                500                 505                 510

Tyr Ser Ser Pro Arg Thr Phe Pro Trp Ile Ile Glu Val Leu Asn Leu
            515                 520                 525

Gln Pro Phe Tyr Phe Tyr Lys Val Ile Glu Val Val Ile Arg Ser Glu
530                 535                 540

Glu Gly Leu Ser Arg Asp Met Val Lys His Leu Asn Ser Ile Glu Glu
545                 550                 555                 560

Gln Ile Leu Glu Ser Leu Ala Trp Ser His Asp Ser Ala Leu Trp Glu
                565                 570                 575

Ala Leu Gln Val Ser Ala Asn Lys Val Pro Thr Cys Glu Glu Val Ile
            580                 585                 590

Phe Pro Asn Asn Phe Glu Thr Gly Asn Gly Asn Val Gln Gly His
            595                 600                 605

Leu Pro Leu Met Pro Met Ser Pro Leu Met His Pro Arg Val Lys Glu
610                 615                 620

Val Arg Thr Asp Ser Gly Ser Leu Arg Arg Asp Met Gln Pro Leu Ser
625                 630                 635                 640

Pro Ile Ser Val His Glu Arg Tyr Ser Ser Pro Thr Ala Gly Ser Ala
                645                 650                 655

Lys Arg Arg Leu Phe Gly Glu Asp Pro Pro Lys Glu Met Leu Met Asp
            660                 665                 670

Lys Ile Ile Thr Glu Gly Thr Lys Leu Lys Ile Ala Pro Ser Ser Ser
        675                 680                 685

Ile Thr Ala Glu Asn Val Ser Ile Leu Pro Gly Gln Thr Leu Leu Thr
690                 695                 700
```

```
Met Ala Thr Ala Pro Val Thr Gly Thr Thr Gly His Lys Val Thr Ile
705                 710                 715                 720

Pro Leu His Gly Val Ala Asn Asp Ala Gly Glu Ile Thr Leu Ile Pro
            725                 730                 735

Leu Ser Met Asn Thr Asn Gln Glu Ser Lys Val Lys Ser Pro Val Ser
        740                 745                 750

Leu Thr Ala His Ser Leu Ile Gly Ala Ser Pro Lys Gln Thr Asn Leu
    755                 760                 765

Thr Lys Ala Gln Glu Val His Ser Thr Gly Ile Asn Arg Pro Lys Arg
770                 775                 780

Thr Gly Ser Leu Ala Leu Phe Tyr Arg Lys Val Tyr His Leu Ala Ser
785                 790                 795                 800

Val Arg Leu Arg Asp Leu Cys Leu Lys Leu Asp Val Ser Asn Glu Leu
            805                 810                 815

Arg Arg Lys Ile Trp Thr Cys Phe Glu Phe Thr Leu Val His Cys Pro
        820                 825                 830

Asp Leu Met Lys Asp Arg His Leu Asp Gln Leu Leu Leu Cys Ala Phe
    835                 840                 845

Tyr Ile Met Ala Lys Val Thr Lys Glu Glu Arg Thr Phe Gln Glu Ile
850                 855                 860

Met Lys Ser Tyr Arg Asn Gln Pro Gln Ala Asn Ser His Val Tyr Arg
865                 870                 875                 880

Ser Val Leu Leu Lys Ser Ile Pro Arg Glu Val Val Ala Tyr Asn Lys
            885                 890                 895

Asn Ile Asn Asp Asp Phe Glu Met Ile Asp Cys Asp Leu Glu Asp Ala
        900                 905                 910

Thr Lys Thr Pro Asp Cys Ser Ser Gly Pro Val Lys Glu Glu Arg Gly
    915                 920                 925

Asp Leu Ile Lys Phe Tyr Asn Thr Ile Tyr Val Gly Arg Val Lys Ser
930                 935                 940

Phe Ala Leu Lys Tyr Asp Leu Ala Asn Gln Asp His Met Met Asp Ala
945                 950                 955                 960

Pro Pro Leu Ser Pro Phe Pro His Ile Lys Gln Gln Pro Gly Ser Pro
            965                 970                 975

Arg Arg Ile Ser Gln Gln His Ser Ile Tyr Ile Ser Pro His Lys Asn
        980                 985                 990

Gly Ser Gly Leu Thr Pro Arg Ser Ala Leu Leu Tyr Lys Phe Asn Gly
    995                 1000                1005

Ser Pro Ser Lys Val Arg
    1010

<210> SEQ ID NO 7
<211> LENGTH: 4903
<212> TYPE: DNA
<213> ORGANISM: homo sapiens

<400> SEQUENCE: 7
gtcgtttgcg gcggcgcagg cgcggtgcgg gcggcggacg ggcgggcgct tcgccgtttg        60
aatggctgcg ggcccgggcc ctcacctcac ctgaggtccg gccgcccagg ggtgcgctat      120
gccgtcggga ggtgaccagt cgccaccgcc cccgcctccc cctccggcgg cggcagcctc      180
ggatgaggag gaggaggacg acggcgaggc ggaagacgcc gcgccgcctg ccgagtcgcc      240 caccccctcag atccagcagc ggttcgacga gctgtgcagc cgcctcaaca tggacgaggc      300
ggcgcgggcc gaggcctggg acagctaccg cagcatgagc gaaagctaca cgctggaggg      360
```

```
aaatgatctt cattggttag catgtgcctt atatgtggct tgcagaaaat ctgttccaac      420
tgtaagcaaa gggacagtgg aaggaaacta tgtatcttta actagaatcc tgaaatgttc      480
agagcagagc ttaatcgaat tttttaataa gatgaagaag tgggaagaca tggcaaatct      540 accccacat ttcagagaac gtactgagag attagaaaga aacttcactg tttctgctgt       600 aattttaag aaatatgaac ccattttca ggacatcttt aataccctc aagaggagca         660 acctcgtcag cagcgaggaa ggaaacagcg gcgacagccc tgtactgtgt ctgaaatttt      720
ccatttttgt tgggtgcttt ttatatatgc aaaaggtaat ttccccatga ttagtgatga      780
tttggtcaat tcttatcacc tgctgctgtg tgctttggac ttagtttatg gaaatgcact      840
tcagtgttct aatcgtaaag aacttgtgaa ccctaatttt aaaggcttat ctgaagattt      900
tcatgctaaa gattctaaac cttcctctga cccccttgt atcattgaga aactgtgttc       960
cttacatgat ggcctagttt tggaagcaaa ggggataaag aacatttct ggaaacccta     1020 tattaggaaa ctttatgaaa aaagctcct taagggaaaa aagaaaatc tcactgggtt      1080 tctagaacct gggaactttg gagagagttt taaagccatc aataaggcct atgaggagta     1140
tgttttatct gttgggaatt tagatgagcg gatatttctt ggagaggatg ctgaggagga     1200
aattgggact ctctcaaggt gtctgaacgc tggttcagga acagagactg ctgaaagggt    1260
gcagatgaaa aacatcttac agcagcattt tgacaagtcc aaagcactta gaatctccac     1320
accactaact ggtgttaggt acattaagga gaatagccct tgtgtgactc cagtttctac     1380
agctacgcat agcttgagtc gtcttcacac catgctgaca ggcctcagga atgcaccaag     1440
tgagaaactg gaacagattc tcaggacatg ttccagagat ccaacccagg ctattgctaa     1500
cagactgaaa gaaatgtttg aaatatattc tcagcatttc cagccagacg aggatttcag     1560
taattgtgct aaagaaattg ccagcaaaca ttttcgtttt gcggagatgc tttactataa     1620
agtattagaa tctgttattg agcaggaaca aaaaagacta ggagacatgg atttatctgg     1680
tattctggaa caagatgcgt tccacagatc tctcttggcc tgctgccttg aggtcgtcac     1740
tttttcttat aagcctcctg ggaattttcc atttattact gaaatatttg atgtgcctct     1800
ttatcatttt tataaggtga tagaagtatt cattagagca gaagatggcc tttgtagaga     1860
ggtggtaaaa caccttaatc agattgaaga acagatctta gatcatttgg catggaaacc     1920
agagtctcca ctctgggaaa aaattagaga caatgaaaac agagttccta catgtgaaga     1980
ggtcatgcca cctcagaacc tggaaagggc agatgaaatt tgcattgctg gctccccttt     2040
gactcccaga agggtgactg aagttcgtgc tgatactgga ggacttggaa ggagcataac     2100
atctccaacc acattatacg ataggtacag ctccccacca gccagcacta ccagaaggcg     2160
gctatttgtt gagaatgata gcccctctga tggaggacg cctgggcgca tgcccccaca     2220
gcccctagtc aatgctgtcc ctgtgcagaa tgtatctggg gagactgttt ctgtcacacc     2280
agttcctgga cagactttgg tcaccatggc aaccgccact gtcacagcca caatgggca     2340 aacggtaacc attcctgtgc aaggtattgc caatgaaaat ggagggataa cattcttccc     2400
tgtccaagtc aatgttgggg ggcaggcaca agctgtgaca ggctccatcc agcccctcag     2460
tgctcaggcc ctggctggaa gtctgagctc tcaacaggtg acaggaacaa ctttgcaagt     2520
ccctggtcaa gtggccattc aacagatttc cccaggtggc caacagcaga agcaaggcca     2580
gtctgtaacc agcagtagta atagacccag gaagaccagc tctttatcgc ttttctttag     2640
aaaggtatac catttagcag ctgtccgcct tcgggatctc tgtgccaaac tagatatttc     2700
```

```
agatgaattg aggaaaaaaa tctggacctg ctttgaattc tccataattc agtgtcctga   2760
acttatgatg gacagacatc tggaccagtt attaatgtgt gccatttatg tgatggcaaa   2820
ggtcacaaaa gaagataagt ccttccagaa cattatgcgt tgttatagga ctcagccgca   2880
ggcccggagc caggtgtata gaagtgtttt gataaaaggg aaaagaaaaa gaagaaattc   2940
tggcagcagt gatagcagaa gccatcagaa ttctccaaca gaactaaaca agatagaac    3000 cagtagagac tccagtccag ttatgaggtc aagcagcacc ttgccagttc acagcccag    3060 cagtgctcct cccacaccta ctcgcctcac aggtgccaac agtgacatgg aagaagagga   3120
gaggggagac ctcattcagt tctacaacaa catctacatc aaacagatta agacatttgc   3180
catgaagtac tcacaggcaa atatggatgc tcctccactc tctccctatc catttgtaag   3240
aacaggctcc cctcgccgaa tacagttgtc tcaaaatcat cctgtctaca tttccccaca   3300
taaaaatgaa acaatgcttt ctcctcgaga aaagattttc tattacttca gcaacagtcc   3360
ttcaaagaga ctgagagaaa ttaatagtat gatacgcaca ggagaaactc ctactaaaaa   3420
gagaggaatt cttttggaag atggaagtga atcacctgca aaaagaattt gcccagaaaa   3480
tcattctgcc ttattacgcc gtctccaaga tgtagctaat gaccgtggtt cccactgagg   3540
ttagtctctt gtattaaact cttcacaaaa tctgtttagc agcagccttt aatgcatcta   3600
gattatggag cttttttcct taatccagct gatgagttac agcctgttag taacatgagg   3660
ggacattttg gtgagaaatg ggacttaact ccttccagtg tccttagaac attttaattc   3720
atcccaactg tctttttttc cctaccattc agtgattact gtcaaggctg cttagaatcc   3780
aaacttggat ttttgactct ggcaaagctt ttagaaatac tgcaagaaaa tgatgtgtac   3840
ccaaacgtga gcataggagg cttctgttga cgtactccaa cagaagaact gtgtttcaag   3900
ttcaatccta cctgttttgt ggtcagctgt agtcctcata aaaagcaaaa caaaaattag   3960
gtattttgtc ctaaaacacc tggtaggagt gtgtgatttt ttgcattcct gacaaaggag   4020
agcacaccca ggtttggagg tcctaggtca ttagccctcg tctcccgttc cctttgtgca   4080
catcttccct ctccccattc ggtgtggtgc agtgtgaaaa gtccttgatt gttcgggtgt   4140
gcaatgtctg agtgaacctg tataagtgga ggcactttag ggctgtaaaa tgcatgattt   4200
tgtaacccag attttgctgt atatttgtga tagcactttc tacaatgtga actttattaa   4260
atacaaaact tccaggctaa acatccaata ttttctttaa tgcttttata tttttttaaa   4320
atgttaaaac ccctatagcc accttttggg aatgttttaa attctccagt ttttttgttat  4380 atagggatca accagctaag aaaagatttt aatcaagttg aattgagggg attaatatga   4440
aaacttatga cctcttcctt taggagggag ttatctaaaa gaaatgtcta ttaaggtgat   4500
atatttaaaa atatttttgg gtgttcctgg cagtttaaaa aaattggttg gagaatttag   4560 gttttttatta gtaccatagt accatttata caaattagaa aatgttattt aacagctgaa   4620
ttatctatac atatctttat taatcactat tgttccagca gttttcaagt caaattaata   4680
atcttattag ggagaaaatt caattgtaaa ttgaatcagt ataaacaaag ttactaggta   4740
acttcatatt gctgagagaa atatggaact tacattgttc aattagaata gtgttctgca   4800
aaaatattta taaacttct caagatactg ctactgtaat tttatatgaa gataagtgta    4860
tttttcaata aagcatttat aaattaaaaa aaaaaaaaa aaa                      4903
```

<210> SEQ ID NO 8
<211> LENGTH: 1139
<212> TYPE: PRT
<213> ORGANISM: homo sapiens

<400> SEQUENCE: 8

```
Met Pro Ser Gly Gly Asp Gln Ser Pro Pro Pro Pro Pro Pro
 1               5                  10                  15

Ala Ala Ala Ser Asp Glu Glu Glu Asp Asp Gly Glu Ala Glu
            20                  25                  30

Asp Ala Ala Pro Pro Ala Glu Ser Pro Thr Pro Gln Ile Gln Gln Arg
            35                  40                  45

Phe Asp Glu Leu Cys Ser Arg Leu Asn Met Asp Gly Ala Ala Arg Ala
 50                  55                  60

Glu Ala Trp Asp Ser Tyr Arg Ser Met Ser Glu Ser Tyr Thr Leu Glu
 65                  70                  75                  80

Gly Asn Asp Leu His Trp Leu Ala Cys Ala Leu Tyr Val Ala Cys Arg
                 85                  90                  95

Lys Ser Val Pro Thr Val Ser Lys Gly Thr Val Glu Gly Asn Tyr Val
                100                 105                 110

Ser Leu Thr Arg Ile Leu Lys Cys Ser Glu Gln Ser Leu Ile Glu Phe
            115                 120                 125

Phe Asn Lys Met Lys Lys Trp Glu Asp Met Ala Asn Leu Pro Pro His
130                 135                 140

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
                165                 170                 175

Pro Gln Glu Glu Gln Pro Arg Gln Gln Arg Gly Arg Lys Gln Arg Arg
            180                 185                 190

Gln Pro Cys Thr Val Ser Glu Ile Phe His Phe Cys Trp Val Leu Phe
            195                 200                 205

Ile Tyr Ala Lys Gly Asn Phe Pro Met Ile Ser Asp Asp Leu Val Asn
210                 215                 220

Ser Tyr His Leu Leu Leu Cys Ala Leu Asp Leu Val Tyr Gly Asn Ala
225                 230                 235                 240

Leu Gln Cys Ser Asn Arg Lys Glu Leu Val Asn Pro Asn Phe Lys Gly
                245                 250                 255

Leu Ser Glu Asp Phe His Ala Lys Asp Ser Lys Pro Ser Ser Asp Pro
            260                 265                 270

Pro Cys Ile Ile Glu Lys Leu Cys Ser Leu His Asp Gly Leu Val Leu
            275                 280                 285

Glu Ala Lys Gly Ile Lys Glu His Phe Trp Lys Pro Tyr Ile Arg Lys
290                 295                 300

Leu Tyr Glu Lys Lys Leu Leu Lys Gly Lys Glu Glu Asn Leu Thr Gly
305                 310                 315                 320

Phe Leu Glu Pro Gly Asn Phe Gly Glu Ser Phe Lys Ala Ile Asn Lys
                325                 330                 335

Ala Tyr Glu Glu Tyr Val Leu Ser Val Gly Asn Leu Asp Glu Arg Ile
            340                 345                 350

Phe Leu Gly Glu Asp Ala Glu Glu Ile Gly Thr Leu Ser Arg Cys
            355                 360                 365

Leu Asn Ala Gly Ser Gly Thr Glu Thr Ala Glu Arg Val Gln Met Lys
370                 375                 380

Asn Ile Leu Gln Gln His Phe Asp Lys Ser Lys Ala Leu Arg Ile Ser
385                 390                 395                 400

Thr Pro Leu Thr Gly Val Arg Tyr Ile Lys Glu Asn Ser Pro Cys Val
```

```
            405                 410                 415
Thr Pro Val Ser Thr Ala Thr His Ser Leu Ser Arg Leu His Thr Met
            420                 425                 430

Leu Thr Gly Leu Arg Asn Ala Pro Ser Glu Lys Leu Glu Gln Ile Leu
            435                 440                 445

Arg Thr Cys Ser Arg Asp Pro Thr Gln Ala Ile Ala Asn Arg Leu Lys
450             455                 460

Glu Met Phe Glu Ile Tyr Ser Gln His Phe Gln Pro Asp Glu Asp Phe
465                 470                 475                 480

Ser Asn Cys Ala Lys Glu Ile Ala Ser Lys His Phe Arg Phe Ala Glu
                485                 490                 495

Met Leu Tyr Tyr Lys Val Leu Glu Ser Val Ile Glu Gln Glu Gln Lys
            500                 505                 510

Arg Leu Gly Asp Met Asp Leu Ser Gly Ile Leu Glu Gln Asp Ala Phe
            515                 520                 525

His Arg Ser Leu Leu Ala Cys Cys Leu Glu Val Val Thr Phe Ser Tyr
            530                 535                 540

Lys Pro Pro Gly Asn Phe Pro Phe Ile Thr Glu Ile Phe Asp Val Pro
545                 550                 555                 560

Leu Tyr His Phe Tyr Lys Val Ile Glu Val Phe Ile Arg Ala Glu Asp
                565                 570                 575

Gly Leu Cys Arg Glu Val Val Lys His Leu Asn Gln Ile Glu Glu Gln
            580                 585                 590

Ile Leu Asp His Leu Ala Trp Lys Pro Glu Ser Pro Leu Trp Glu Lys
            595                 600                 605

Ile Arg Asp Asn Glu Asn Arg Val Pro Thr Cys Glu Glu Val Met Pro
            610                 615                 620

Pro Gln Asn Leu Glu Arg Ala Asp Glu Ile Cys Ile Ala Gly Ser Pro
625                 630                 635                 640

Leu Thr Pro Arg Arg Val Thr Glu Val Arg Ala Asp Thr Gly Gly Leu
                645                 650                 655

Gly Arg Ser Ile Thr Ser Pro Thr Thr Leu Tyr Asp Arg Tyr Ser Ser
            660                 665                 670

Pro Pro Ala Ser Thr Thr Arg Arg Leu Phe Val Glu Asn Asp Ser
            675                 680                 685

Pro Ser Asp Gly Gly Thr Pro Gly Arg Met Pro Pro Gln Pro Leu Val
            690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
                725                 730                 735

Ala Asn Asn Gly Gln Thr Val Thr Ile Pro Val Gln Gly Ile Ala Asn
            740                 745                 750

Glu Asn Gly Gly Ile Thr Phe Phe Pro Val Gln Val Asn Val Gly Gly
            755                 760                 765

Gln Ala Gln Ala Val Thr Gly Ser Ile Gln Pro Leu Ser Ala Gln Ala
            770                 775                 780

Leu Ala Gly Ser Leu Ser Ser Gln Gln Val Thr Gly Thr Thr Leu Gln
785                 790                 795                 800

Val Pro Gly Gln Val Ala Ile Gln Gln Ile Ser Pro Gly Gly Gln Gln
                805                 810                 815

Gln Lys Gln Gly Gln Ser Val Thr Ser Ser Ser Asn Arg Pro Arg Lys
            820                 825                 830
```

```
Thr Ser Ser Leu Ser Leu Phe Phe Arg Lys Val Tyr His Leu Ala Ala
        835                 840                 845

Val Arg Leu Arg Asp Leu Cys Ala Lys Leu Asp Ile Ser Asp Glu Leu
850                 855                 860

Arg Lys Lys Ile Trp Thr Cys Phe Glu Phe Ser Ile Ile Gln Cys Pro
865                 870                 875                 880

Glu Leu Met Met Asp Arg His Leu Asp Gln Leu Leu Met Cys Ala Ile
                885                 890                 895

Tyr Val Met Ala Lys Val Thr Lys Glu Asp Lys Ser Phe Gln Asn Ile
                900                 905                 910

Met Arg Cys Tyr Arg Thr Gln Pro Gln Ala Arg Ser Gln Val Tyr Arg
                915                 920                 925

Ser Val Leu Ile Lys Gly Lys Arg Lys Arg Arg Asn Ser Gly Ser Ser
                930                 935                 940

Asp Ser Arg Ser His Gln Asn Ser Pro Thr Glu Leu Asn Lys Asp Arg
945                 950                 955                 960

Thr Ser Arg Asp Ser Ser Pro Val Met Arg Ser Ser Ser Thr Leu Pro
                965                 970                 975

Val Pro Gln Pro Ser Ser Ala Pro Pro Thr Pro Thr Arg Leu Thr Gly
                980                 985                 990

Ala Asn Ser Asp Met Glu Glu Glu Glu Arg Gly Asp Leu Ile Gln Phe
                995                1000                1005

Tyr Asn Asn Ile Tyr Ile Lys Gln Ile Lys Thr Phe Ala Met Lys Tyr
                1010                1015                1020

Ser Gln Ala Asn Met Asp Ala Pro Pro Leu Ser Pro Tyr Pro Phe Val
1025                1030                1035                1040

Arg Thr Gly Ser Pro Arg Arg Ile Gln Leu Ser Gln Asn His Pro Val
                1045                1050                1055

Tyr Ile Ser Pro His Lys Asn Glu Thr Met Leu Ser Pro Arg Glu Lys
                1060                1065                1070

Ile Phe Tyr Tyr Phe Ser Asn Ser Pro Ser Lys Arg Leu Arg Glu Ile
                1075                1080                1085

Asn Ser Met Ile Arg Thr Gly Glu Thr Pro Thr Lys Lys Arg Gly Ile
                1090                1095                1100

Leu Leu Glu Asp Gly Ser Glu Ser Pro Ala Lys Arg Ile Cys Pro Glu
1105                1110                1115                1120

Asn His Ser Ala Leu Leu Arg Arg Leu Gln Asp Val Ala Asn Asp Arg
                1125                1130                1135

Gly Ser His

<210> SEQ ID NO 9
<211> LENGTH: 1164
<212> TYPE: DNA
<213> ORGANISM: homo sapiens

<400> SEQUENCE: 9
cgctcaggga aggcgggtgc gcgcctgcgg ggcggagatg ggcagggggc ggtgcgtggg      60
tcccagtctg cagttaaggg ggcaggagtg gcgctgctca cctctggtgc aaagggcgg     120 cgcagcggct gccgagctcg gccctggagg cggcgagaac atggtgcgca ggttcttggt     180
gaccctccgg attcggcgcg cgtgcggccc gccgcgagtg agggttttcg tggttcacat     240
cccgcggctc acggggagt gggcagcgcc agggcgcccc gccgctgtgg ccctcgtgct     300
gatgctactg aggagccagc gtctagggca gcagccgctt cctagaagac caggtcatga     360
```

```
tgatgggcag cgcccgagtg gcggagctgc tgctgctcca cggcgcggag cccaactgcg     420
ccgaccccgc cactctcacc cgacccgtgc acgacgctgc ccgggagggc ttcctggaca     480
cgctggtggt gctgcaccgg gccggggcgc ggctggacgt gcgcgatgcc tggggccgtc     540
tgcccgtgga cctggctgag gagctgggcc atcgcgatgt cgcacggtac ctgcgcgcgg     600
ctgcgggggg caccagaggc agtaaccatg cccgcataga tgccgcggaa ggtccctcag     660
acatccccga ttgaaagaac cagagaggct ctgagaaacc tcgggaaact tagatcatca     720
gtcaccgaag gtcctacagg gccacaactg cccccgccac aacccacccc gctttcgtag     780
ttttcattta gaaaatagag cttttaaaaa tgtcctgcct tttaacgtag atatatgcct     840
tcccccacta ccgtaaatgt ccatttatat catttttta atattcttat aaaaatgtaa     900 aaagaaaaa caccgcttct gccttttcac tgtgttggag ttttctggag tgagcactca     960
cgccctaagc gcacattcat gtgggcattt cttgcgagcc tcgcagcctc cggaagctgt    1020
cgacttcatg acaagcattt tgtgaactag ggaagctcag gggggttact ggcttctctt    1080
gagtcacact gctagcaaat ggcagaacca aagctcaaat aaaaataaaa taattttcat    1140
tcattcactc aaaaaaaaaa aaaa                                            1164
```

<210> SEQ ID NO 10
<211> LENGTH: 132
<212> TYPE: PRT
<213> ORGANISM: homo sapiens

<400> SEQUENCE: 10

```
Met Val Arg Arg Phe Leu Val Thr Leu Arg Ile Arg Arg Ala Cys Gly
 1               5                  10                  15

Pro Pro Arg Val Arg Val Phe Val His Ile Pro Arg Leu Thr Gly
            20                  25                  30

Glu Trp Ala Ala Pro Gly Ala Pro Ala Ala Val Ala Leu Val Leu Met
        35                  40                  45

Leu Leu Arg Ser Gln Arg Leu Gly Gln Gln Pro Leu Pro Arg Arg Pro
    50                  55                  60

Gly His Asp Asp Gly Gln Arg Pro Ser Gly Ala Ala Ala Ala Pro
65                  70                  75                  80

Arg Arg Gly Ala Gln Leu Arg Arg Pro Arg His Ser His Pro Thr Arg
                85                  90                  95

Ala Arg Arg Cys Pro Gly Gly Leu Pro Gly His Ala Gly Gly Ala Ala
            100                 105                 110

Pro Gly Arg Gly Ala Ala Gly Arg Ala Arg Cys Leu Gly Pro Ser Ala
        115                 120                 125

Arg Gly Pro Gly
    130
```

<210> SEQ ID NO 11
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 11
aggugaugau gaugggcaau u     21

<210> SEQ ID NO 12
<211> LENGTH: 21

```
<212> TYPE: RNA
<213> ORGANISM: Artificial Sequence
<220> FEATURE:
<223> OTHER INFORMATION: synthetic oligonucleotide

<400> SEQUENCE: 12
gcucuggcuu ucgugaacau g                                              21

<210> SEQ ID NO 13
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 13
gaggagaatt ctgtgggcca gggctgtg                                       28

<210> SEQ ID NO 14
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 14
gtacgagctc gagccgctgg gagatgtt                                       28

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 15
caggcttgag tttgaagaaa ttg                                            23

<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 16
atgccccaga gttccttctt c                                              21

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 17 cgccttttc ttcttagctt ca                                              22

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 18
```

```
agtttctcat gccattcctt tc                                              22

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
cccactccaa gagagggttt                                                 20

<210> SEQ ID NO 20
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 20
agctatgccc gtcggtct                                                   18

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
gcgtaccagc aactttaccc                                                 20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ggcaccaaag ccactaacat                                                 20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
tcgctgttgt ttccctctct                                                 20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
gatcttgagt gccacgatga                                                 20

<210> SEQ ID NO 25
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 25
catcgccacc ttcaagaact                                               20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
agctgctcaa ttgactgacg                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
ggctggatca gcaagagaag                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
cctgctgggt gaagaatgtt                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
tccagtacat tgagcgccta                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
gggctgggtg ttagccttat                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
tgagaaggaa gcgctggtat                                               20
```

```
<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
tctgcaatct gttccgtgag                                                    20

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
gatcttcaag aaggctggtc ac                                                 22

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
caatgattgg acttccagga g                                                  21

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
cactgagcat ctccctcaca                                                    20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
tgggtgcagc gaactttatt                                                    20
```

METHODS OF INDUCING TISSUE REGENERATION

CROSS REFERENCE TO RELATED APPLICATIONS

Pursuant to 35 U.S.C. §119 (e), this application claims priority to the filing date of the U.S. Provisional Patent Application Ser. No. 61/281,575 filed Nov. 18, 2009; the disclosure of which are herein incorporated by reference.

FEDERALLY-SPONSORED RESEARCH OR DEVELOPMENT

This invention was made with Government support under contracts AG009521, AG020961, HD007249, and AR051678 awarded by the National Institutes of Health. The Government has certain rights in this invention.

FIELD OF THE INVENTION

This invention pertains to methods for inducing tissue regeneration by producing cells within a lineage, i.e. lineage-restricted cells, from post-mitotic differentiated cells of the same lineage ex vivo and in vivo. Also provided are kits for performing these methods.

BACKGROUND OF THE INVENTION

Tissue regeneration in humans is extremely limited and constitutes a major challenge to the repair of damaged organ function. A number of organs rely on undifferentiated stem and progenitor cells for tissue regeneration. However, it is unclear if resident stem cells are capable of regenerating the full mass of tissue required for a given injury. Furthermore, stem cells have not yet been identified for a number of tissues, and in those tissues in which stem cells have been identified, the factors required to induce their propagation and differentiation to acquire the fates of cells in these tissues are not fully understood. Thus, there is a need for methods of inducing well defined differentiated cells of known identity to contribute to cell replacement and tissue regeneration in vivo. Moreover, propagation of such cells ex vivo can be used as cell based therapies upon delivery in vivo. Such methods are also applicable to modeling human diseases ex vivo (eg. skeletal, neuronal, cardiac, pancreatic, hepatic diseases and the like) and elucidating the underlying defects. In addition drugs capable of ameliorating the human disease phenotype can be screened using such disease models.

SUMMARY OF THE INVENTION

Methods for producing cells within a lineage, i.e. lineage-restricted cells (LRCs), from post-mitotic differentiated cells (PMDs) of the same lineage ex vivo and in vivo are provided, wherein the lineage-restricted cells may encompass mitotic progenitor cells committed to a cell lineage (MPC), post-mitotic immature cells committed to a particular type of cell in the cell lineage (post-mitotic immature cell, PMI), and post-mitotic differentiated cells of the cell lineage (post-mitotic differentiated cell, PMD). Also provided are methods for treating a subject in need of tissue regeneration therapy by employing cells produced by methods of the invention. Also provided are kits for performing these methods.

In some embodiments of the invention, a post-mitotic differentiated cell (PMD) is contacted ex vivo with an effective amount of an agent that transiently inhibits activity of a member of the pocket protein family of cell cycle regulators (i.e. a pocket protein) and an effective amount of an agent that transiently inhibits activity of the cyclin-dependent kinase inhibitor 2A (CDKNA2) alternate reading frame protein (ARF). Contact with these agents occurs under conditions that are sufficient to induce the PMD cell to transiently become a replication competent cell (RCC) and divide to produce non-tumorigenic progeny that are post-mitotic immature cells (PMI) of the same lineage as the PMD. In some embodiments, the PMD dedifferentiates in the course of becoming a RCC. In some embodiments, the PMD is a myocyte, e.g., a cardiomyocyte. In some embodiments, the PMD is a hepatocyte. In some embodiments, the PMD is a neuron, e.g. a dopaminergic neuron. Any tissue that harbors post-mitotic cells (e.g. muscle, brain, skin, pancreas, liver, etc) is embodied herein, In some embodiments, the pocket protein is retinoblastoma protein (RB). In some embodiments, the agent that transiently inhibits RB activity transiently inhibits synthesis of RB protein. In some embodiments, the agent that transiently inhibits ARF transiently inhibits synthesis of ARF protein. In some embodiments, about 10% of PMD present in a population of cells are induced to become RCC and divide.

In some embodiments, a population of progeny PMI are provided with conditions that promote differentiation, so as to produce a population of PMD of a desired lineage. In certain embodiments, progeny PMI are transferred to differentiation conditions by transplanting the progeny to a target site in a subject. In some embodiments, the subject is a subject in need of tissue regeneration therapy, desirably at the target site of transplantation.

In some embodiments of the invention, post-mitotic differentiated cells (PMDs) in a tissue are contacted in vivo with an effective amount of an agent that transiently inhibits the activity of a member of the pocket protein family of cell cycle regulators (i.e. a pocket protein) and an effective amount of an agent that transiently inhibits activity of the cyclin-dependent kinase inhibitor 2A (CDKNA2) alternate reading frame protein (ARF), where the contacted PMDs are induced to transiently become replication competent cells (RCCs) and divide in situ to produce a population of post-mitotic immature cells (PMIs) of the lineage of the tissue. In some embodiments, the PMD dedifferentiates in the course of becoming a RCC. In some embodiments, the post-mitotic differentiated cells are myocytes, e.g. cardiomyocytes. In some embodiments, the PMD are hepatocytes. In some embodiments, the PMD are neurons, e.g. dopaminergic neurons. Any tissue that harbors post-mitotic cells is embodied herein (eg. pancreas), In some embodiments, the pocket protein is retinoblastoma protein (RB). In some embodiments, the agent that transiently inhibits RB activity transiently inhibits synthesis of RB protein. In some embodiments, the agent that transiently inhibits ARF transiently inhibits synthesis of ARF protein. In some embodiments, the agent that transiently inhibits the activity of the pocket protein and the agent that transiently inhibits the activity of ARF are administered to a target site in a subject. In some embodiments, the subject is a subject in need of tissue regeneration therapy, desirably at the target site of administration of the agent.

In some embodiments, the PMDs are derived from an individual with a disease to characterize that disease (e.g. cortical neurons from Alzheimer's patients, dopaminergic neurons from Parkinson's patients, cardiomyocytes from patients with heritable and acquired cardiac diseases, and the like). In some embodiments, the PMDs are derived from an individual that is alive, e.g. the PMDs are from a live tissue biopsy. In some embodiments, the PMDs are derived from a patient that has died, i.e. the PMDs are from a cadaver.

In some aspects of the invention, a method is provided for screening a candidate agent for an effect on a disease condition. In these methods, lineage-restricted cells (LRCs) are produced from a post-mitotic differentiated cell (PMD) from an individual with a disease condition by methods described above. The LRCs are transferred to conditions that promote differentiation to produce a differentiated population of cells. Cells that are differentiated are contacted with a candidate agent, and the viability and/or function of the cells in the differentiated population are compared to the viability and/or function of differentiated cells not contacted with the candidate agent; wherein enhanced viability and/or function of the cells in the differentiated population contacted with the candidate agent as compared to a differentiated population not contacted with the candidate agent indicates that the candidate agent will have an effect on the disease condition. In some embodiments, the disease condition is a muscle disorder. In some embodiments, the muscle is smooth muscle, skeletal muscle, or cardiac muscle. In some embodiments, the disease condition is a nervous system disorder. In some embodiments, the nervous system disorder is Parkinson's Disease, Alzheimer's Disease, ALS, a disorder of olfactory neurons, a disorder of spinal cord neurons, or a disorder of peripheral neurons. In some embodiments, the PMDs are derived from an individual that is alive. In some embodiments, the PMDs are derived from a cadaver.

In some aspects of the invention, a method is provided for screening a candidate agent for toxicity to a human. In these methods, lineage-restricted cells (LRCs) are produced from a post-mitotic differentiated cell (PMD) from a healthy individual by the subject methods described above. The LRCs are transferred to conditions that promote differentiation to produce a differentiated population of cells. The differentiated population of cells is contacted with a candidate agent, and the viability and/or function of the cells in the differentiated population is compared to the viability and/or function of differentiated cells not contacted with said candidate agent; wherein a decrease in viability and/or function of the cells in the differentiated population contacted with the candidate agent as compared to a differentiated population not contacted with the candidate agent indicates that the candidate agent is toxic to a human. In some embodiments, the PMD is a hepatocyte. In some embodiments, the function of the cells is assess by assessing a cytochrome P450 panel.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(A) PALM isolated myoblasts at 48 hrs post-isolation, at 96 hrs post-isolation. Three weeks post-isolation, captured myoblasts were placed in Differentiation Medium (DM). Images show culture after 3 days in DM (DM3). (B) PALM isolated myogenin-promoter-GFP myocytes treated with TAM and p16/19si, prior to microdissection, 72 hrs post-isolation displaying both phase and native GFP imaging. Three weeks post-isolation expanded and dedifferentiated myoblasts were placed in DM, and images show culture after 3 days in DM (DM3) as well as after 6 days in DM (DM6). Growth medium (GM).

Figure 21:
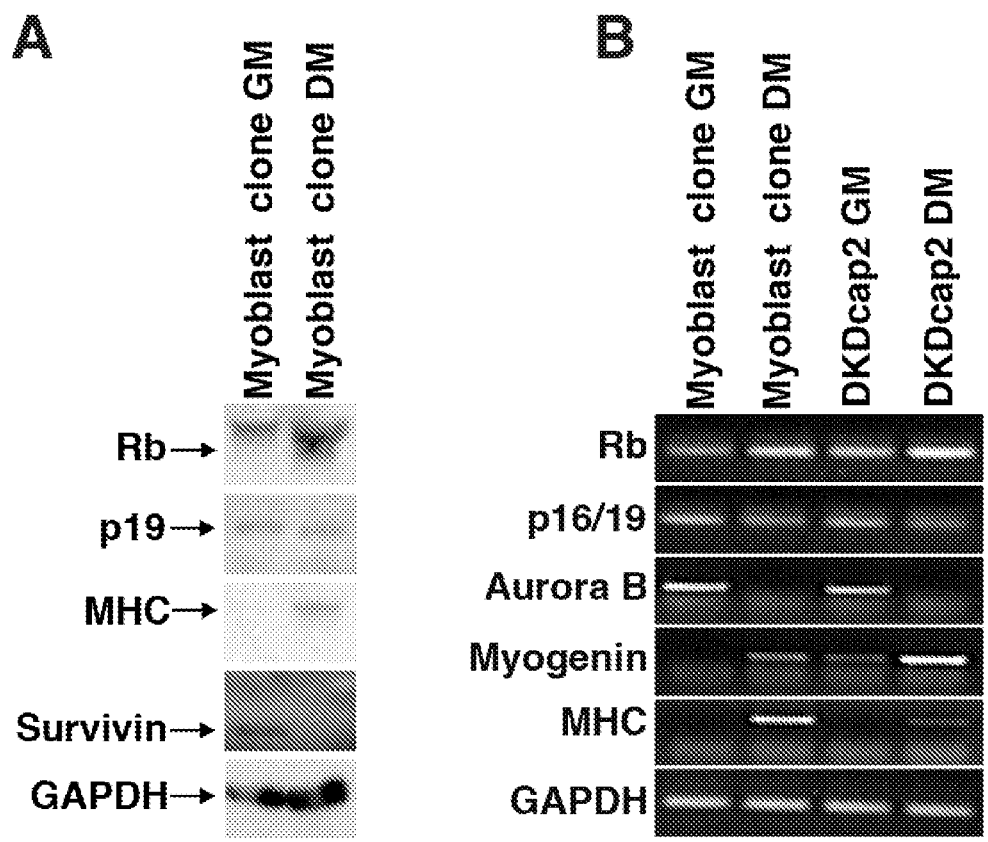

FIG. 21. Expression patterns of PALM isolated myoblast colonies and DKD treated myocyte colonies. (A) Western blot analysis of PALM isolated primary myoblast colony in GM and DM4, showing protein levels of RB (100 kDa), p19ARF (20 kDa), MHC (220 kDa), and Survivin (20 kDa). GAPDH (35 kDa) is loading control. (B) sqRT-PCR analysis of PALM isolated primary myoblasts and DKD treated myocytes in GM and DM4. Growth medium (GM); Myotubes cultured in differentiation medium for 4 or 5 days (DM4 or DM5 respectively).

Figure 22:
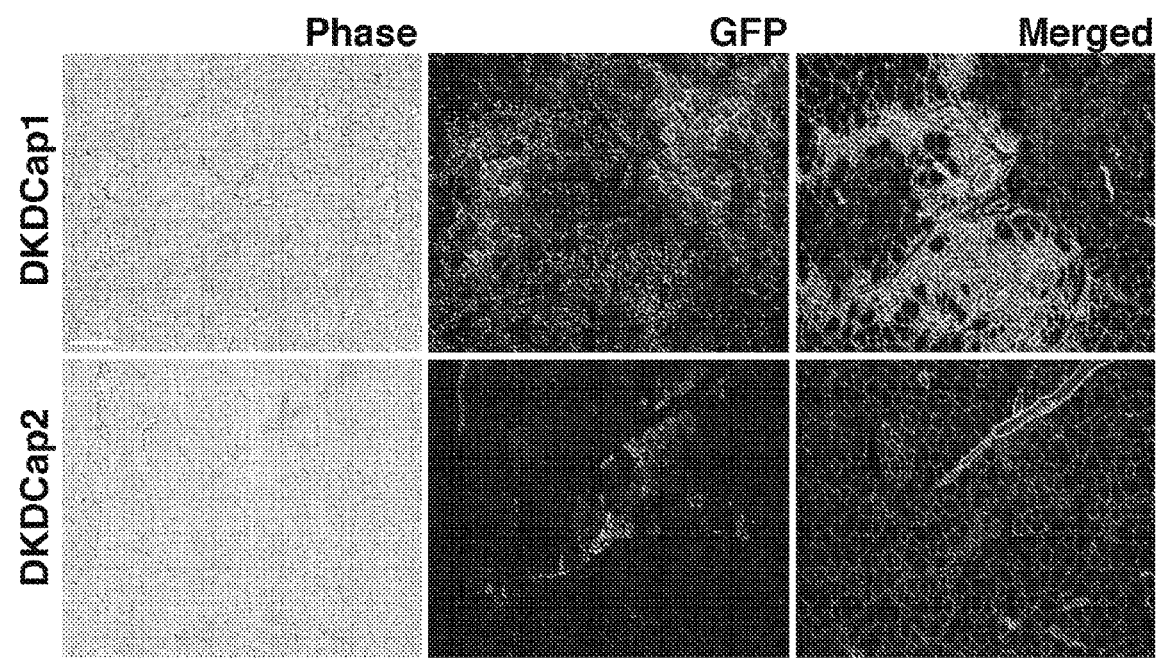

FIG. 22. DKD dedifferentiated, captured and expanded myocytes fuse to muscle in vivo. Representative fields of cross-sections of tibialis anterior of CB17/SCID mice 10 days post-injection of $1.5 \times 10^5$ cells from DKD captured and expanded myocytes. Sections were stained for Hoechst 33258 (blue), GFP (green) and laminin (orange). Incorporation of dedifferentiated myocytes into pre-existing fibers can be visualized in merged fields by GFP staining of a laminin-bound fibers; GFP expression marks myogenin expression in fibers where dedifferentiated myocytes fused. Bar 100 μm.

DETAILED DESCRIPTION OF THE INVENTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Methods for producing cells within a lineage, i.e. lineage-restricted cells (LRCs), from post-mitotic differentiated cells (PMDs) of the same lineage ex vivo and in vivo are provided, wherein the lineage-restricted cells may encompass mitotic progenitor cells committed to a cell lineage (MPC), post-mitotic immature cells committed to the cell lineage (post-mitotic immature cell, PMI), and post-mitotic differentiated cells of the cell lineage (post-mitotic differentiated cell, PMD). The subject lineage-restricted cells that are produced are useful in tissue regeneration; for drug screening; as experimental models of cellular differentiation; for screening in vitro assays to define growth and differentiation factors and to characterize genes involved in cell development and regulation; and the like. These cells may be used directly for these purposes, or they may be genetically modified to provide altered capabilities. These and other objects, advantages, and features of the invention will become apparent to those persons skilled in the art upon reading the details of the compositions and methods as more fully described below.

The term "lineage-restricted cell", or "LRC", is used herein to mean a cell within a defined lineage. LRCs encompass mitotic progenitor cells committed to a defined cell lineage (MPC), post-mitotic immature cells committed to a particular type of cell in the cell lineage (post-mitotic immature cell, PMI), and post-mitotic differentiated cells of that cell lineage (post-mitotic differentiated cell, PMD). A lineage-restricted cell is not pluripotent; in other words, it cannot be induced to differentiate into all cell types in the embryo. Rather, it is restricted to differentiating into only the cell or cells of a specified lineage. Examples of lineages would be the skeletal muscle lineage, the cardiac muscle lineage, the neuronal lineage, the pancreatic islet cell lineage, etc.

The term "mitotic progenitor cell", or "MPC", is used to describe a mitotic progenitor cell committed to a defined cell lineage. MPC are cells that are able to self-regenerate as well as generate daughter cells of their cell lineage. In other words, an MPC is a mitotic cell that, upon division, gives rise to a) more MPC and/or b) post-mitotic immature cells committed to a particular cell type in the cell lineage (post-mitotic immature cells, PMIs). MPCs are recognizable as such by their expression of one or more markers, i.e. proteins, RNA, etc. that are known in the art to be characteristic of an immature state of differentiation for their cell lineage. In addition, progenitor cells are typically mitotic, and thus incorporate BrdU into their DNA and/or express one or more markers, e.g. proteins, that are typically expressed in mitotic cells, e.g.

Ki67, PCNA, Anillin, AuroraB, and Survivin. An example of an MPC is a progenitor cell of the muscle lineage, namely a myoblast, as it can give rise to more myoblasts and/or post-mitotic muscle precursors.

The term "post-mitotic immature cell", or "PMI", refers to post-mitotic precursor cells committed to a particular cell type in the cell lineage, that is, post-mitotic cells that have committed to a cell fate but have not yet differentiated to that cell fate. The PMI typically does not have all of the defining characteristics of a fully mature cell of the lineage. PMIs of a lineage are recognizable as such by their expression of one or more markers and a characteristic morphology as is well known in the art. In addition, PMIs are distinguishable from MPCs because they are post-mitotic and thus do not incorporate BrdU into their DNA or express markers that are typically expressed in mitotic cells, e.g. Ki67, PCNA, Anillin, AuroraB, and Survivin. An example of a PMI is a precursor cell of the cardiac muscle lineage, as it is post-mitotic but has not fully differentiated into a cardiomyocyte.

The term "post-mitotic differentiated cell", or PMD, is used herein to refer to a post-mitotic cell of a cell lineage that has differentiated into a mature, functional cell of a tissue. PMDs express markers that are well-known to the artisan as characteristic of a mature cell fate. In addition, because PMDs are post-mitotic, they do not incorporate BrdU into their DNA or express markers that are typically expressed in proliferating cells, e.g. Ki67, PCNA, Anillin, AuroraB, Survivin, etc. An example of a PMD is a cardiomyocyte, a myofiber, a hepatocyte, a neuron, and the like.

The term "replication competent cell," or "RCC", is used to describe a cell that is capable of mitosis. RCC cells may express markers characteristic of a MPC or a PMI, i.e. markers that are known in the art to be characteristic of an immature state of differentiation for their cell lineage. Alternatively, they may express markers of a PMD, i.e. markers that are well-known to the artisan as characteristic of a mature cell fate. In either instance, they incorporate BrdU into their DNA and/or express one or more markers, e.g. proteins, that are typically expressed in mitotic cells, e.g. Ki67, PCNA, Anillin, AuroraB, Survivin, and the like.

It will be understood by those of skill in the art that in discussing the expression of markers by cells as above, the stated expression levels reflect detectable amounts of the marker. A cell that is negative for staining for a marker protein (the level of binding of a marker specific reagent is not detectably different from an isotype matched control) may still express minor amounts of the marker. And while it is commonplace in the art to refer to cells as "positive" or "negative" for a particular marker, actual expression levels are a quantitative trait. For example, the number of molecules on the cell surface can vary by several logs, yet still be characterized as "positive". The staining intensity of cells can be monitored by flow cytometry, where lasers detect the quantitative levels of fluorochrome (which is proportional to the amount of cell surface marker bound by specific reagents, e.g. antibodies). Although the absolute level of staining may differ with a particular fluorochrome and reagent preparation, the data can be normalized to a control. Alternatively, the staining intensity of cells can be monitored by immunohistochemistry or immunofluorescence. Cell-specific markers that are cell surface proteins may be observed without fixing the cells, i.e. while maintaining cell viability, e.g. by flow cytometry. Alternatively, intracellular markers may be observed in a subpopulation of the subject cells that are fixed and prepared by methods known in the art.

By "dedifferentiate", it is meant that cells revert from a more differentiated state to a less differentiated state in a cell lineage. In other words, the cells lose traits, e.g. morphology, expression of certain genes, functional capabilities etc. of the more differentiated cell and acquire traits of cells of the lineage that are less mature. By "transiently dedifferentiate," it is meant that the dedifferentiation phase is temporary; that is, that after a given amount of time and/or under certain given conditions, the dedifferentiated cells and/or their progeny will be permitted to differentiate to a more mature fate, unlike a tumor cell, which is not able to do so.

By "proliferate" it is meant to divide by mitosis, i.e. undergo mitosis. An "expanded population" is a population of cells that has proliferated, i.e. undergone mitosis, such that the expanded population has an increase in cell number, that is, a greater number of cells, than the population at the outset.

The term "explant" refers to a portion of an organ or tissue therein taken from the body and cultured in an artificial medium. Cells that are grown "ex vivo" are cells that are taken from the body in this manner, temporarily cultured in vitro, and returned to the body.

The term "primary culture" denotes a mixed cell population of cells from an organ or tissue within an organ. The word "primary" takes its usual meaning in the art of tissue culture.

The term "tissue" refers to a group or layer of similarly specialized cells which together perform certain special functions.

The term "organ" refers to two or more adjacent layers of tissue, which layers of tissue maintain some form of cell-cell and/or cell-matrix interaction to form a microarchitecture.

A "pocket protein" is a protein that is a member of the pocket protein family of cell cycle regulators. Pocket proteins are tumor suppressor proteins; in other words, they are negative regulators of the cell cycle. There are three known pocket proteins: Retinoblastoma protein (also called RB, RB1, pRB, OSRC, pp110 or p105-RB), p107 (also called RBL1, CP107), and p130 (also called RB2). The human RB polypeptide sequence and the nucleotide sequence that encodes it may be found at Genbank Ref. No. NM_000321 (SEQ ID NO:1 and SEQ ID NO:2). The human p107 polypeptide sequence and the nucleotide sequence that encodes it may be found at Genbank Ref. Nos. NM_002895 (variant 1; SEQ ID NO:3 and SEQ ID NO:4), and NM_183404 (variant 2; SEQ ID NO:5 and SEQ ID NO:6). The human p130 polypeptide sequence and the nucleotide sequence that encodes it may be found at Genbank Ref. No. NM_005611 (SEQ ID NO:7 and SEQ ID NO:8). These proteins negatively regulate the cell cycle in part by repressing E2F transcription factor activity to limit the expression of genes required for cell cycle progression. In the canonical signaling pathway, members of the pocket protein family bind members of the E2F family of proteins to prevent E2F-directed transcription of genes that mediate entry into the cell cycle. Phosphorylation of the pocket proteins or disruption of the pocket protein-E2F interaction releases the E2F proteins, which can now induce the transcription of genes that mediate S-phase entry. This and other mechanisms of action of the pocket proteins are described in more detail in Cobrinik (2005) Oncogene 24:2796-2809, the disclosure of which is incorporated herein by reference.

An "agent that transiently inhibits the activity of a pocket protein" is an agent that transiently antagonizes, inhibits or otherwise negatively regulates the pocket protein's modulation of a cell's activity. Agents that transiently inhibit pocket protein activity can act anywhere along the pocket protein signaling pathway to antagonize pocket protein signaling. Thus, for example, based upon the above described paradigm of pocket protein signaling, agents that inhibit pocket protein modulation of cell activity include those that prevent the synthesis of the pocket protein (e.g. siRNAs for RB, p107, or p130), induce the phosphorylation of the pocket protein (e.g. D cyclin peptides); disrupt binding between the pocket protein and E2F (e.g. human papillomavirus peptide E7); overcome the activity of the pocket protein (e.g. E2F peptides); etc.

The "cyclin-dependent kinase inhibitor 2A (CDKNA2) alternate reading frame" (ARF, also known as p14ARF in humans and p19ARF in mice) is the polypeptide encoded by transcript variant/isoform 4 of the cyclin-dependent kinase inhibitor 2A (CDKNA2, Ink4a, MTS) gene. The ARF polypeptide sequence and the sequence of the CDKNA2 gene that encodes it may be found at Genbank Ref. No. NM_058195 (SEQ ID NO:9 and SEQ ID NO:10). The variant is encoded by an alternate first exon located 20 Kb upstream of the remainder of the gene, which renders the ARF protein structurally unrelated to the proteins encoded by the other CDKNA2 transcript variants p16Ink4a (Genbank Ref. No. NM_000077) and isoform 3 (NM_058197, NP_478104). ARF functions as a stabilizer of the tumor suppressor protein p53, in part by interacting with and sequestering HDM2 (MDM2 p53 binding protein homolog, also called HDMX and MDM2), which is normally responsible for the degradation of p53. During mitosis, Not dead yet 1 (NDY1/KDM2b) represses ARF expression by inducing histone H3K27 trimethylation of the ARF locus; in the absence of ARF protein, HDM2 proteins are available to degrade p53, thereby relieving p53-mediated suppression of mitosis. This and other mechanisms of action of the ARF protein are well known in the art.

An "agent that transiently inhibits the activity of ARF" is an agent that transiently antagonizes, inhibits or otherwise negatively regulates the ARF modulation of cell activity. Agents that inhibit ARF activity can act anywhere along the ARF signaling pathway to antagonize ARF signaling. Thus, for example, based upon the above described paradigm of ARF signaling, agents that inhibit ARF modulation of cell activity include those that inhibit the expression of ARF (e.g. NDY1 peptide), prevent the synthesis of the ARF protein (e.g. ARF siRNA), overcome the activity of the ARF protein (e.g. HDM2 peptide), etc.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

As summarized above, the subject invention provides methods for producing cells within a lineage, i.e. lineage-restricted cells (LRCs), from post-mitotic differentiated cells (PMDs) of the same lineage ex vivo and in vivo, wherein the lineage-restricted cells may encompass mitotic progenitor cells committed to a cell lineage (mitotic progenitor cells, MPC), post-mitotic immature cells committed to a particular type of cell in the cell lineage (post-mitotic immature cell, PMI), and post-mitotic differentiated cells of that lineage (post-mitotic differentiated cell, PMD). In further describing the subject invention, the subject methods are described first in greater detail, followed by a review of various representative applications in which the subject invention finds use as well as kits that find use in practicing the subject invention.

In practicing the subject methods, post-mitotic differentiated cells (PMDs) are contacted with an agent that transiently inhibits activity of one or more members of the pocket protein family of cell cycle regulators, and an agent that transiently inhibits activity of the transcript variant of the cyclin-dependent kinase inhibitor 2A referred to as ARF. As defined above, PMDs are cells that have completed differentiation to become mature, functional cells in a tissue, e.g. a myocyte in skeletal or heart muscle, an islet cell in pancreas, a hepatocyte in liver, a neuron in CNS tissue or peripheral neural tissue, an osteocyte in bone, hematopoietic cell from blood, etc. PMDs can be identified as such by the expression of one or more proteins or RNAs, i.e. markers, as will be known in the art. In addition, these cells may express one or more subtype-specific markers, as will also be known in the art. In some embodiments, the subject PMDs cells are myocytes, which express one or more of myogenin, myosin heavy chain (MHC), and creatine kinase. In certain embodiments, the myocytes are cardiomyocytes, which are rod shaped and cross-striated in culture and express one or more of proteins cardiac troponin, eHand transcription factor, and cardiac-specific myosins. In certain embodiments, the myocytes are smooth muscle myocytes, which express smooth muscle actin. In certain embodiments, the myocytes are skeletal muscle myocytes, which express one or more of skeletal muscle myosins, skeletal muscle troponin, myoD.

In some embodiments, subject PMDs are contacted with agents in vivo, that is, in the tissue in which they reside, i.e. in situ. In some embodiments, subject PMDs are contacted with agents ex vivo, that is, they are harvested from the body and contacted with agents in vitro. In cases when the method is to be performed ex vivo, the PMDs may be cultured from an explant, e.g. biopsy or autopsy material, as a culture of primary cells. Methods of culturing PMDs from explants are typically specific for the type of primary cell being cultured, and are well known to one of ordinary skill in the art. As one non-limiting example, for embodiments wherein the PMDs are myocytes, exemplary methods may be found in Mitcheson, J S et al. (1998) Cardiovascular Research 39(2): 280-300 (for cardiomyocytes); Rosenblatt et al. (1995) In Vitro Cell Dev. Biol Anim 31(10):773-339 (for human skeletal muscle myocytes); Siow, RCM and Pearson, J D (2001) Methods in Molecular Medicine Angiogenesis protocols 46:237-245 (vascular smooth muscle myocytes); and Graham M, and Willey A. (2003) Methods in Molecular Medicine: Wound healing 78:417-423 (intestinal smooth muscle myocytes), the disclosures of which are incorporated herein by reference.

Subject PMDs are contacted ex vivo or in vivo with an effective amount of an agent that transiently inhibits RB activity and an effective amount of an agent that transiently inhibits ARF activity. As discussed above, an agent that transiently inhibits activity of a pocket protein family member is an agent that transiently antagonizes, inhibits or otherwise negatively regulates the pocket protein's modulation of a cell's activity; agents that transiently inhibit pocket protein activity can therefore act anywhere along a pocket protein signaling pathway as it is known in the art and described above to antagonize pocket protein signaling. Similarly, an agent that transiently inhibits the activity of ARF is an agent that transiently antagonizes, inhibits or otherwise negatively regulates the ARF modulation of cell activity; agents that inhibit pocket protein activity can therefore act anywhere along the pocket protein signaling pathway as it is known in the art and described above to antagonize pocket protein signaling By an effective amount of agent, it is an amount that will transiently reduce the overall activity of the subject pathway by at least about 25%, at least 50%, at least 60%, at least 70%, at least 80%, at least 90%, at least 95%, by about 100%, such that the cell is now able to enter mitosis and divide. In other words, the overall activity of the subject pathway will be reduced by at least about 2-fold, usually by at least about 5-fold, e.g., 10-fold, 15-fold, 20-fold, 50-fold, 100-fold or more, as compared to a control, i.e. uncontacted, cell. For agents that transiently inhibit the activity of a pocket protein, this biochemically may be realized by, for example, reducing the amount of pocket protein in the cell by about 10% or 50% or more, 70% or more, 90% or more, or up to 100%; increasing the amount of phosphorylation of the pocket protein by about 10% or 50% or more, by 70% or more, by 100% or more, by 200% or more, by 500% or more; increasing the amount of free E2F in the cell by about 10% or more, 25% or more, 50% or more, 100% or more, 200% or more, 500% or more; etc. as is well known in the art. For agents that transiently inhibit the activity of ARF, this biochemically may be realized by, for example, increasing the amount of free NDY1 in the cell by about 10% or more, 25% or more, 50% or more, 100% or more, 200% or more, 500% or more; reducing the amount of ARF in the cell by about 10% or 30% or more, 50% or more, 70% or more, about 100%; increasing the amount of free HDM2 in the cell by about 10% or more, 25% or more, 50% or more, 100% or more, 200% or more, 500% or more; etc. as is well known in the art. By transiently, it is meant that the inhibition is for a limited period of time. In transiently inhibiting a target pathway, an effective amount of agent will antagonize its target pathway for about 12 hours, about 1 day, about 2 days, about 3 days, about 5 days, about 7 days, about 10 days, about 15 days, about 20 days, or about 30 days. Antagonism of the target pathway may cease either naturally, e.g. because the agent is degraded, naturally inactivated over time, removed from the body of a subject by the blood, etc. or it may be actively shut off, e.g. by providing additional agents that inhibit expression or activity of the subject agent.

Agents suitable for transiently inhibiting pocket protein activity and ARF activity in the present invention include small molecule compounds. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in "The Pharmacological Basis of Therapeutics" (Goodman and Gilman (1996) McGraw-Hill, New York, N.Y., Ninth edition). Also included are toxins, and biological and chemical warfare agents, for example see Somani, S. M. (Ed.), "Chemical Warfare Agents," Academic Press, New York, 1992. Small molecule compounds can be provided directly to the medium in which the cells are being cultured, for example as a solution in DMSO or other solvent.

Agents suitable for transiently inhibiting pocket protein activity and ARF activity in the present invention also include nucleic acid molecules that inhibit the synthesis of pocket proteins, ARF proteins, and/or other proteins of the pocket protein or ARF pathways, respectively, for example, nucleic acids that encode antisense, siRNA, or shRNA molecules that target the RB, p107, p130 or CDKNA2/Ink4a genes and transcripts.

For example, nucleic acid agents of interest include antisense oligonucleotides (ODN), particularly synthetic ODN having chemical modifications from native nucleic acids, or nucleic acid constructs that express such antisense molecules as RNA. The antisense sequence is complementary to the targeted coding sequence, and inhibits its expression. Antisense molecules may be produced by expression of all or a part of the target coding sequence in an appropriate vector, where the transcriptional initiation is oriented such that an antisense strand is produced as an RNA molecule. Alternatively, the antisense oligonucleotide is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like. Antisense oligonucleotides may be chemically synthesized by methods known in the art. Preferred oligonucleotides are chemically modified from the native phosphodiester structure, in order to increase their intracellular stability and binding affinity. A number of such modifications that alter the chemistry of the backbone, sugars or heterocyclic bases have been described in the literature. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha-anomer of deoxyribose may be used, where the base is inverted with respect to the natural beta-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively. One or a combination of antisense oligonucleotides may be administered, where a combination may comprise multiple different sequences.

As another example, nucleic acid agents of interest include RNA agents that inhibit the synthesis of pocket proteins, ARF protein, or proteins in the pathways activated by these subject proteins. By RNA agents it is meant ribonucleotide-based agents that modulate expression of target genes, i.e. RB, p107, p130, or ARF, or members of their signaling pathways, by an RNA interference mechanism. The RNA agent may be a microRNA; see, e.g. Mudhasani et al. (2008) J Cell Biol 181(7):1055-63, which teaches that miRNAs suppress the expression of ARF. The RNA agent may be an RNAi agent, e.g., a small ribonucleic acid molecule (also referred to herein as an interfering ribonucleic acid), i.e., oligoribonucleotides, that is present in duplex structures, e.g., two distinct oligoribonucleotides hybridized to each other (siRNA) or a single ribooligonucleotide that assumes a small hairpin formation to produce a duplex structure (shRNA). By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, i.e. an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. ((1987) Biochem. Int. 14:1015); by Bhattacharyya ((1990) Nature 343:48); by Livache, et al. (U.S. Pat. No. 5,795,715); by Sambrook, et al. ((1989) Molecular Cloning: A Laboratory Manual, 2nd ed.); in Transcription and Translation ((1984) B. D. Hames, and S. J. Higgins, Eds.); in DNA Cloning, volumes I and II ((1985) D. N. Glover, Ed.); and in Oligonucleotide Synthesis ((1984) M. J. Gait, Ed.), each of which is incorporated herein by reference in its entirety. Single-stranded RNA (ssRNA) can also be produced using a combination of enzymatic and organic synthesis or by total organic synthesis. The use of synthetic chemical methods enable one to introduce desired modified nucleotides or nucleotide analogs into the dsRNA or ssRNA. For example, small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing target genes in vivo, chemically modified, cholesterol-conjugated single-stranded RNA analogues complementary to sequence in target genes may be synthesized using standard solid phase oligonucleotide synthesis protocols. The RNAs are conjugated to cholesterol, and may further have a phosphorothioate backbone at one or more positions. RNA inhibitory agents may be provided at a final concentration of about 50 nM-500 nM, more usually 100 nM-200 nM.

In certain embodiments, the RNA agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Agents suitable for transiently inhibiting the pocket protein activity and ARF activity in the present invention also include polypeptides, e.g. dominant negative peptides, or peptides of targets of the pocket proteins or ARF that are normally antagonized by pocket protein or ARF activity as is understood in the art. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

To promote delivery of the polypeptide to the intracellular domain of the cell, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

Agents suitable for transiently inhibiting pocket protein activity and ARF activity in the present invention also include nucleic acids that encode the aforementioned polypeptides that antagonize pocket protein activity and ARF activity. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the subject post-mitotic differentiated cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the subject post-mitotic differentiated cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing nucleic acid of interest to the subject cells will typically comprise suitable promoters for driving the transient expression, that is, transient transcriptional activation, of the nucleic acid of interest. These will typically be inducible promoters, such as promoters that respond to the presence of drugs such as tetracycline. By transcriptional activation, it is intended that transcription will be increased above basal levels in the target cell by at least about 10 fold, by at least about 100 fold, more usually by at least about 1000 fold.

One or more agents that transiently inhibit the activity of one or more pocket proteins may be used. Likewise, one or more agents that transiently inhibit the activity of ARF may be used. The agent(s) may be provided to the subject post-mitotic differentiated cells individually or as a single composition, that is, as a premixed composition, of agents. When provided individually, the agents may be added to the subject post-mitotic differentiated cells simultaneously or sequentially at different times. For example, the agent(s) that transiently inhibits the activity of the pocket protein(s) may be provided first, and the agent(s) that transiently inhibits the activity of ARF is provided second, e.g. 24 hours later.

In some embodiments, additional agents that promote mitosis may be provided to the cell at the contacting step, e.g. growth factors, e.g. bFGF, EGF, BMP, neuregulin, periostin, etc. In some embodiments, agents that promote cell cycle reentry are also provided to the cell in the contacting step. For example, in embodiments in which the subject post-mitotic differentiated cell is a skeletal muscle myocyte, agents that disrupt microtubules such a myoseverin peptide (Rosania G R et al. (2000) Nat. Biotechnol. 18(3):304-8) or a small molecule as is known in the art (see, e.g., Duckmanton A, (2005) Chem. Biol. 12(10):1117-26, the disclosure of which is incorporated herein by reference) may be provided to fragment the multinucleated skeletal muscle cell. Such agents are typically used when the subject post-mitotic differentiated cell has a morphologically complex phenotype, for example, a cytoskeletal architecture that polarizes the cell, such as the architecture of a multinucleated muscle cell, neuron, hepatocyte, etc.

In embodiments in which the PMDs are induced to become RCCs and divide in vivo, i.e. in situ, agents are administered locally, that is, directly to the target site in a subject, i.e. the tissue. The agents may be provided in any number of ways that are known in the art, e.g. as a liquid (e.g. in any suitable buffer (saline, PBS, DMEM, Iscove's media, etc.)), as a paste, in a matrix support, conjugated to a solid support (e.g. a bead, a filter such as a mesh filter, a membrane, a thread, etc), etc. The conditions in the tissue are typically permissive of dedifferentiation and division of PMDs, and no alteration of the basal conditions is required with the exception of providing the agents as described above.

In embodiments in which the PMDs are induced to become RCCs and divide ex vivo, the cells are contacted with the agents for about 30 minutes to about 24 hours, e.g., 1 hour, 1.5 hours, 2 hours, 3 hours, 4 hours, 6 hours, 8 hours, 12 hours, 18 hours, 20 hours, or any other period from about 30 minutes to about 24 hours in a culture media that is typically used to promote proliferation of progenitor cells of the subject lineage as is known in the art. For example, in embodiments in which the post-mitotic differentiated cell is a myocyte, the agents may be provided in DMEM LG+F10 media that has been supplemented with high levels of serum, e.g. 15%-20% FBS, 1% Pen-Strep, and 1.25-2.5 ng/mL bFGF. In some embodiments, the cells are contacted with agent repeatedly, e.g. with a frequency of about every day to about every 4 days, e.g., every 1.5 days, every 2 days, every 3 days, every 4 days, or any other frequency from about every day to about every four days with the agent. For example, agents may be provided to the subject cells once, and the cells allowed to incubate with the agent for 16-24 hours, after which time the media is replaced with fresh media and the cells are cultured further, or the agents may be provided to the subject cells twice, with two 16-24 hour incubations with the agent following each provision, after which the media is replaced with fresh media and the cells are cultured further.

Transient inhibition of one or more pocket proteins and ARF will transiently induce the subject PMDs to become RCCs and divide. By transiently induced, it is meant that the PMDs are induced to undergo mitosis for a limited amount of time, i.e. 12 hours, 1 day, 2 days, 3 days, 5 days, or 7 days. Accordingly, the subject PMDs and their progeny may undergo 1 round of mitosis, up to 2 rounds of mitosis, up to 3 rounds, up to 4 rounds, up to 5 rounds, up to 6 rounds, or up to 10 rounds of mitosis. This is unlike tumorigenic cells, which undergo unregulated mitosis, i.e., continue to divide for an unlimited amount of time. The period of time in which the RCCs are actively dividing is known as the induction period. During the induction period, a PMD that is transiently induced to divide will give rise to a population, or cohort, of progeny that are lineage-restricted cells. In other words, a PMD may give rise to 2 or more cells, 4 or more cells, 8 or more cells, 16 or more cells, 32 or more cells, 64 or more cells, 100 or more cells, 1000 or more cells, or 10,000 or more cells. In some embodiments, multiple PMDs, i.e. a population of PMDs, are induced to divide, giving rise to a population of progeny that are lineage-restricted cells. At least about 1%, about 2%, about 5%, about 8%, more usually about 10%, about 15%, about 20%, or about 50% of contacted post-mitotic differentiated cells in a population may be induced to divide. In some embodiments, the PMD dedifferentiates in the course of becoming an RCC. In some instances, transient induction may be controlled by providing agents, e.g. Rb and/o ARF-related agents to return to cells to a post-mitotic state. Examples of such RB and/or or ARF related-agents include RB or ARF polypeptides or the cDNA encoding these polypeptides or the active domains thereof.

The progeny of these divisions are all cells of a particular lineage, i.e. lineage-restricted cells (LRCs), that lineage being the lineage of the PMD that was contacted at the outset. While the agents that inhibit the pocket protein and ARF are active, i.e. during the induction period, the LRC of the culture may be mitotic progenitor cells (MPCs) that are committed to the cell lineage of the PMD. Once the agents that inhibit the pocket protein and ARF are no longer active, i.e. following the completion of the induction period, the LRC of the culture may be post-mitotic immature cells (PMIs) that are committed to the cell lineage of the PMD. For example, in embodiments in which the post-mitotic differentiated cell(s) is a myocyte, the progeny LRC during the induction period may be myoblasts (identifiable for their expression of one of more mitotic markers as well as one or more myoblast markers such as myf5 and pax7) and the progeny LRC after the induction period may be muscle precursors (identifiable for their lack of expression of mitotic markers as well as expression of one of more markers including myogenin).

In embodiments in which the PMDs are induced to become RCCs and divide in vivo, i.e. in situ, progeny may spontaneously differentiate into PMD of the lineage, or they may be provided with agents that promote differentiation into PMD of that lineage. Likewise, in embodiments in which the PMDs are induced to become RCCs and divide ex vivo, the progeny may spontaneously differentiate into PMD of the lineage, or they may be transferred to conditions that promote differentiation into the mature population of post-mitotic differentiated cells that they are destined to become. In certain embodiments, the transferring of the cells induced to divide ex vivo to condition that promote differentiation is effected by transplanting the progeny into the tissue of a subject. Cells may be transplanted by any of a number of standard methods in the art for delivering cells to tissue, e.g. injecting them as a suspension in a suitable buffer (saline, PBS, DMEM, Iscove's media, etc.), providing them on a solid support, e.g. a bead, a filter such as a mesh filter, a membrane, etc. In certain embodiments, the transferring is effected by changing the culture media to a media that promotes the differentiation of cells of that lineage, as is known in the art. For example, in embodiments in which the post-mitotic differentiated cell is a myocyte, the LRC that is produced may be induced to differentiate in DMEM LG media that has been supplemented with low levels of serum, e.g. 2% HS, 1% Pen-Strep.

In Vitro Uses

LRCs produced by the subject methods find many uses, both in vitro and in viva For example, PMDs derived from individuals having a disease have the desired cell-specific identity and disease-related aberrant regulatory program. LRCs produced from these PMDs by the subject methods will also exhibit the disease phenotype. Thus, the propagated LRCs may serve as material for the characterization of the regulatory mechanisms that have gone awry. In addition, these cells will serve as material on which to screen therapeutic agents for their ability to ameliorate the disease phenotype. Accordingly, LRCs produced ex vivo may be used to study the regulatory networks or underlying mechanisms that lead to the disease phenotype. Likewise, LRCs from such diseases may be used to screen candidate therapeutic agents for efficacy and/or for toxicity in ameliorating the regulatory step(s) that have gone awry in the disease state.

In screening assays for biologically active agents, LRCs are produced from PMDs from an individual, e.g. an individual with a disease condition, e.g. a live individual or a cadaver, by the subject methods described above, and allowed to differentiate. The differentiated cells are then contacted with a candidate agent of interest and the effect of the candidate agent is assessed by monitoring one or more output parameters. These output parameters may be reflective of an apoptotic state, such as the amount of DNA fragmentation, the amount of cell blebbing, the amount of phosphatidylserine on the cell surface as visualized by Annexin V staining, and the like by methods described above. Alternatively or additionally, the output parameters may be reflective of the viability of the culture, e.g. the number of cells in the culture, the rate of proliferation of the culture. Alternatively or additionally, the output parameters may be reflective of the health of the cells in the culture, e.g. the length of time that the cells survive in the culture, the presence or absence of ubiquitin-related puncat in the culture, etc. Alternatively or additionally, the output parameters may be reflective of the function of the cells in the culture, e.g. the cytokines and chemokines produced by the cells, the rate of chemotaxis of the cells, the cytotoxic activity of the cells, etc. Such parameters are well known to one of ordinary skill in the art and.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

PMDs useful for producing LRCs include any post-mitotic cell from any tissue comprising post-mitotic cells, e.g. muscle, nervous system, pancreas, liver, etc., e.g. a cardiomyocyte from an individual with a heart condition, a neuron from an individual with Alzheimer's disease, Parkinson's Disease, ALS, etc., as described above.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. In some embodiments, the cells are also contacted with an agent that suppresses DSBR, further sensitizing the cells to the apoptotic effects of the elevated numbers of DSBs.

Various methods can be utilized for quantifying the selected parameters. For example, terminal deoxynucleotidyl transferase dUTP nick end labeling (TUNEL) may be employed to measure DNA fragmentation. Flow cytometry may be employed to detect Annexin V binding to phosphatidylserine on the cell surface. BrdU labeling may be employed to detect proliferation rates. Western blots may be employed to assay cytokines and chemokines secreted into the medium. Migration assays, e.g. in Boyden chambers, may be employed to assay chemotaxis capacity. Antibody-dependent cell-mediated cytotoxicity (ADCC) assays may be employed to assay cytotoxicity of cells. Such methods would be well known to one of ordinary skill in the art.

As another example, LRCs produced ex vivo by the subject methods may be used in research, e.g to elucidate cellular mechanisms of disease. For example, LRCs produced ex vivo may be characterized to determine the mechanisms underlying the disease state and the regulatory pathways that have gone awry. As another example, the genomic DNA and/or RNA of LRCs produced ex vivo may be harvested and profiled to better understand which promoters are more active and which genes are more highly transcribed in which cell lineages and at which stages in development.

LRCs produced ex vivo by the subject methods may also be used to identify novel targets for drugs leading to drug discovery. Agents can be screened for those that modulate particular signaling pathways to better understand the roles that these signaling pathways play in the differentiation of cells of a particular lineage. Such agents may constitute new therapeutics that ameliorate the disease state.

Additionally, LRCs produced by the subject methods may be used to screen for compounds for their toxicity. For example, LRCs may be prepared from hepatocytes using the subject methods, and those LRCs differentiated into hepatocytes by the subject methods. The newly differentiated LRCs may then be used to screen drugs for toxicity. Examples of parameters indicative of cell function that may be assayed in such screens include members of the cytochrome P450 panel, or "CYP", as well known in the art.

In Vivo Uses

As another example, LRCs have the potential to contribute to the tissue from which the starting PMDs were acquired, and thus LRCs produced ex vivo or in vivo may be used for reconstituting or supplementing differentiating or differentiated cells in a recipient, that is, for regenerating tissue. For example, in embodiments of the above methods in which the subject post-mitotic differentiated cells are myocytes, transplanting lineage-restricted cells generated by ex vivo methods described above into muscle, or producing lineage-specific cells in situ in the muscle by in vivo methods described above results in the differentiation of new muscle cells in the patient. Muscle regeneration as used herein refers to the process by which new muscle fibers form from muscle progenitor cells or muscle precursor cells. A therapeutic composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis.

The survival of muscle fibers may refer to the prevention of loss of muscle fibers as evidenced by necrosis or apoptosis or the prevention of other mechanisms of muscle fiber loss. Muscles can be lost from injury, atrophy, and the like, where atrophy of muscle refers to a significant loss in muscle fiber girth.

Tissue regeneration therapy that employs the lineage-restricted cells produced by the subject methods are useful for treating subjects suffering from a wide range of diseases or disorders. For example, in embodiments in which the post-mitotic differentiated cells are myocytes, subjects suffering from muscular disorders, e.g., acute cardiac ischemia, injury due to surgery (e.g. tumor resection) or physical trauma (amputation/gunshot wound), or degenerative heart diseases such as ischemic cardiomyopathy, conduction disease, and congenital defects, etc. could especially benefit from regenerative tissue therapies that use the lineage-restricted cells of the subject method.

Particular examples of muscle disorders that could be treated with the subject cells include disorders of the heart muscle. Such disorders include, without limitation, myocardial infarction (interruption of blood supply to a part of the heart, causing heart cells to die); cardiac arrest (failure of the heart to contract effectively); heart failure (a progressive inability of the heart to supply sufficient blood flow to meet the body's needs, often but not always due to myocardial infarction or cardiac arrest); cardiac ischemia reperfusion injury (injury to a tissue due to reperfusion of the tissue with blood following an ischemic condition); cardiomyopathy (muscle weakness due to e.g. ischemia, drug or alcohol toxicity, certain infections (including Hepatitis C), and various genetic and idiopathic (i.e., unknown) causes); injury due to surgery, and degenerative heart diseases such as conduction disease and congenital defects.

Other examples of muscle disorders that could be treated with the subject cells, particularly allogeneic cells and/or genetically modified autologous cells, include muscular dystrophies such as Duchenne dystrophy and Becker muscular dystrophy. Duchenne dystrophy is an X-linked recessive disorder characterized by progressive proximal muscle weakness with destruction and regeneration of muscle fibers and replacement by connective tissue. Duchenne dystrophy is caused by a mutation at the Xp21 locus, which results in the absence of dystrophin, a protein found inside the muscle cell membrane. It affects 1 in 3000 live male births. Symptoms typically start in boys aged 3 to 7 yr. Progression is steady, and limb flexion contractures and scoliosis develop. Firm pseudohypertrophy (fatty and fibrous replacement of certain enlarged muscle groups, notably the calves) develops. Most patients are confined to a wheelchair by age 10 or 12 and die of respiratory complications by age 20. Becker muscular dystrophy is a less severe variant, also due to a mutation at the Xp21 locus. Dystrophin is reduced in quantity or in molecular weight. Patients usually remain ambulatory, and most survive into their 30s and 40s.

Other particular examples of muscle disorders that could be treated with the subject cells, particularly allogeneic cells and/or genetically modified autologous cells, include the non-dystrophic myopathies such as congenital and metabolic myopathies, including glycogen storage diseases and mitochondrial myopathies. Congenital myopathies are a heterogeneous group of disorders that cause hypotonia in infancy or weakness and delayed motor milestones later in childhood. An autosomal dominant form of nemaline myopathy is linked to chromosome 1 (tropomyosin gene), and a recessive form to chromosome 2. Other forms are caused by mutations in the gene for the ryanodine receptor (the calcium release channel of the sarcoplasmic reticulum) on chromosome 19q. Skeletal abnormalities and dysmorphic features are common. Diagnosis is made by histochemical and electron microscopic examination of a muscle sample to identify specific morphologic changes.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

Glycogen storage diseases of muscle are a group of rare autosomal recessive diseases characterized by abnormal accumulation of glycogen in skeletal muscle due to a specific biochemical defect in carbohydrate metabolism. These diseases can be mild or severe. In a severe form, acid maltase deficiency (Pompe's disease), in which 1,4-glucosidase is absent, is evident in the first year of life and is fatal by age 2. Glycogen accumulates in the heart, liver, muscles, and nerves. In a less severe form, this deficiency may produce proximal limb weakness and diaphragm involvement causing hypoventilation in adults. Myotonic discharges in paraspinal muscles are commonly seen on electromyogram, but myotonia does not occur clinically. Other enzyme deficiencies cause painful cramps after exercise, followed by myoglobinuria. The diagnosis is supported by an ischemic exercise test without an appropriate rise in serum lactate and is confirmed by demonstrating a specific enzyme abnormality.

Channelopathies are neuromuscular disorders with functional abnormalities due to distuRBance of the membrane conduction system, resulting from mutations affecting ion channels. Myotonic disorders are characterized by abnormally slow relaxation after voluntary muscle contraction due to a muscle membrane abnormality.

Myotonic dystrophy (Steinert's disease) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities. Mental retardation is common. Severely affected persons die by their early 50s.

Myotonia congenita (Thomsen's disease) is a rare autosomal dominant myotonia that usually begins in infancy. In several families, the disorder has been linked to a region on chromosome 7 containing a skeletal muscle chloride channel gene. Painless muscle stiffness is most troublesome in the hands, legs, and eyelids and improves with exercise. Weakness is usually minimal. Muscles may become hypertrophied. Diagnosis is usually established by the characteristic physical appearance, by inability to release the handgrip rapidly, and by sustained muscle contraction after direct muscle percussion.

Familial periodic paralysis is a group of rare autosomal dominant disorders characterized by episodes of flaccid paralysis with loss of deep tendon reflexes and failure of muscle to respond to electrical stimulation. The hypokalemic form is due to genetic mutation in the dihydropyridine receptor-associated calcium channel gene on chromosome 1q. The hyperkalemic form is due to mutations in the gene on chromosome 17q that encodes a subunit of the skeletal muscle sodium channel (SCN4A). Subjects suffering from muscular disorders e.g., acute cardiac ischemia, degenerative heart diseases such as ischemic cardiomyopathy, conduction disease, and congenital defects, or injury due to surgery, etc. could especially benefit from regenerative tissue therapies.

Diseases other than those of the musculature may similarly be treated by regenerative tissue therapy that employs lineage-restricted cells produced by the subject methods. For example, diseases of the central nervous system (CNS) or the peripheral nervous system (PNS) may be treated by such therapy. For example, for the treatment of Parkinson's disease, dopaminergic neurons may be transiently induced to divide, giving rise to neural progenitors (i.e. mitotic cells of the neural lineage) or neural precursors (post-mitotic cells of the neural lineage, i.e. following exit from mitosis) that may be transferred into the substantia nigra of a subject suffering from Parkinson's disease. Alternatively, the neural progenitors or neural precursors may be induced to differentiate into dopaminergic neurons ex vivo, and then transferred into the substantia nigra or striatum of a subject suffering from Parkinson's disease. Alternatively, dopaminergic neurons of the substantia nigra of a subject suffering from Parkinson's disease may be induced to transiently divide in situ. Descriptions of post-mitotic differentiated neurons, neuronal progenitor and precursor cells, and how to culture these cells are have been described in the art. Other diseases and disorders of the nervous system that may benefit from the subject methods include Alzheimer's Disease, ALS, disorders of olfactory neurons, a disorder of spinal cord neurons, a disorder of peripheral neurons, and other disorders due to injury or disease.

For the treatment of multiple sclerosis, spinal cord injury, or other disorder of the Central Nervous System in which enhancing myelination is desirable to treat the disorder, oligodendrocytes may be transiently induced to divide, giving rise to oligodendrocyte progenitors (MPCs) or oligodendrocyte precursors (PMIs), which are then transferred to a subject suffering from a demyelinating condition of the CNS, e.g. Multiple sclerosis, etc. or other condition wherein it is desirable to enhance myelination, e.g. spinal cord injury, etc., at the site where enhanced myelination is desired. Alternatively, the oligodendrocyte progenitors or oligodendrocyte precursors may be induced to differentiate into oligodendrocytes ex vivo, and then transferred into the subject suffering from the MS, spinal cord injury, etc., at the site where enhanced myelination is desired. Alternatively, oligodendrocytes of a subject suffering from the MS, spinal cord injury, etc. may be induced to transiently divide in situ at the site where enhanced myelination is desired. Descriptions of post-mitotic differentiated oligodendrocytes, oligodendrocyte progenitors, and oligodendrocyte precursors, and how to culture these cells are described in Dugas, J. et al. (2006) J. Neurosci. 26:10967-10983 and US Application No. 20090258423, the disclosures of which is incorporated herein by reference.

In other examples, pancreatic islet cell progenitor (MPC) or precursor (PMI) cells derived from post-mitotic differentiated pancreatic islet cells may be transplanted into a subject suffering from diabetes (e.g., diabetes mellitus, type 1), see e.g., Burns et al., (2006) Curr. Stem Cell Res. Ther., 2:255-266. Descriptions of post-mitotic differentiated cells of the pancreas, i.e. islet cells, the progenitor and precursor cells of that lineage, and how to culture these cells are described in U.S. Pat. No. 6,326,201, the disclosure of which is incorporated herein by reference.

Hepatic progenitor cells or post-mitotic differentiated hepatic cells derived from post-mitotic differentiated hepatic cells are transplanted into a subject suffering from a liver disease, e.g., hepatitis, cirrhosis, or liver failure.

In some instances, it will be desirable to regenerate tissue with lineage-restricted cells that were produced from post-mitotic differentiated cells of allogeneic tissue, that is, tissue from a different host, for example, where the disease conditions result from genetic defects in tissue-specific cell function. Where the dysfunction arises from conditions such as trauma, the subject cells may be isolated from autologous tissue, and used to regenerate function. Autologous cells may also be genetically modified, in order to correct disease conditions results from genetic defects. Alternatively, where the dysfunction arises from conditions such as trauma, post-mitotic differentiated cells may be transiently induced to divide in situ, giving rise to lineage-restricted cells that will differentiate and incorporate into the injured tissue.

As alluded to above, genes may be introduced into the subject lineage-restricted cells that have been produced ex vivo for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the lineage-restricted cells, e.g. electroporation, calcium precipitated DNA, fusion, transfection, lipofection, infection and the like, as discussed above. The particular manner in which the DNA is introduced is not critical to the practice of the invention.

To prove that one has genetically modified the subject lineage-restricted cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the myeloid lineages while maintaining the ability to express the introduced DNA. Various tests in vitro and in vivo may be employed to ensure that the potential of the cells to differentiate into a cell of a particular lineage has been maintained.

The lineage-restricted cells may be used as a therapy to treat disease (e.g., a genetic defect). The therapy may be directed at treating the cause of the disease; or alternatively, the therapy may be to treat the effects of the disease or condition. Lineage-restricted cells produced by the ex vivo methods above may be transferred to, or close to, an injured site in a subject, that is, delivered/administered locally; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The lineage-restricted cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

The number of administrations of treatment to a subject may vary. Introducing the lineage-restricted cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated, and can be readily determined by one of ordinary skill in the art.

The invention also provides a pharmaceutical pack or kit comprising one or more containers filled with one or more of the ingredients of the compositions of the invention, e.g. an agent that transiently inhibits the activity of a pocket protein family member and an agent that transiently inhibits the activity of ARF. Associated with such container(s) can be a notice in the form prescribed by a governmental agency regulating the manufacture, use or sale of pharmaceuticals or biological products, which notice reflects approval by the agency of manufacture, use or sale for human administration.

The following example is put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

EXAMPLE

Materials and Methods

Mice and Primary Myoblast Preparation.

Rosa26-CreER$^{T2}$ RB$^{lox/lox}$ mice bred and maintained as described in (Viatour, P., et al. (2008) Cell Stem Cell 3(4): 416-428) were crossed to mice carrying a Cre-responsive β-galactosidase reporter allele (Ventura, A., et al. (2007) Nature 445(7128): 661-665). The hind leg muscles of 6-8 weeks old genotyped offspring mice were prepared for primary myoblasts harvest as described (Rando, T. A. and Blau, H. M. (1994) The Journal of Cell Biology 125(6): 1275-1287). Primary myoblasts after harvest were selected in F10 media (Gibco) supplemented with 20% FBS (Omega scientific), 2.5 ng/mL bFGF (Promega), and 1% Pen-Strep (Gibco) for a week on collagen (Sigma) coated plates.

Cell Culture.

C2C12 mouse myoblasts were cultured at 10% $CO_2$ 37° C. in DMEM HG (Gibco) supplemented with 20% FBS+1% Pen-Strep. Myoblasts were seeded for fusion as described (Pajcini, K. V., et al. (2008) The Journal of Cell Biology 180(5): 1005-1019) under low serum conditions in DMEM supplemented with 2% HS, on collagen coated plates. DM media was replaced every 24 hrs. After primary myoblast harvest and selection, passages were counted once cells were cultured and expanded on growth media: DMEM LG+F10 media supplemented with 15% FBS, 1% Pen-Strep and 1.25 ng/mL bFGF, and plated on collagen coated plates. Primary myoblasts were seeded for fusion under low serum conditions in DMEM LG, 2% HS 1% Pen-Strep at $6 \times 10^5$ cells per 6 cm plate and for sparse, single-cell differentiation at $5 \times 10^4$ cells per 6 cm plate. Cell seeding numbers were adjusted depending on the surface area of different plating platforms from the 6 cm standards described above.

Figure 5:
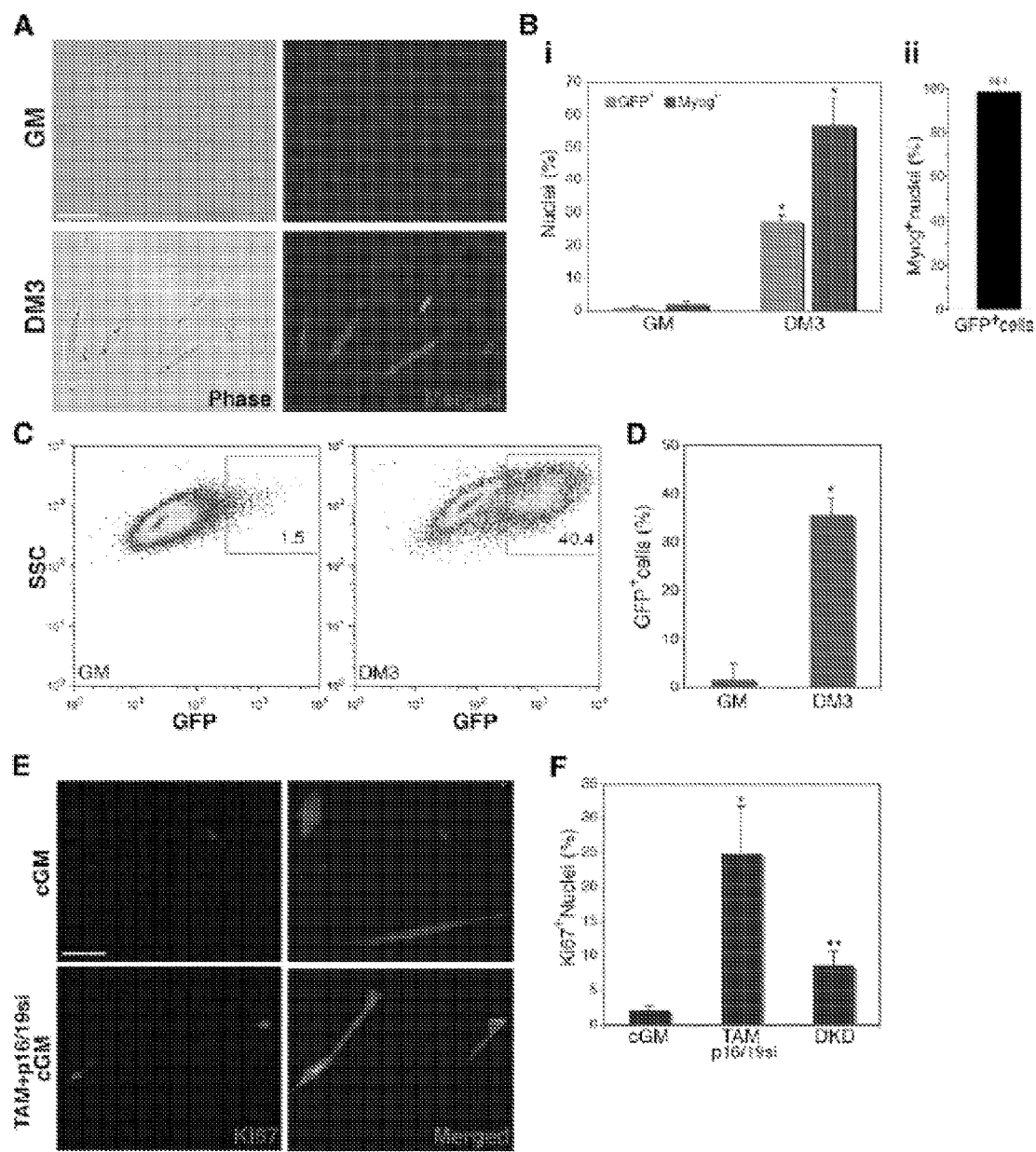

Cloning and Vector Construction.

pLE-myog3R-GFP retroviral vector was constructed by subcloning the myogenin promoter elements driving GFP expression from peGFPN1-hmyg by digestion at NotI/EcoR0109 into pLE-GFP retroviral vector backbone at XhoI/NaeI sites, after removal of CMV-GFP cassette by blunt cloning (T4 DNA pol and CIP treatment). Both forward and reverse insertion orientation were tested as described in FIG. 5, with reverse (3R) orientation showing the highest fidelity of myogenin-GFP coexpression. pMIG retrovirus vector encoding for the human RB cDNA (Sage, J., et al. (2000) Genes & development 14(23): 3037-3050) as well as all other vectors employed were transfected into ecotropic *phoenix* cells using FuGENE 6 (Roche). Cells were infected with viral supernatants containing polybrene (5 μg ml$^{-1}$) and centrifuged for 30 min at 2,000 g.

siRNA Silencing and Semi-Quantitative RT-PCR (sqRT-PCR).

RNA-interference was carried out using small-interfering RNAs (siRNAs) duplexes designed then screened for specific and effective knockdown of target genes. Duplexes employed for experiments shown in this article designed for p16/19 sense sequence AGGUGAUGAUGAUGGGCAAUU (SEQ ID NO:11) and p19ARF sense sequence GCUCUGGCUUUCGUGAACAUG (SEQ ID NO:12) or ordered directly as ON-TARGETplus siRNA RB1 (J-047474-06) from Thermo/Dharmacon. For control transfections non-targeting siRNA#1 (D-001810-01-05) and siGlo-Green were purchased from Thermo/Dharmacon. Transfections of siRNA duplexes, resuspended in siRNA buffer (Dharmacon) were carried out after differentiation of myocytes or after fusion of myotubes at 48-72 hrs in DM with silmporter transfection reagent (Millipore) as per manufacturer's instructions with final siRNA concentration at 100-200 nM. Transfection mix was added to cells after supplemented to differentiation media for 12 hrs. RNA was harvested from C2C12 or primary cells in GM or DM by RNeasy mini kit (Qiagen) and 200 ng of total RNA was used in semi-quantitative RT-PCR analysis with Superscript III One-Step RT-PCR (invitrogen). Primers designed for genes tested are listed below all sequences are in 5'-3' orientation:

```
RB set 1:
For:
GAGGAGAATTCTGTGGGCCAGGGCTGTG;    (SEQ ID NO: 13)

Rev:
GTACGAGCTCGAGCCGCTGGGAGATGTT    (SEQ ID NO: 14)
product size 1368 bp.

RB set 2:
For:
CAGGCTTGAGTTTGAAGAAATTG         (SEQ ID NO: 15)

Rev:
ATGCCCCAGAGTTCCTTCTTC           (SEQ ID NO: 16)
product size 168 bp.

p16/19:
For:
CGCCTTTTTCTTCTTAGCTTCA          (SEQ ID NO: 17)

Rev:
AGTTTCTCATGCCATTCCTTTC          (SEQ ID NO: 18)
product size 220 bp.

p19ARF:
For:
CCCACTCCAAGAGAGGGTTT            (SEQ ID NO: 19)

Rev:
AGCTATGCCCGTCGGTCT              (SEQ ID NO: 20)
product size 465 bp.

Anillin:
For:
GCGTACCAGCAACTTTACCC            (SEQ ID NO: 21)

Rev:
GGCACCAAAGCCACTAACAT            (SEQ ID NO: 22)
product size 202 bp.

AuroraB:
For:
TCGCTGTTGTTTCCCTCTCT            (SEQ ID NO: 23)

Rev:
GATCTTGAGTGCCACGATGA            (SEQ ID NO: 24)
product size 388 bp.

Survivin:
For:
CATCGCCACCTTCAAGAACT            (SEQ ID NO: 25)

Rev:
AGCTGCTCAATTGACTGACG            (SEQ ID NO: 26)
product size 360 bp.

MRF4:
For:
GGCTGGATCAGCAAGAGAAG            (SEQ ID NO: 27)

Rev:
CCTGCTGGGTGAAGAATGTT            (SEQ ID NO: 28)
product size 317 bp.

Myogenin:
For:
TCCAGTACATTGAGCGCCTA            (SEQ ID NO: 29)

Rev:
GGGCTGGGTGTTAGCCTTAT            (SEQ ID NO: 30)
product size 470 bp.

MHC:
For:
TGAGAAGGAAGCGCTGGTAT            (SEQ ID NO: 31)

Rev:
TCTGCAATCTGTTCCGTGAG            (SEQ ID NO: 32)
product size 588 bp.

M-CK:
For:
GATCTTCAAGAAGGCTGGTCAC          (SEQ ID NO: 33)

Rev:
CAATGATTGGACTTCCAGGAG           (SEQ ID NO: 34)
product size 428 bp.

GAPDH:
For:
CACTGAGCATCTCCCTCACA            (SEQ ID NO: 35)

Rev:
TGGGTGCAGCGAACTTTATT            (SEQ ID NO: 36)
product size 122 bp
```

Annealing temperature ranged from 58-62° C. and cycles from 23 (Myogenin) to 31 (p19ARF) with most products visible at 26 to 28 cycles. For RNA loading control 50 ng of total RNA was run with GAPDH primers and visualized at 22 cycles.

BrdU Analysis.

Figure 1:
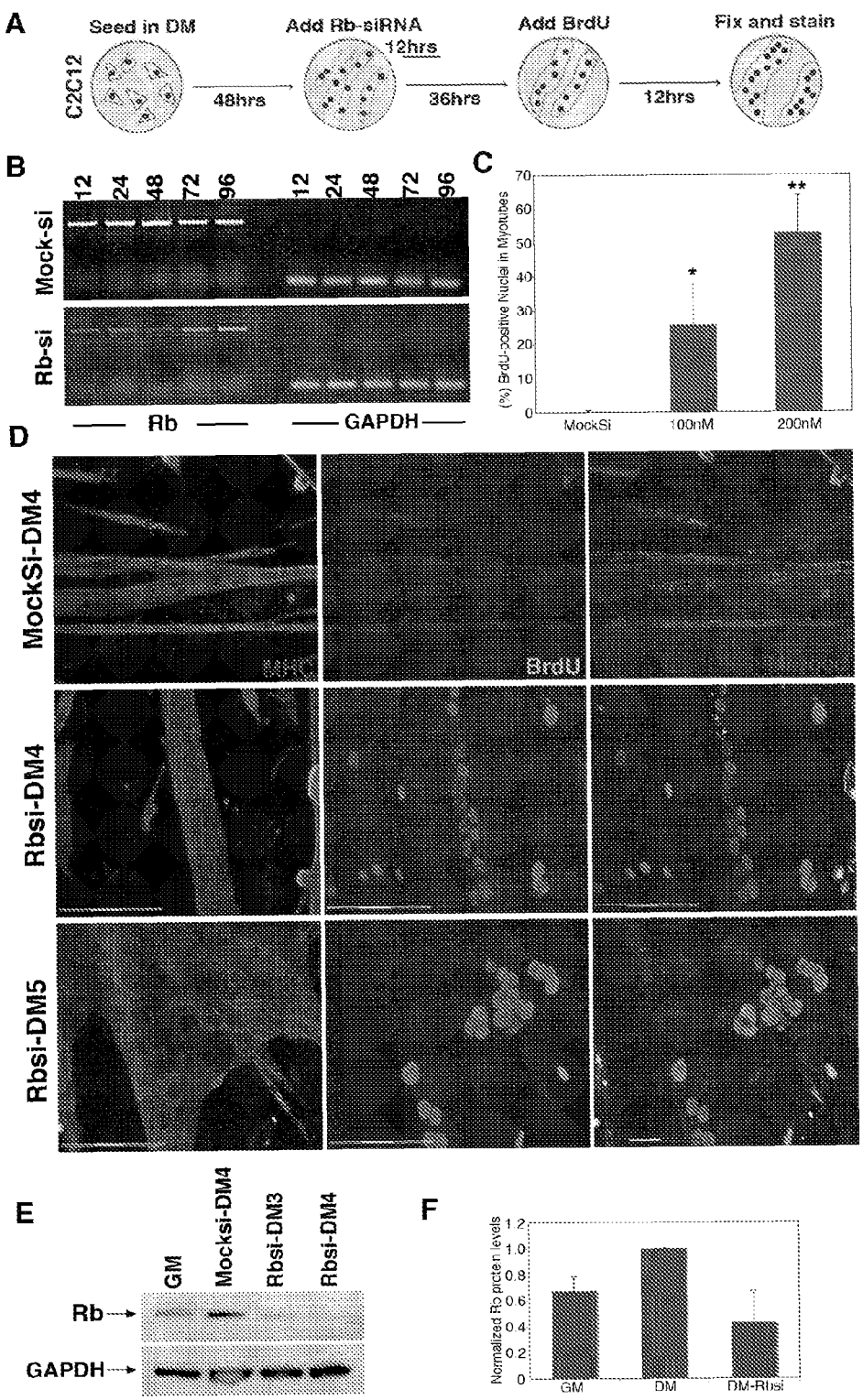
FIG. 1. Suppression of RB is sufficient for cell-cycle re-entry in C2C12 myotubes. (A) Schematic representation of the treatment of C2C12 myotubes. (B) sqRT-PCR of RB expression timecourse in hours following treatment with mocksi or RBsi. GAPDH expression shown as RNA loading control. (C) Histogram represents BrdU incorporation in myonuclei of myotubes in day 4 of differentiation (DM4), at least 36 hrs following RBsi treatment. A minimum of 500 nuclei were counted from random fields for each trial. (D) Immunofluorescence images from mock treated DM4 C2C12 myotubes and 200 nM RBsi-treated myotubes in DM4 and DM5. Myotubes were labeled with primary antibody for MHC (red) and BrdU (green), as well as with Hoechst 33258 dye (blue). Bar, 150 µm. (E) Western blot of protein expression levels of RB (100 kDa) in C2C12 myoblasts (GM), myotubes (DM4), and myotubes at DM3 and DM4, 24 hrs and 48 hrs respectively after treatment with RB-siRNA. GAPDH (35 kDa) as a loading control. (F) Histogram representing the levels of RB in GM, in DM4 and in DM4 treated with RB-siRNA for 48 hrs. Samples are normalized to protein levels of DM4 myotubes. Growth medium (GM); Myotubes cultured in differentiation medium for 4 or 5 days (DM4 or DM5 respectively). Error bars indicate the mean±SE of at least three independent experiments, P value was determined with a t test (*P<0.05, **P<0.01).
Figure 2:
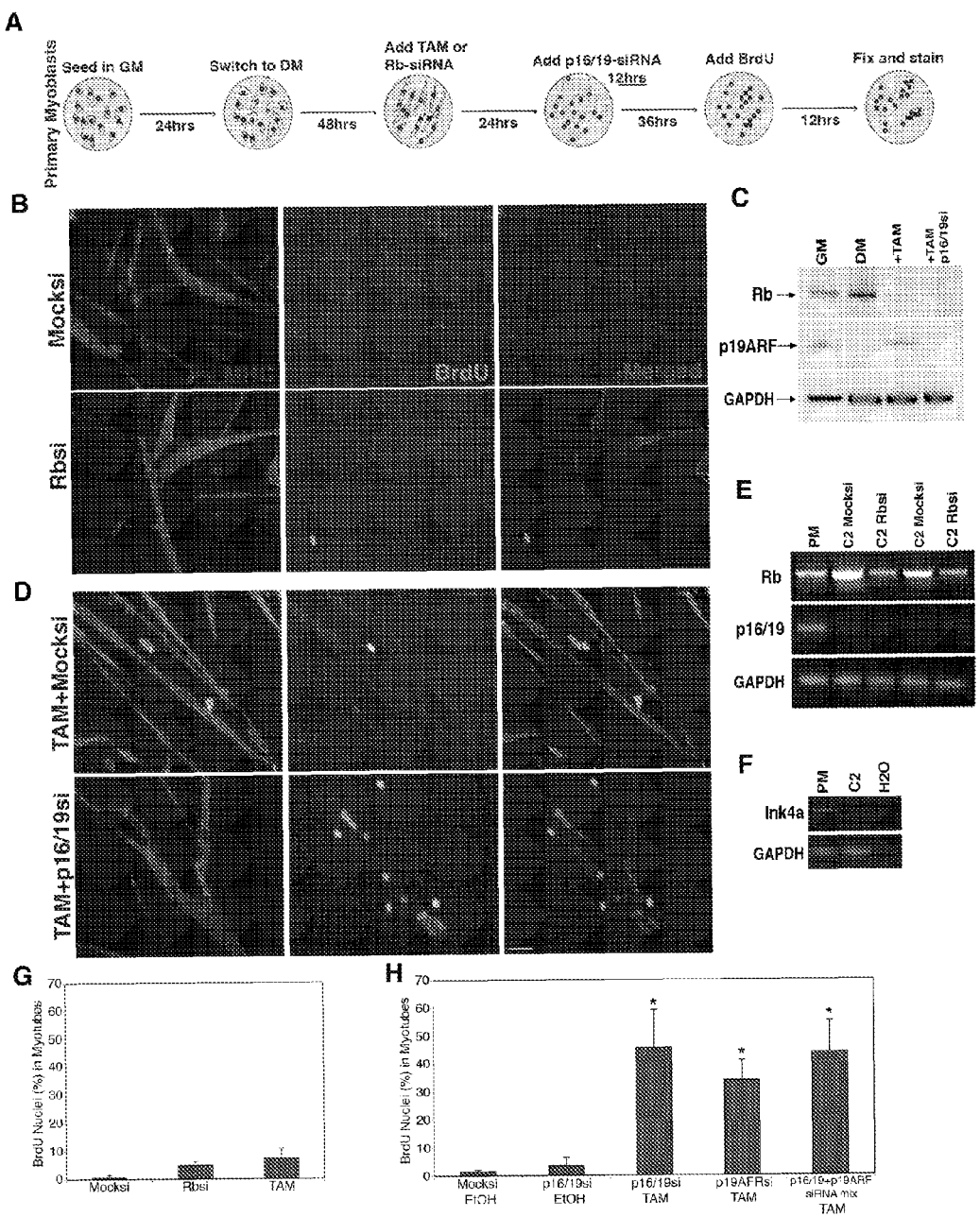
FIG. 2. Suppression of RB and p16/19 is necessary for cell-cycle re-entry in primary myotubes. (A) Schematic representation of the treatment of primary myotubes. (B) Immunofluorescence images from mock si-Glo treated primary myotubes and RBsi treated myotubes. Myotubes were labeled with primary antibody for MHC (red) and BrdU (green), as well as with Hoechst 33258 dye (blue). Bar, 50 µm. (C) Western blot of primary myotube protein levels in of RB (100 kDa) and p19ARF (20 kDa) in GM and DM5, after mock treatment, TAM treatment or TAM and p16/19si treatment. GAPDH (35 kDa) as loading control. (D) Immunofluorescence images indicating BrdU incorporation in TAM and mock si-Glo treated primary myotubes compared to TAM and p16/19si-RNA treated primary myotubes. (E) sqRT-PCR showing RB and Ink4a (p16/19) expression in primary myotubes as well as in two different C2C12 myotube populations treated with Mocksi or RBsi. (F) sq-PCR amplification using primers for the shared exon 2-3 region of the ink4a locus, from genomic DNA prepared from primary myoblasts and C2C12 myoblasts. (G) Histogram represents BrdU incorporation in primary myotube nuclei at DM5, following suppression of RB with either siRNA or TAM. (H) Histogram represents BrdU incorporation in primary myotube nuclei following treatment with TAM and siRNAs against Ink4a gene products. Growth medium (GM); Myotubes cultured in differentiation medium for 4 or 5 days (DM4 or DM5 respectively). A minimum of 500 nuclei were counted from random fields for each trial in F and G. Error bars indicate the mean±SE of at least three independent experiments. (*P<0.01).

5-bromo-2'-deoxy-uridine (BrdU) labeling and detection kit (Roche) was employed on C2C12 myotubes and primary myocytes and myotubes. BrdU labeling reagent was added to the cells with fresh DM media for 12 hrs after the treatments outlaid in each of the schemes in FIG. 1 and FIG. 2. Following labeling the cells were fixed and detected for immunofluorescence as per manufacturer's instructions, and co-stained for other proteins as described below.

Western Analysis.

Cells were lysed at room temperature in lysis buffer (50 mM Tris pH 7.5, 10 mM $MgCl_2$, 0.3 M NaCl, 2% IGEPAL). Lysates were cleared by centrifugation 5 min at 6000 rpm at 4° C., and protein quantification was determined by Bradford assay (BioRad). Immunoblotting was conducted using NuPage system from invitrogen. Samples were loaded in 10% Bis-Tris pre-cast gels, resolved by running with MES or MOPS SDS buffer, and transferred at 4° C. onto Immobilon-P membranes (Amersham). Membranes were blocked in 5% milk-PBS-T then incubated with antibodies against RB (BD) diluted 1/250 or RB (Sage lab) 1/1000; p19ARF (abcam) 1/1000; Survivin (Cytoskeleton Inc) 1/1000; AuroraB (Cytoskeleton Inc.) 1/500; MHC (Chemicon) 1/500; adult MHC (Blau lab) 1/50; M-CK (Novus) 1/500; Myogenin (BD) 1/500; and GAPDH as protein loading control diluted 1/10000 (Santa Cruz biotech). Membranes were then incubated with HRP-conjugated secondary antibodies (1/5000) (Zymed) and detected by ECL or $ECL^+$ detection reagents (Amersham). When necessary, membranes were stripped by incubating at 50° C. for 45 min and then 1 hr at RT in stripping buffer (100 mM 2-mercaptoethanol, 2% SDS, 62 mM Tris, pH7).

Immunofluorescence.

C2C12 myotubes and primary myocytes or myotubes seeded densely for fusion or sparsely for differentiation as described above were fixed and permeabilized as per manufacturer's instructions when co-staining with BrdU or with 1.5% paraformaldehyde 15 min at room temperature (RT) then permeabilized with 0.3% Triton-PBS 10 min at RT. All fixed cells were blocked with 20% goat serum for 30 min at RT or 8 hrs at 4° C. Primary antibodies for myosin heavy chain (MHC) (Chemicon) diluted 1/75 in blocking buffer or adult MHC diluted 1/20 were incubated at RT for 30 min. Primary antibodies for myogenin-RBt (Santa Cruz biotech) 1/100 or myogenin-Ms (BD) 1/250, incubated at RT for 1 hr. Primary antibodies for GFP-RBt (Invitrogen) 1/500 incubated at RT for 1 hr. Primary antibodies for survivin (Cytoskeleton Inc.) 1/250 incubated for 1 hr at RT. Primary antibodies for Ki67 (Dako) diluted 1/100 and incubated for 8 hrs at 4° C. Secondary antibodies (Invitrogen) Alexa-488 GtαMs or GtαRBt and Alexa-546 GtαMs or GtαRBt and Alexa-546 GtαRat were diluted 1/500 and incubated with appropriate primary combinations for 45 min at room temperature. When co-staining after BrdU labeling, secondary antibody for BrdU was FITC-αMs diluted 1/40 and incubated 30 min at 37° C. Nuclear staining of cells with Hoechst 33258 (Sigma) diluted 1/5000 and incubated at room temperature for 15 min. Cells were imaged with Zeiss Axioplan2 using 40× water immersion objective, Zeiss Axiovert 200M, or Zeiss Observer Z1 using NeoFluar 10× or LD Plan NeoFluar 20× objectives while ORCA-ER C4742-95; Hamamatsu Photonics, or Axiocam MRm cameras were used to capture image. Openlab 5.0.2, Velocity 3.6.1 (Improvision), and PALM Robo V4 (Zeiss) were the software used for image acquisition. Images were composed and edited in Photoshop CS (Adobe). Background was reduced using contrast adjustments and color balance was performed to enhance colors. All modifications were applied to the entire image.

FACS Sorting.

Cells were harvested from culture dishes after 0.05% trypsin treatment, centrifuged and resuspended in FACS buffer (PBS+2% GS+2 mM EDTA), and kept on ice until analysis. Cells were analyzed and sorted using a FACSVantage SE (BD Biosciences), with the DIVA analysis software. Dead cells were gated out by staining with Propidium Iodide (1 μg/ml), and cells were sorted for GFP expression at low pressure to preserve cell viability. Double sort was carried out in order to obtain a purity of 99% viable cells. In the second sort, cells were sorted directly in GM or DM as indicated and then seeded in different platforms (microwells or PALM duplex dishes).

PALM LPC.

Figure 6:
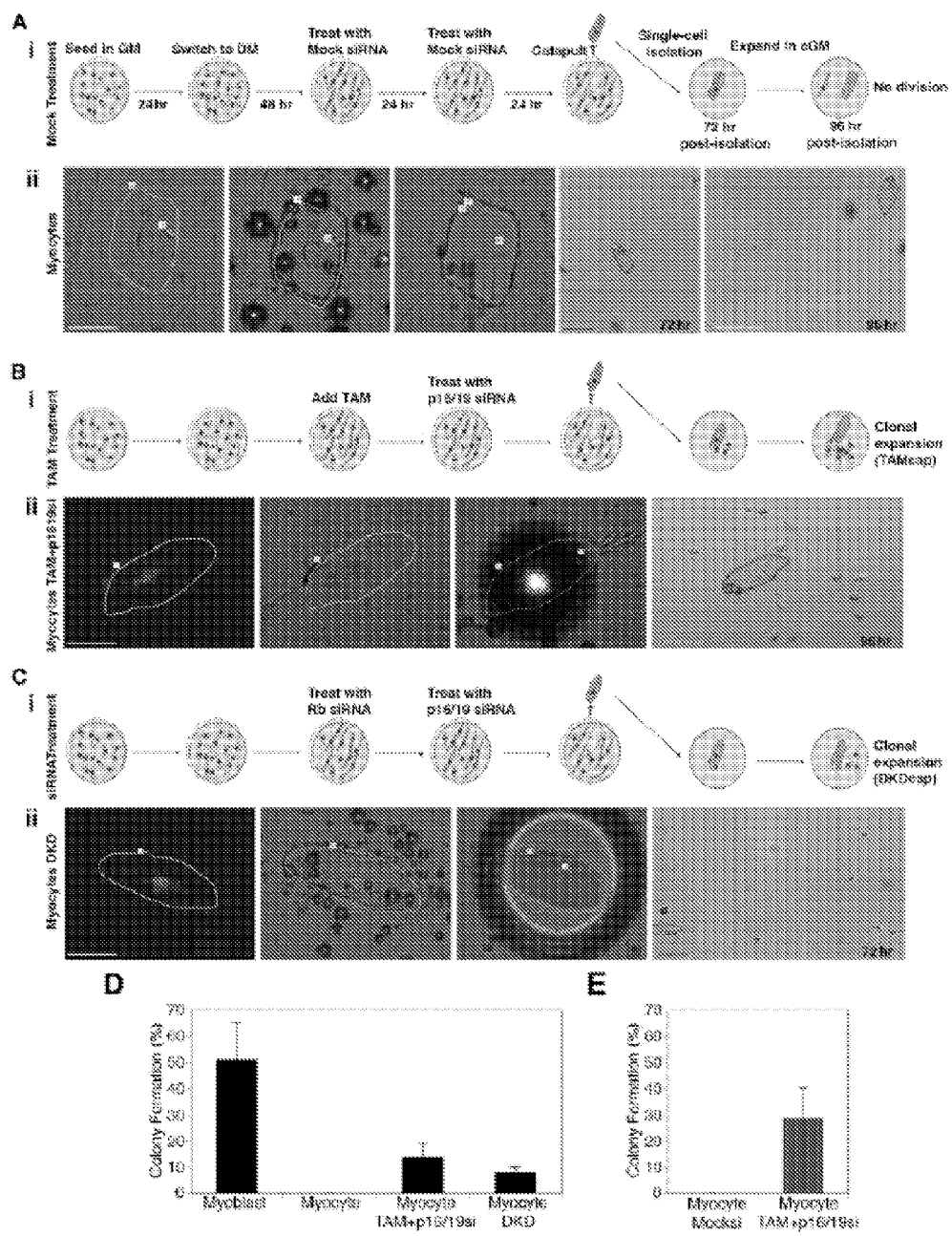
FIG. 6. (A) (i) Schematic representations of the culture conditions, treatment with mock siRNA, and isolation by laser microdissection and catapulting of myogenin-GFP+ yocytes. Diagram also shows the fate of isolated cells 72 and 96 hr after isolation. (ii) Representative images of mock-treated myocyte (DM4) (panels left to right) prior to microdissection, immediately after microdissection, after LPC isolation, 72 hr postisolation, and 96 hr postisolation. Scale bars represent 50 mm and 100 mm. (B) (i) Schematic representations of the culture conditions, treatment with TAM and p16/19 siRNA, and isolation by laser microdissection and catapulting of myogenin-GFP+ myocytes. Diagramalso shows the fate of isolated cells 72 and 96 hr after isolation. (ii) Representative image of TAM- and p16/19siRNA-treated myocyte (DM4): First panel, native GFP expression marks myogenin expression prior to microdissection; second panel, the same cell during microdissection; third panel, after LPC isolation; fourth panel, 96 hr postisolation and visualization of expansion. Scale bars represent 50 mm and 100 mm. (C) (i) Schematic representations of the culture conditions, treatment with Rb and p16/19 siRNA, and isolation by laser microdissection and catapulting of myogenin-GFP+ myocytes. Diagram also shows the fate of isolated cells 72 and 96 hr after isolation. (ii) Representative image of DKD-treated myocyte: first panel, GFP expression marks myogenin expression prior to microdissection; second panel, the same cell after microdissection; third panel, after LPC; fourth panel, 72 hr post isolation with visualization of expansion. Scale bars represent 50 mm and 200 mm. (D) Histogram represents percentage of colony formation after PALM LPC cell capture as indicated by scheme in FIG. 6A. Error bars indicate the mean±SE of at least five independent experiments, in which at least 50 myocyte membranes were captured for each trial, and at least 20 myoblast membranes were captured to verify cell capture efficiency. (E) Histogram represents percentage of colony formation after PALM LPC cell capture following FACS isolation of GFP myocyte population as indicated by the scheme in FIG. 19. Error bars indicate the mean±SE of at least four independent experiments, in which at least 50 myocyte membranes were captured for each trial. Myocytes cultured in differentiation medium for 4 days (DM4).

Primary myoblasts were sparsely seeded for differentiation in 50 mm or 35 mm laminin (Roche) coated Duplexdishes (Zeiss). 72-96 hrs after DM switch and upon verification of GFP expression by direct native fluorescence, myocytes were treated as described in FIG. 6. Duplex dishes were equilibrated by allowing media to flow in between the membrane layers via permeabilization of the top PEN membrane by LPC function at least 24 hrs before cell capture. Laser ablation was carried out after stage calibration, laser focus and optical focus calibration as per manufacturer's instructions, in Zeiss Observer Z1 inverted microscope outfitted with PALM Microbeam (Zeiss). GFP-myogenin expression was verified for every myocyte selected by direct immunofluorescence with X-CITE series 120 EXFO. Ablation was carried out through 20×LD Plan-NeoFluar objective, which permits a 3-5 μm width laser track, and membranes ranging from 50 to 150 $μm^2$ in area were catapulted by LPC, burst point of which was selected to be at least 10 μm from the myocyte. Media was removed from the Duplexdish until only a film of moisture covered the plate; in 50 mm dishes, this condition can be obtained by retaining only 500 μL of media. Ablated membranes were catapulted by LPC bursts into Roboarm SingleTube Capture II receptacle (500 μL eppendorf tube cap) with 804 of media. Membrane/myocyte capture was verified after capture by direct observation of the captured receptacle. Total volume of the receptacle was transferred into 12 or 24-well collagen coated plates, where captured myocytes were cultured in conditioned growth media (cGM), which was harvested from actively dividing myoblasts and filtered through a 0.2 μm filter.

Immunocytochemistry.

10 days after injection, TA muscles were dissected and immersed in PBS/0.5% EM-grade PFA (Polysciences) for 2 h at room temperature followed by overnight immersion in PBS with 20% sucrose at 4° C. Section staining and image analysis was performed as described in Pajcini, K. V., et al. (2008) The Journal of cell biology 180(5): 1005-1019.

Timelapse Microscopy.

Primary myoblasts were seeded for fusion in 6-well collagen coated plates. After 72 hrs in DM, primary myoblasts were treated with TAM. 24 hours later, i.e. at 96 hrs in DM, one set of primary myotubes were treated with 200 nM p16/19si for 12 hrs, at which point transfection mix was washed and cells were placed in fresh DM media. 12 hrs later, primary myotubes were imaged using Zeiss Axiovert 200M equipped with timelapse apparatus CTI-Controller 3700 Digital; Tempcontrol 37-2 digital; scanning stage Incubator XL 100/135 (PECON). Frames were captured every 10 min for a total of 50 hrs, encompassing days 5 and 6 during primary myotube fusion and maturation. Images were acquired and analyzed using Volocity 3.6.1 (Improvision). Growth medium (GM); Differentiation medium (DM).

Results

Suppression of RB by siRNA Induces S-Phase Re-Entry in C2C12 Myotubes.

Figure 9:
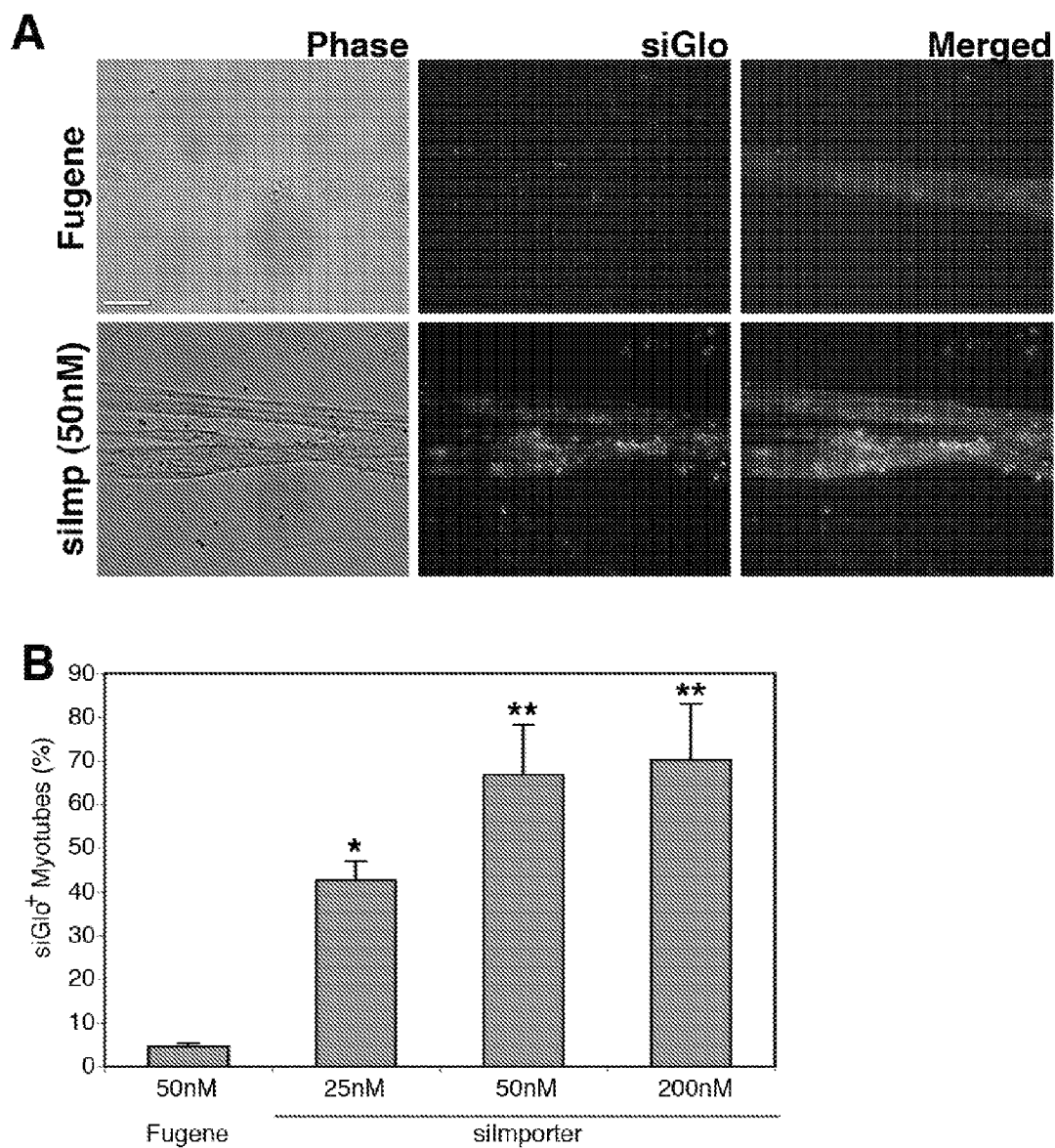
FIG. 9. silmporter myotube transfection efficiency. (A) Representative images of DM5 C2C12 myotubes transfected with siGlo-Green (non-specific siRNA dulplex conjugated to alexa-488 molecule) and either Fugene (top) or silmporter (bottom). Myotubes labeled for MHC (red) and Hoechst 33258 (blue). Bar 50 µm. (B) Quantification of transfection efficiency of siGlo-Green (100 nM) with Fugene, or varying siGlo-Green concentrations with silmporter. Myotubes cultured in differentiation medium for 5 days (DM5). Error bars indicate the mean±SE of three independent experiments (*P<0.001, **P<0.005).

The myoblast cell line C2C12 is a model system for studying muscle differentiation in vitro. In low serum differentiation medium (DM), confluent C2C12 myoblasts exit the cell cycle and fuse with one another to form multinucleated muscle cells (myotubes), which express muscle proteins and are contractile. We developed a protocol to transiently express siRNA molecules in more than 60% of myotubes using the silmporter reagent (FIG. 9). To determine the duration and efficiency of siRNA treatment, C2C12 myotubes were treated with siRNA-duplexes against RB (RBsi) (FIG. 1A-B). Semi-quantitative RT-PCR of RB transcript levels indicated that transient suppression of RB mRNA was strongest up to 48 hrs post-transfection, after which time RB levels began to recover, but never reached the same level of expression seen in control-siRNA (Mocksi) treated myotubes at 96 hrs. (FIG. 1B). Suppression of RB protein levels in myotubes was confirmed by western blotting. Total cell lysates were harvested from proliferating myoblasts and from differentiated myotubes treated with Mocksi or RBsi. Treatment with RBsi resulted in a gradual loss of RB protein (FIG. 1E) to 50% of the level of control RB in differentiated myotubes (FIG. 1F).

Figure 10:
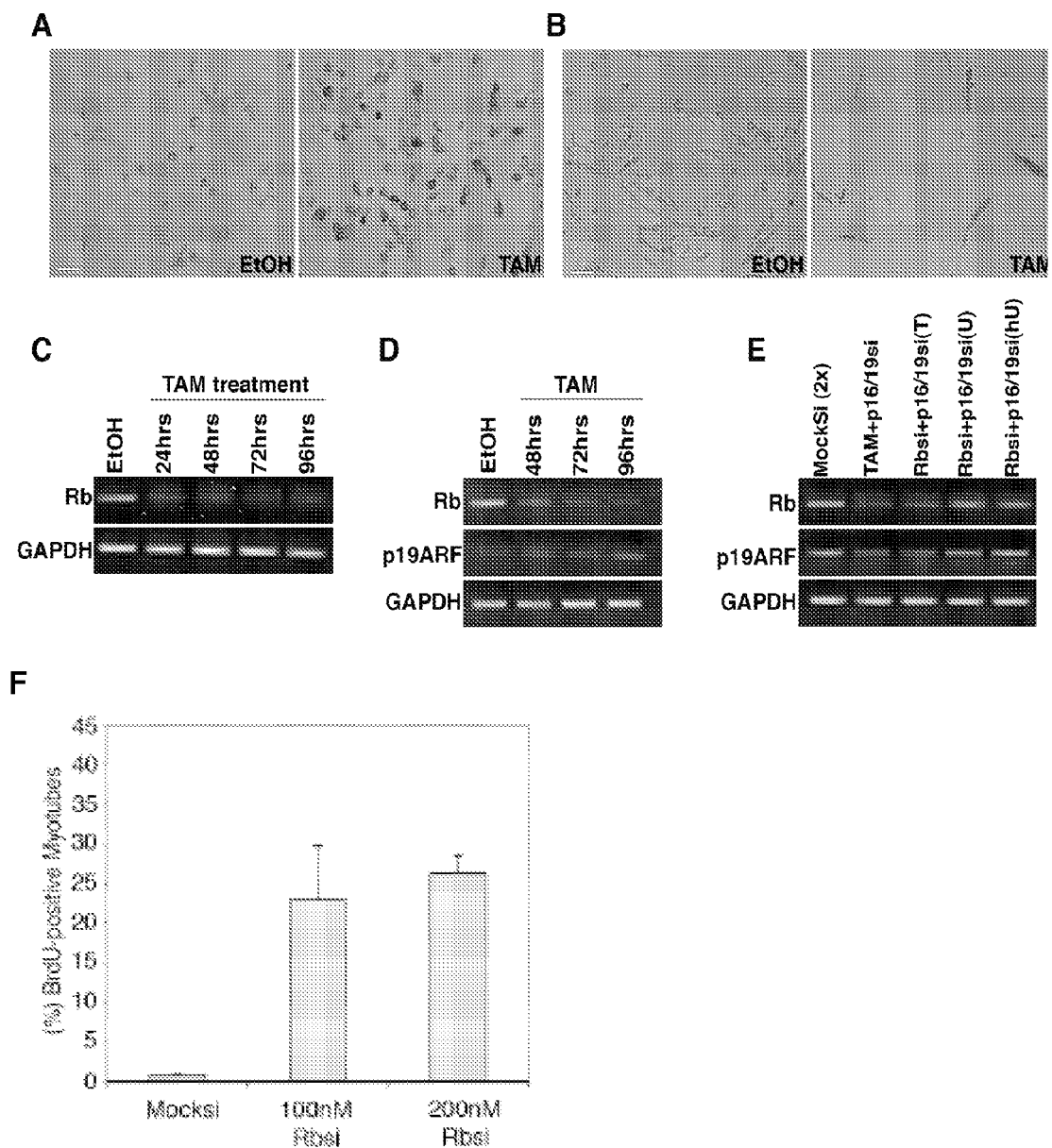
FIG. 10. Primary myoblast TAM and siRNA treatment analysis. (A) X-gal staining, indicating Cre expression of primary myoblasts in GM treated with EtOH or TAM for 24 hrs. Bar 100 µm. (B) X-gal staining, marking Cre expression of primary myotubes in DM5 treated with EtOH or TAM for 24 hrs. Bar 200 µm. (C) sqRT-PCR analysis of DM5 primary myotubes after TAM treatment. TAM was added to DM2 myotube cultures for the indicated amount time. (D) sqRT-PCR timecourse of RB and p19ARF expression in primary myotubes after 24 hr TAM treatment. (E) sqRT-PCR analysis of DKD treatment of primary myotubes with siRNA duplexes for RBsi or p16/19si, delivered in tandem (T), in unison (U) or in unison at half dose-100 nM (hU). Growth medium (GM); Myotubes cultured in differentiation medium for 4 or 5 days (DM4 or DM5 respectively). (F) the percentage of myotubes that have at least two BrdU positive myonuclei.
Figure 11:
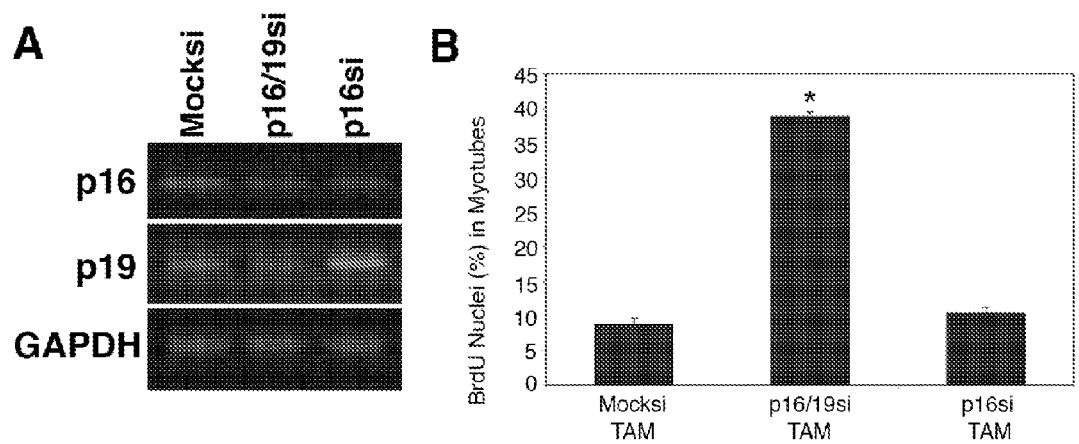
FIG. 11. Suppression of p16 alone is insufficient for S-phase re-entry in myotubes. (A) sqRT-PCR analysis of expression levels of p16, p19 and GAPDH, in TAM treated myotubes after treatment with siRNA duplexes against p16-only and p16/19. (B) Histogram represents BrdU incorporation in primary myotube nuclei following treatment with TAM and siRNAs against p16/19 or p16-only siRNA duplexes. At least 500 nuclei were counted for each trial. Error bars indicate the mean±SE of two independent experiments (*P<0.001)

To determine if S-phase re-entry in C2C12 myotubes occurred after suppression of RB, we labeled Mocksi and RBsi-treated myotubes with BrdU, as indicated in the scheme in FIG. 1A. FIG. 1D shows representative images. Myotubes were stained for myosin heavy chain (MHC) along with BrdU to enhance morphological identification and to confirm differentiation. BrdU-labeled myonuclei were observed inside MHC myotubes only after RBsi treatment (middle and lower panels). We found a marked change in myotube morphology 48 hrs after transfection of RBsi (FIG. 1D bottom panels). After suppression of RB, myotubes lost their compact elongated structure and characteristically aligned myonuclei. Cell shape no longer resembled a myotube and nuclei aggregated in clusters, many of which were BrdU-positive. S-phase re-entry was dependent on the dose of RBsi used and the percentage of BrdU myonuclei doubled from 25% to 52% as the siRNA concentration was increased from 100 to 200 nM (FIG. 10). In all of the following experiments, unless stated otherwise, the 200 nM concentration of siRNA was used. The percentage of myotubes that contained any BrdU-positive nuclei was analyzed in a separate set of experiments and found to be 25% (FIG. 10F), which is explicable because myotubes with Brdu-positive nuclei often had large clusters of nuclei that underwent DNA synthesis, probably reflecting the successful transfection of a fraction of the cells in the culture (FIG. 9A). FIG. 1F shows representative images of BrdU incorporation together with MHC immunostaining to confirm differentiation. We found a marked change in myotube morphology 72 hr after transfection of Rbsi (FIG. 1D, bottom) from a compact elongated structure with characteristic linear nuclear alignment to an amorphous structure, with nuclei aggregated in clusters, many of which were BrdU positive. These data confirm that transient suppression of RB is sufficient to induce S-phase re-entry in differentiated C2C12 myotube nuclei, and show that the extent of this effect depends on the concentration of RBsi used.

Both RB and p19ARF Must be Suppressed for S-Phase Re-Entry in Primary Myotubes.

The majority of the data that suggests that suppressing RB alone is sufficient for cell cycle re-entry in mature mammalian myotubes has been obtained in experiments using the C2C12 cell line. Although useful for studying various aspects of muscle cell differentiation and fusion, C2C12 cells, like other cell lines, have acquired mutations that permit their immortalization. Therefore, we considered it critical to use primary cells to assess the role of RB in maintaining the post-mitotic state. We harvested primary myoblasts capable of differentiation in culture, as previously described (Rando, T. A. and Blau, H. M. (1994) The Journal of Cell Biology 125(6): 1275-1287), from the hind leg muscles of Rosa26-CreER$^{T2}$RB$^{lox/lox}$ mice crossed to mice carrying a Cre-responsive β-galactosidase reporter allele. In these mice, Cre expression and RB excision is dependent on tamoxifen (TAM) induction (FIG. 10A-B). Primary myoblasts were used at low passage during which time cell shape remained compact and uniform. In primary myotube cultures a single 24 hr treatment with 1 µM TAM was sufficient to reduce RB expression (FIG. 100). A time course of RB expression indicates that both transcript and protein levels drop substantially by 96 hrs following TAM treatment (FIG. 2C and FIG. 10D).

We analyzed S-phase re-entry in primary myotube cultures after loss of RB expression by BrdU-labeling according to the scheme in FIG. 2A. By contrast to C2C12 myotubes, in primary myotubes regardless of whether RB was knocked-down by RBsi (FIG. 2B) or excised by Cre expression (FIG. 2D top panels), BrdU-labeling of myonuclei was rare (FIG. 2G). BrdU labeling in MHC myotubes was assayed in greater than 1500 nuclei in randomly selected fields. Notably, in the representative images in FIGS. 2B and 2D, BrdU$^+$ nuclei are clearly present and detectable, but these nuclei are not within MHC$^+$ myotubes as shown in merged IF images. Thus, regardless of the method of RB suppression, loss of RB in primary myotubes is not sufficient for cell cycle re-entry.

Figure 13:
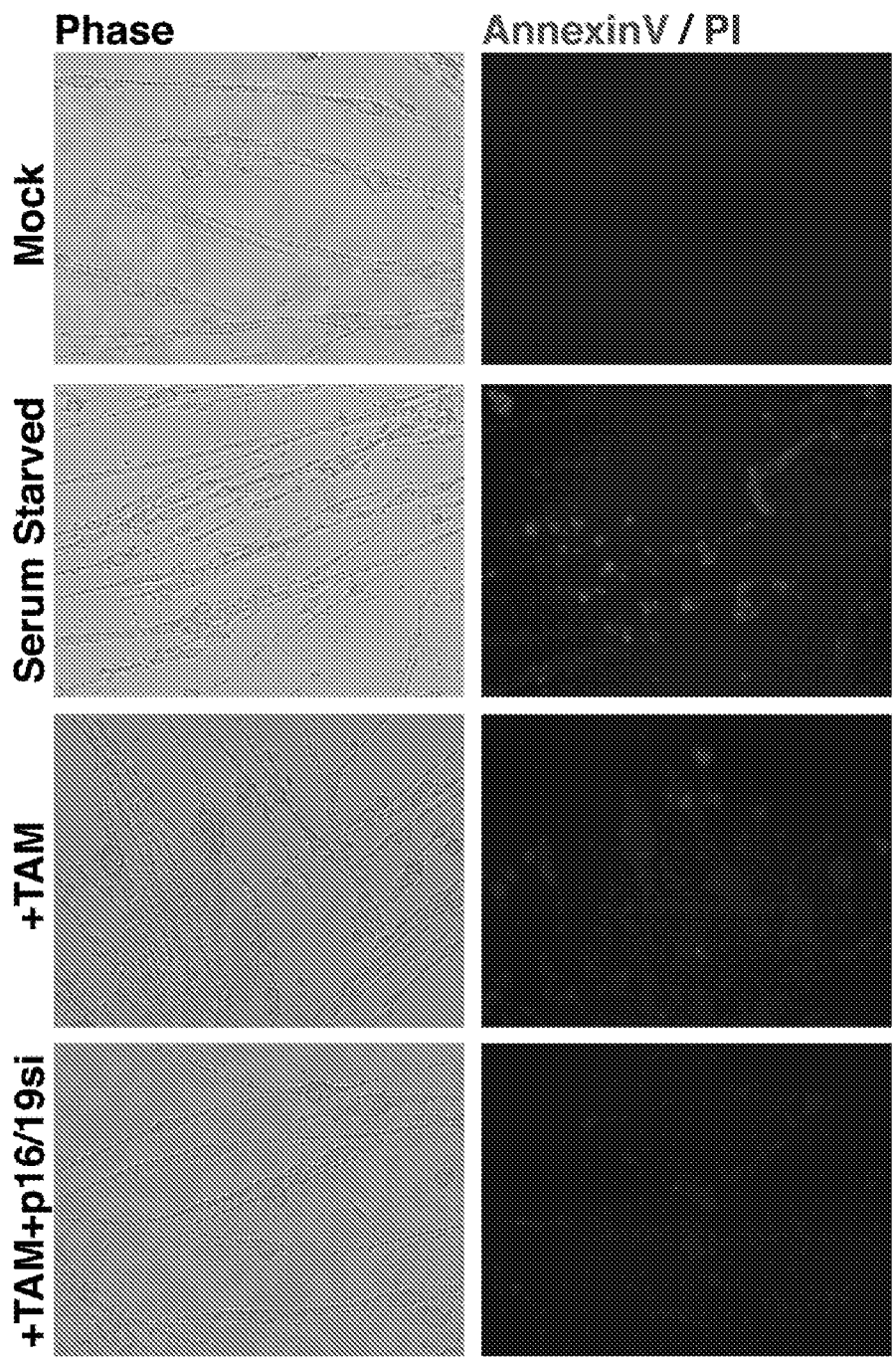
FIG. 13. Primary myotubes show minimal apoptosis after loss of Rb and p16/19. Representative immunofluorescence images of primary myotubes at day 6 during differentiation treated as indicated and labeled for AnnexinV (green) and propidium iodide (PI).
Figure 14:
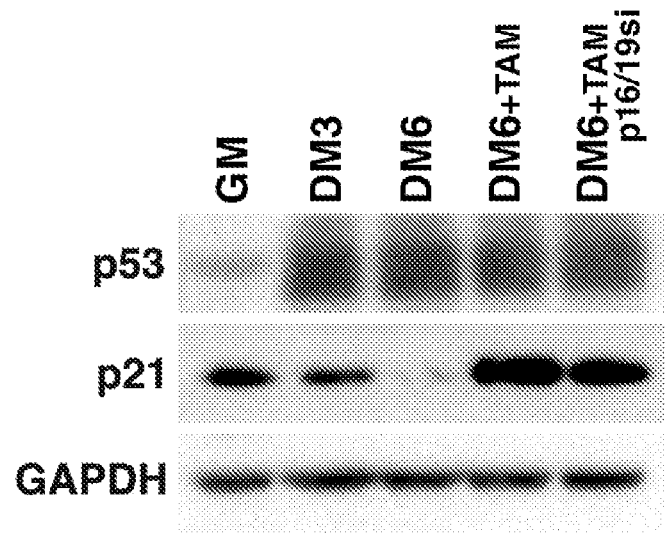
FIG. 14. Western analysis of protein levels of p53 and p21, in dividing myoblasts in growth media as well as in differentiation media at day 3 (DM3), day 6 (DM6) and DM6 treated as indicated.

Disruption of RB function by mutation or by hyperphosphorylation in response to mitogenic signals leads to the accumulation of E2F transcription factor activity, and activation of ARF (DeGregori, J., et al. (1997) Proceedings of the National Academy of Sciences USA 94(14): 7245-7250; Lowe, S. W. and Sherr, C. J. (2003) Current Opinion in Genetics & Development 13(1): 77-83). ARF, in turn, serves to block inappropriate cycling. Induction of ARF was accompanied by a mild increase in baseline levels of apoptosis, but the majority of myotubes remained robust and viable. Apoptosis was rarely observed in siRNA-treated cells in which p16/p19 was reduced (FIG. 13).

In contrast, C2C12 myotubes do not express p19ARF in response to RB suppression, as would be expected in a cell line that has bypassed cell cycle regulation by the Ink4a locus during immortalization (FIG. 2E). A genomic deletion in the shared exon 2 region of the ink4a locus was confirmed by PCR (FIG. 2F). To test whether the suppression of the Ink4a gene products in RB-deficient primary myotubes would permit cell cycle re-entry, we designed siRNA duplexes that target the shared exon 2 region of Ink4a mRNA (p16/19si), and the ARF-specific exon 1β region for knockdown of p19ARF (p19ARFsi). Primary myotubes were treated with TAM or RBsi, then 24 hrs later transfected with p16/19si, p19ARFsi or both. Loss of RB and p19ARF in myotubes was verified by western analysis (FIG. 2C). When labeled with BrdU following TAM and p16/19si treatment as described in the scheme in FIG. 2A, myonuclei incorporated BrdU in MHC-positive myotubes (FIG. 2D). Quantification of the BrdU labeling indicated that 45.7±7.2% of myonuclei enter S-phase in TAM and p16/19si treated myotubes, a marked increase over baseline values observed in myotubes treated only with TAM or p16/19si respectively (FIG. 2H). Different combinations of siRNAs that exclusively knockdown p19ARF or both Ink4a gene products in TAM treated cells did not yield significantly different results (FIG. 2H). For subsequent experiments we used the p16/19si (exon 2) because it gave the strongest suppression of p19ARF. Our data shows that robust S-phase re-entry in differentiated primary mammalian myotubes occurs only after combined suppression of both RB and p19ARF.

Upregulation of Mitotic and Cytokinetic Components in RB and p16/19-Defficient Myonuclei.

To determine if S-phase re-entry in PM myonuclei marked the initiation of the mitotic process in differentiated multinucleated myotubes, we analyzed control or TAM and p16/19si treated primary myotube nuclei for the induction of expression of mitotic and cytokinetic proteins. We investigated the expression patterns and localization of AuroraB and survivin, two important components of the chromosome passenger complex (CPC), which controls chromosome and spindle structure, kinetochore attachment and chromosome segregation. We also analyzed the mRNA expression of anillin, a structural protein important in the organization and stability of the cleavage furrow during cytokinesis.

Figure 3:
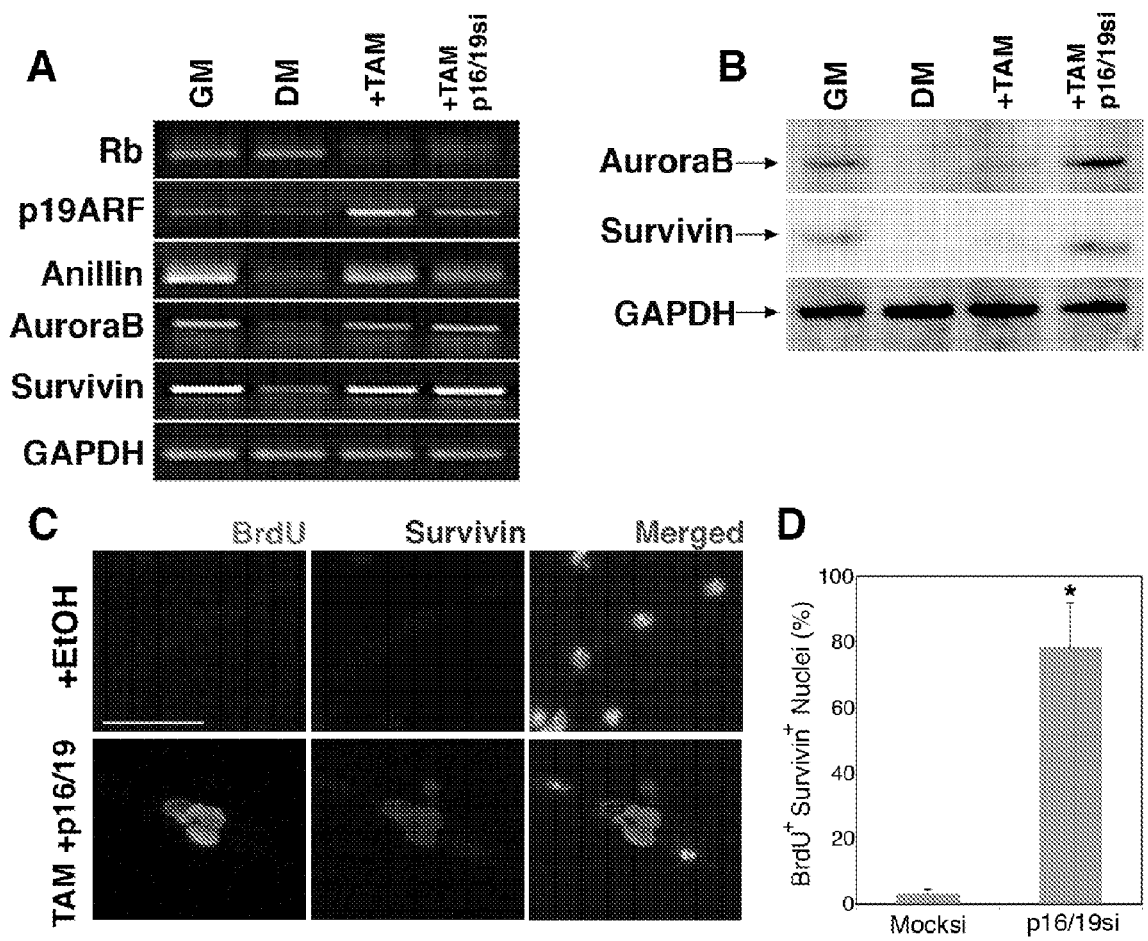
FIG. 3. Decrease in RB and p16/19 levels leads to upregulation of mitotic machinery. (A) semi-quantitative RT-PCR (sqRT-PCR) analysis of expression of Anillin, AuroraB and Survivin in GM, mock-treated DM5, in DM5 with TAM alone or with TAM and p16/19si. (B) Western blot analysis showing protein levels of AuroraB (38 kDa) and Survivin (20 kDa) following TAM treatment or TAM and p16/19si in DM5. GAPDH (35 kDa) (C) Immunofluorescence images of primary myotubes in DM5 after mock treatment, and in DM5 after treatment with TAM and p16/19-siRNA. Myotubes were labeled with primary antibody for BrdU (green), Survivin (red), as well as with Hoechst 33258 nuclear dye (blue). Bar, 50 µm. (D) Histogram represents colocalization of BrdU and Survivin in primary myotube nuclei treated with TAM and non-specific Mock-siRNA duplexes as compared to myotubes treated TAM and p16/19-siRNA duplexes. Growth medium (GM); Myotubes cultured in differentiation medium for 4 or 5 days (DM4 or DM5 respectively). A minimum of 500 nuclei were counted from random fields for each trial. Error bars indicate the mean±SE of at least three independent experiments. (*P<0.005)
Figure 12:
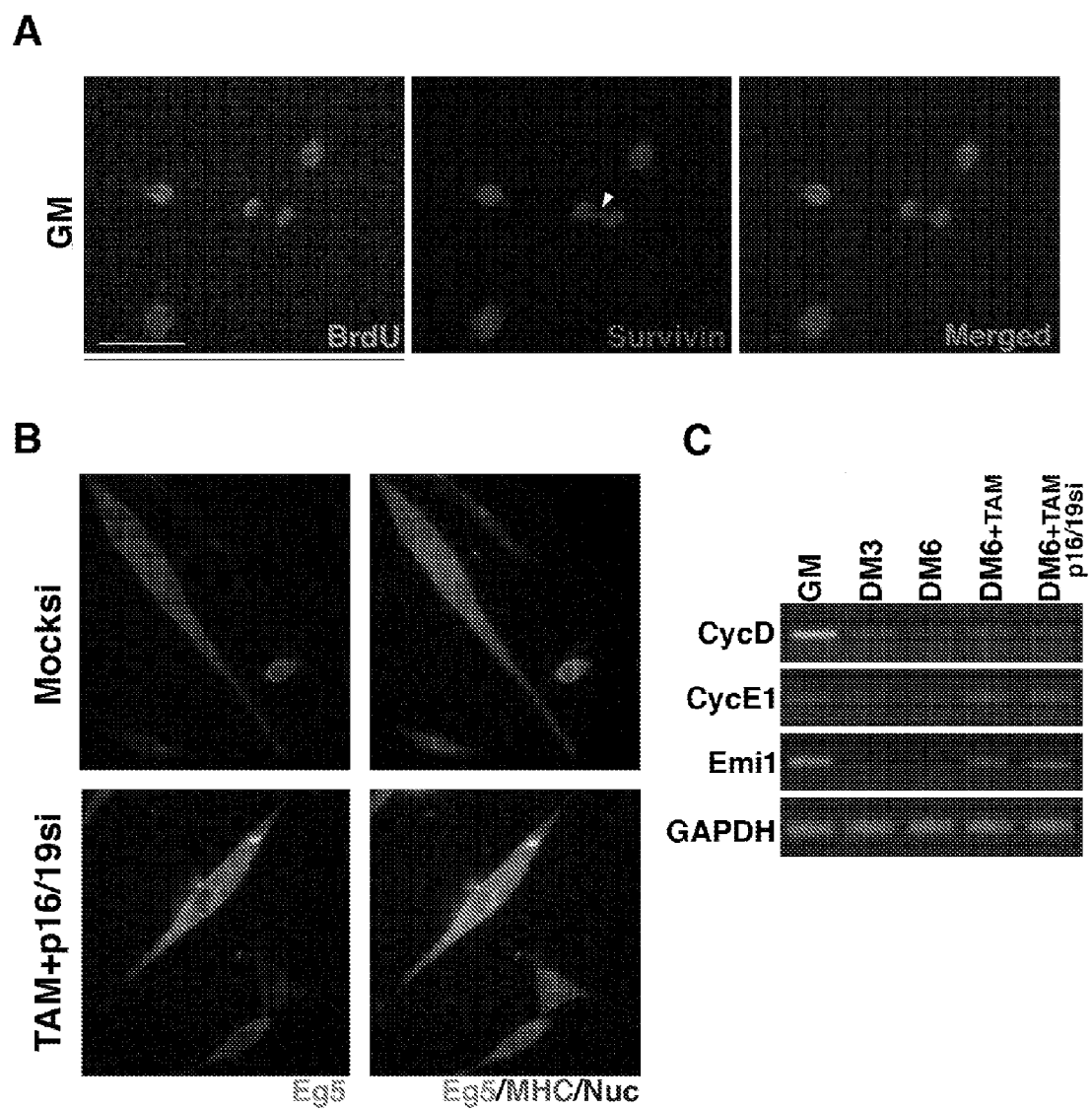
FIG. 12. Upregulation of mitotic machinery after suppression of Rb and Ink4a gene products. (A) Survivin and BrdU co-localization in myoblasts. Immunofluorescence images of primary myoblasts in Growth medium (GM) stained for BrdU (green) Survivin (red) and nuclear dye Hoechst 33258. (B) Immunofluorescence images of primary myotubes treated with non-specific siRNA duplexes (Mocksi) or TAM and p16/19si. Myotubes labeled for Eg5 (green), MHC (red) and Hoechst 33258 (blue). (C) sqRT-PCR analysis of expression levels of cyclins D and E1 as well as Emi1/FBOX5, in primary myoblasts in GM, DM and in DM treated as indicated.

Anillin and each of the CPC components mentioned above are actively expressed in primary proliferating mononucleated myoblasts, but their mRNA and protein levels drop precipitously once myotubes form (FIG. 3A-B). Once RB was excised in differentiated primary multinucleated myotubes after TAM-treatment, anillin, AuroraB and survivin mRNA levels all rose, despite high levels of p19ARF expression (FIG. 3A). However, protein levels for AuroraB and survivin attain levels comparable to those of growing myoblasts only after concomitant suppression of RB and p19ARF (FIG. 3B). To verify that upregulation of CPC components occurred specifically in myonuclei that had entered S-phase, primary myoblasts were labeled with BrdU for 12 hrs then fixed and stained for BrdU and survivin. Dividing primary myoblasts in growth medium are positive for both BrdU and survivin, with the latter marking the cleavage furrow between two dividing cells (FIG. 12 arrowhead). Differentiated, control-treated myotubes do not have myonuclei that express survivin, but those treated with TAM and p16/19si exhibit clustered BrdU$^+$ myonuclei, and it is these same myonuclei that upregulate survivin expression (FIG. 3C bottom panels). Quantification of the staining results indicated that nearly 80% of the myonuclei that had re-entered S-phase also upregulated survivin (FIG. 3D). In the vast majority of BrdU$^+$ myonuclei, survivin staining did not localize in the cleavage furrow or to any particular nuclear compartment, but was diffusely distributed throughout the nucleus. Taken together, our data show that in primary multinucleated myotubes deficient in both RB and ARF, DNA synthesis is followed by upregulation of proteins involved in chromosome segregation and cytokinesis.

Dedifferentiation Accompanies S-Phase Re-Entry in Primary Muscle Cells.

Differentiated muscle cells exhibit characteristic changes in expression of phenotypic markers such as MHC and creatine kinase (M-CK) that accompany the profound changes observed in their morphology and post-mitotic state; see, for example, Charge, S. B. and Rudnicki, M. A. (2004) Physiological Reviews 84(1): 209-238. We investigated the role of the RB and Ink4a gene products in sustaining expression of the differentiated phenotype by analyzing morphology and expression of markers of differentiation. In primary myoblasts in kept in growth medium or undergoing differentiation (DM), the cellular morphology and expression of MHC were analyzed at various time points, with or without deletion of RB and with or without suppression of p16/19. The data show that over time, cells which are treated with TAM first undergo formation of mature myotubes with strong expression of MHC, followed at later time points by a strong decrease in MHC expression after loss of expression of RB, but only if ARF is also suppressed (FIG. 4A). In cells treated only with TAM, not only does the morphology remain similar to control myotubes, but MHC staining remains strong (FIG. 4A).

Figure 4:
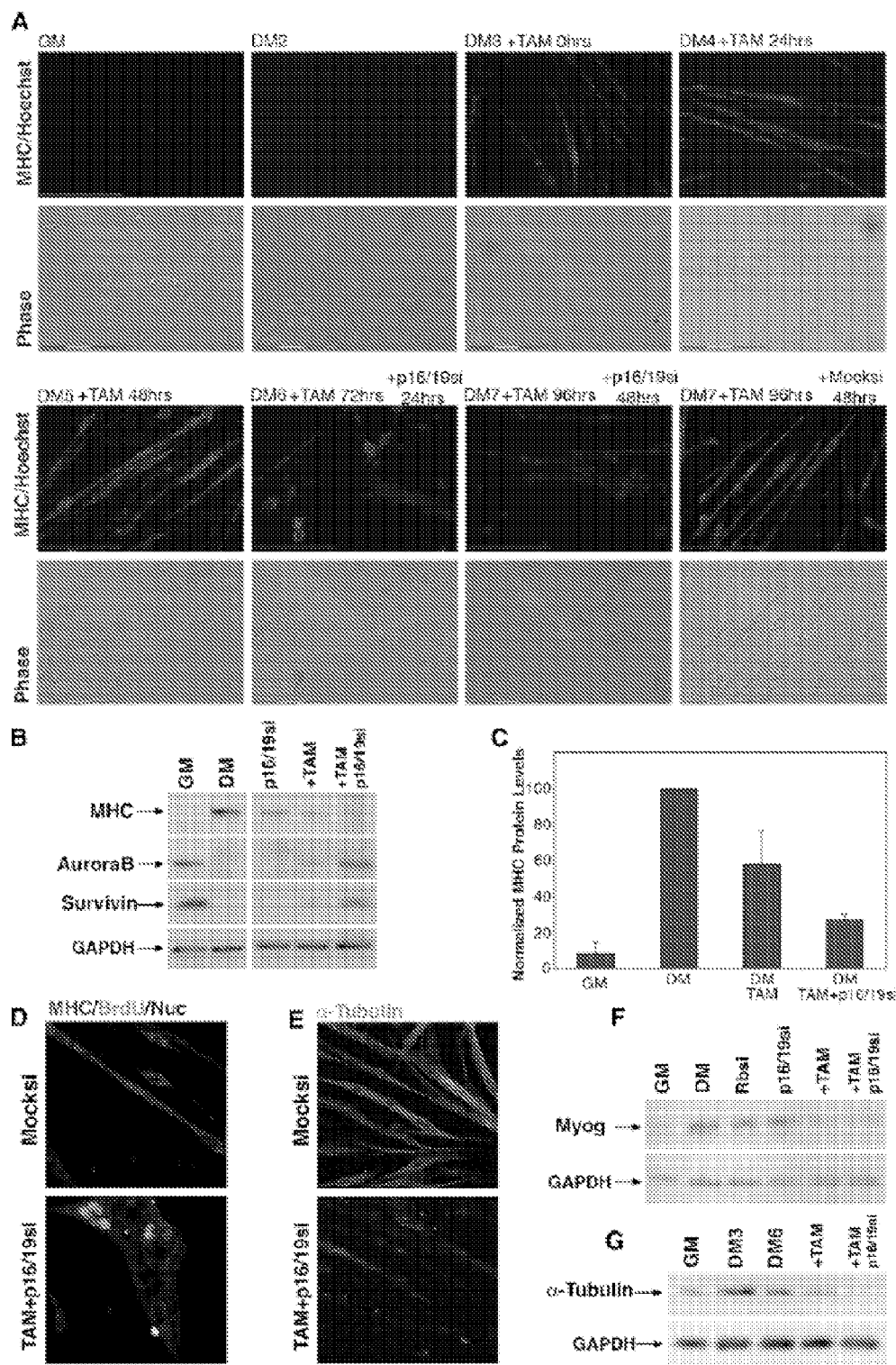
FIG. 4. Dedifferentiation of mature myotubes. (A) Immunofluorescence images of primary myoblasts and myotubes cultured for indicated times in DM and treated with TAM and either non-specific siRNA (Mocksi) duplexes or p16/19si at the indicated time points. Myotubes labeled with primary antibodies for MHC (red), BrdU (green), and Hoechst 33258 (blue). Bottom panels phase images of the same time points. Bar, 150 µm. (B) Western blot analysis of primary myoblasts (GM) and DM5 PM showing expression of MHC (220 kDa), AuroraB (38 kDa) and Survivin (20 kDa) as well as expression of these same proteins after myotube treatment with siRNA duplexes against p16/19, with TAM or TAM and p16/19. (C) MHC protein levels normalized to differentiated myotube cultures. Primary muscle cells were treated with TAM or TAM and p16/19si Growth medium (GM), Differentiation medium (DM). (D) Immunofluorescence images of DM6 primary myotubes treated with EtOH and non-specific siRNA duplexes or TAM and p16/19si for at least 48 hrs. Myotubes labeled with primary antibodies for MHC (red), BrdU (green), and Hoechst 33258 (blue). Growth medium (GM); Myotubes cultured in differentiation medium for 4 or 5 days (DM4 or DM5 respectively). (E) Immunofluorescence images of DM6 primary myotubes treated with non-specific siRNA duplexes or TAM and p16/19si for at least 48 hrs. Myotubes labeled with primary antibodies for alpha-tubulin (green) and Hoechst 33258 nuclear stain (blue). (F, G) Western blot analysis of Myogenin (36 kDa) (F) and alpha tubulin (50 kDa) (G) in primary myoblasts (GM) and DM6 (myogenin) on indicated days (tubulin) treated as indicated with siRNA duplexes and/or TAM. In each of the blots, GAPDH (35 kDa) is the loading control FIG. 5. Myogenin-expressing myocytes can enter S-phase only after loss of RB and Ink4a genes. (A) Immunofluorescence images of myoblasts (GM) and myocytes (DM3) infected pLE-myog3R-GFP. Cells were labeled with primary antibodies for GFP (green), myogenin (red) and Hoechst 33258 (blue). Bar 50 µm. (B.) (i) Histogram represents percentage of GFP-positive and myogenin-positive cells in myoblasts (GM) or myocytes (DM3). A minimum of 1000 nuclei were counted from random fields for each trial. Error bars indicate the mean±SE of at least three independent experiments. (*P<0.005). (ii) Histogram represents percentage of GFP-positive cells that also express myogenin. Individual cells were evaluated for expression of each marker. A minimum of 250 cells were counted from random fields. Error bars indicate the mean±SE of three independent experiments. (C) Representative FACS plots of myoblasts (GM) and myocytes (DM3) infected with retroviral pLE-myog3R-GFP construct. Gated population indicates GFP-positive myocyte population employed in subsequent experiments. (D) Histogram representation of GPF expression in three independent experimental FACS profiles on myoblasts (GM) and myocytes (DM3) (*P<0.001). (E) Immunofluorescence images of GFP-positive FACS-sorted myocytes cultured in conditioned GM only or in cGM with TAM and p16/19si-RNA. Cells labeled for Ki67 (red) and GFP (green) as well as Hoechst 33258 (blue). Bar 50 µm. (F) Histogram represents percent of Ki67-positive nuclei in GFP-positive FACS sorted population, in cGM, treated with TAM and p16/19si, or treated with RBsi and p16/19si duplexes in tandem (DKD). Growth medium (GM). A minimum of 100 nuclei were counted from random fields for each trial. Error bars indicate the mean±SE of three independent experiments. (*P<0.01, **P<0.005).
Figure 15:
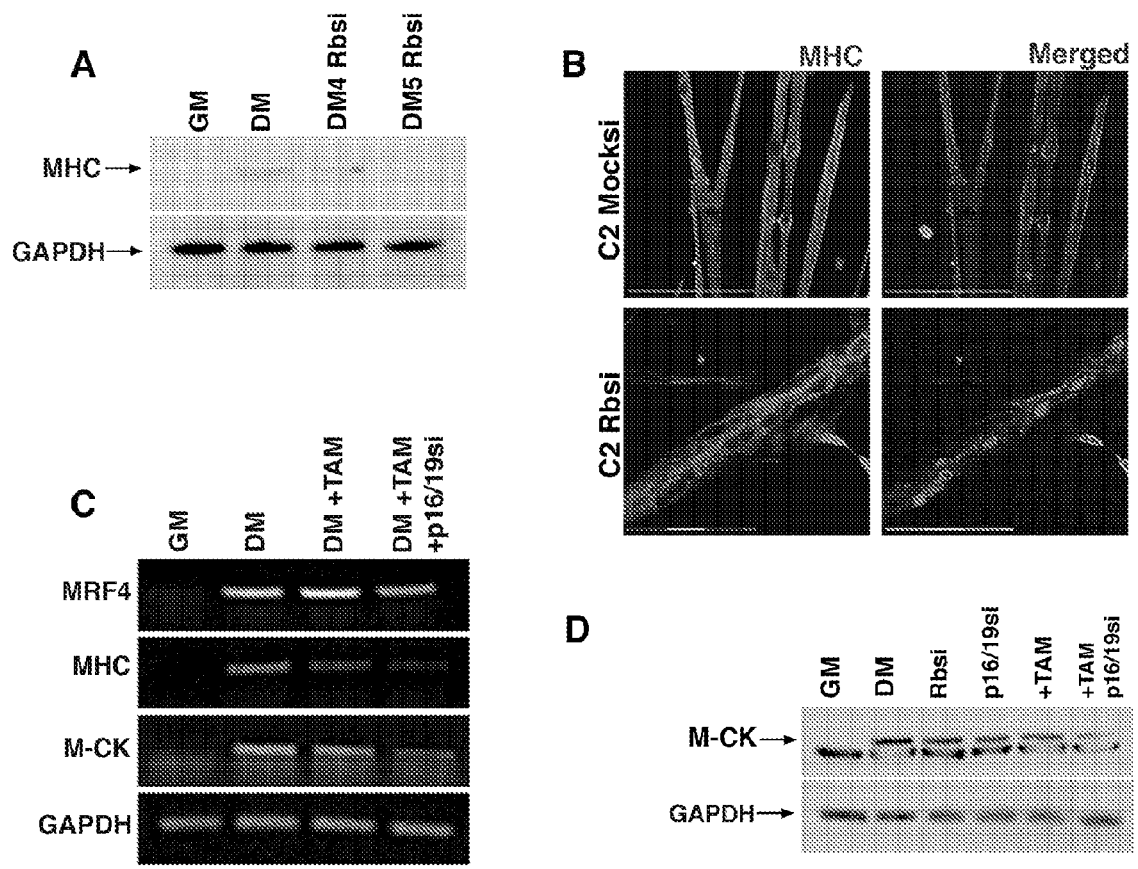
FIG. 15. Myotube dedifferentiation following TAM and p16/19 siRNA treatment. (A) Western analysis of MHC protein (220 kDa) in C2C12 myoblasts (GM) and in myotubes (DM) following treatment with siRNA duplexes against Rb. (B) Immunofluorescence images of DM5 C2C12 myotubes treated with non-specific siRNA duplexes and Rbsi for at least 48 hrs. Myotubes labeled with primary antibodies for MHC (red), BrdU (green), and Hoechst 33258 (blue). Bar, 150 µm. (C) sqRT-PCR analysis of the expression of late differentiation myogenic markers in Growth Medium (GM) or in Differentiation Medium (DM) before and after TAM or TAM and p16/19si treatment. (D) Western blot analysis of M-CK (50 kDa) in primary myoblasts (GM) and DM5 treated as indicated with siRNA duplexes and/or TAM; the 45-kD band seen in the M-CK blot, is likely due to a shared epitope identified by the antibody. In each of the Westerns, GAPDH (35 kDa) is the loading control.
Figure 16:
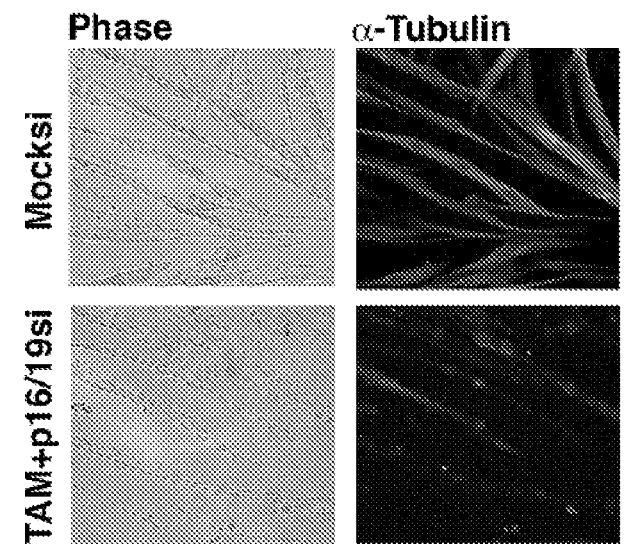
FIG. 16. Alpha-tubulin levels drop after loss of Rb and p16/19. Upper panel: Representative phase and immunofluorescence images of primary myotubes after Mocksi or TAM and p16/19si treatment. Myotubes were labeled with primary antibodies for alpha-tubulin (green) and Hoechst 33258 (blue). Lower panel: Normalized levels of α-Tubulin protein are quantified.
Figure 16:
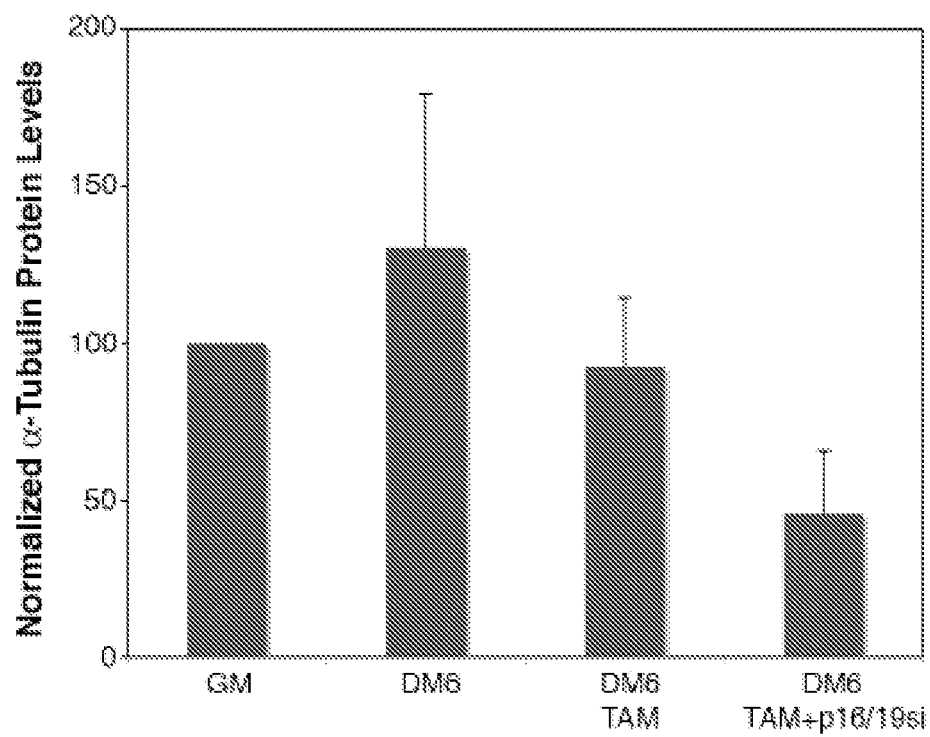

In primary myotubes, protein analysis of cell lysates revealed that some myogenic protein levels are moderately sensitive to the loss of RB alone. A moderate decline in MHC and myogenin levels was observed in primary myotubes following treatment with TAM only (FIG. 4B). However, RBsi treatment caused only a slight drop in myogenin protein levels in primary myotubes (FIG. 4D third lane). Suppression of both RB and p19ARF consistently led to reduced protein levels of all myogenic proteins tested. For example, in the case of alpha tubulin, another protein with specific roles in differentiation of muscle cells, the combined suppression of RB and p16/19 resulted in a marked decrease in protein levels (FIG. 4 F). This occurred in parallel with the increased expression of the mitotic proteins AuroraB and survivin (FIG. 4B). Quantification of MHC levels revealed a marked decrease in expression of this protein after suppression of RB and p19ARF when normalized to levels in control cells in DM for the same period of time (FIG. 4C). These findings, as well as a drop in the expression levels of MRF4, another transcriptional regulator of late differentiation, are supported by semi-quantitative RT-PCR analysis (FIG. 15C).

Morphological deterioration of myotube structure correlated with BrdU$^+$ staining in primary myotubes as in C2C12 myotubes, however, only if both RB and p16/19 were suppressed. FIG. 4D exemplifies the structural collapse of primary myotubes after TAM and p16/19si treatment. While control primary myotubes retained their elongated morphology and nuclear organization, BrdU$^+$ myotubes collapsed into amorphous multinucleated syncytial structures, highlighted by the clustering of myonuclei. While not all of the myonuclei are in S-phase, structural integrity of the myotube has been lost likely due to the lack of maintenance of myotube nuclear protein domains. Myotubes were visualized by time-lapse microscopy after treatment with TAM and Mocksi (Video 1) or TAM and p16/19si. A time-lapse comparison shows that complete morphological collapse of myotube structure only takes place after loss of both the RB as well as Ink4a gene products. Despite extensive structural differences, the RB and ink4a deficient primary myotubes do not die or detach faster than Mocksi-treated myotubes, and retain their motility and membrane activity, such as filopodia and lamellapodia protrusions.

Post-Mitotic Differentiated Myocytes are Capable of Proliferation after Suppression of RB and p16/19.

The extent of muscle differentiation can be characterized based on the serial expression of muscle regulatory transcription factors. MyoD and Myf5 are early and characteristic of cycling myoblasts, whereas late transcription factors include myogenin and MRF4 which are expressed in post-mitotic differentiated myocytes and myotubes. Based on this transcription factor timecourse, we sought to develop a system in which we could study cycling and dedifferentiation in prospectively isolated populations derived from individual differentiated muscle cells. We infected low passage Rosa26-CreER$^{T2}$ RB$^{lox/lox}$ primary myoblasts with a retroviral expression vector in which GFP expression is under the control of the myogenin promoter (pLE-myog3R-GFP). To verify the fidelity of myogenin and GFP co-expression, pLE-myog3R-GFP myoblasts were sparsely seeded in growth medium or differentiation medium for 72 hours and stained for myogenin and GFP. IF analysis clearly showed that GFP and myogenin expression were upregulated in the differentiating (DM3) myocyte population (FIG. 5A). Quantification of IF data indicated that only 0.9% of the cells are GFP-positive in growth conditions, likely representing spontaneous differentiation due to physical contact. In differentiated cultures, GFP expression occurred in 27±2.0% of the cells (FIG. 5Bi). When individual cells were analyzed by microscopy, 98.4% of the cells with detectable GFP also expressed detectable levels of myogenin. High-throughput analysis of GFP expression in myoblasts and myocytes was also performed by fluorescence activated cell sorting (FACS), which showed that 35% of the cell population expressed GFP after 3 days in differentiation medium, while only 1.8% of cells in growth medium were GFP+ (FIG. 5D). Thus pLE-myog3R-GFP infection of primary myoblasts allows for reliable identification of myogenin-expressing populations of cells by means of GFP expression.

Myoblasts seeded at low density will express myogenin and undergo terminal differentiation in the absence of fusion. We took advantage of this in vitro property of muscle cells to investigate whether the dedifferentiation and cell cycle re-entry observed in differentiated multinucleated myotubes could lead to proliferation after suppression of RB and p19ARF in differentiated mononucleated myocytes. The following experiments were performed using individual pLE-myog3R-GFP muscle cells, in order to follow the fate of single cells. First, sparsely seeded primary muscle cells, maintained in DM for 72 hrs, were sorted on the basis of GFP expression as depicted by the gated population in FIG. 5C. To determine whether the differentiated muscle cells were capable of proliferation, the FACS sorted population was cultured in conditioned growth medium (cGM) for up to 48 hrs and then stained (FIG. 5E top panels) for GFP and Ki67, a nuclear marker of cellular proliferation (Scholzen and Gerdes 2000). Only 2.3% of the sorted population had Ki67 positive nuclei. In contrast, cells of the sorted population treated with TAM 24 hrs prior to FACS sorting, and with p16/19si 12 hrs after FACS sorting (FIG. 5E bottom panels) exhibited Ki67 nuclear staining in 25% of the sorted population 48 hrs after culture in cGM (FIG. 5F). Second, as an alternative method to suppress RB and p16/19, siRNA duplexes against RB and p16/19 were used to transiently knockdown expression of both. Analyses to determine the ideal dosage and method of siRNA application showed that most efficient knockdown occurred after tandem treatment of primary muscle cells with RBsi, a 12 hr recovery period, followed by treatment with p16/19si. This double-knockdown (DKD) treatment protocol resulted in comparable results to the TAM and p16/19si treatment, while a combination of siRNA duplexes applied simultaneously was not as efficient in silencing the expression of either gene (FIG. 10E). DKD treatment of FACS sorted GFP cells, resulted in 8.6% Ki67+ nuclei. That the frequency of DNA synthesis was lower in DKD treated cells than in those treated with TAM and p16/19si value was expected given the lower efficiency of a knockdown compared to TAM treatment for RB suppression. The data from these two types of experiments show at the single cell level, that differentiated myogenin-expressing myocytes, like myotubes, efficiently enter S-phase only after suppression of both RB and Ink4a gene expression.

Figure 17:
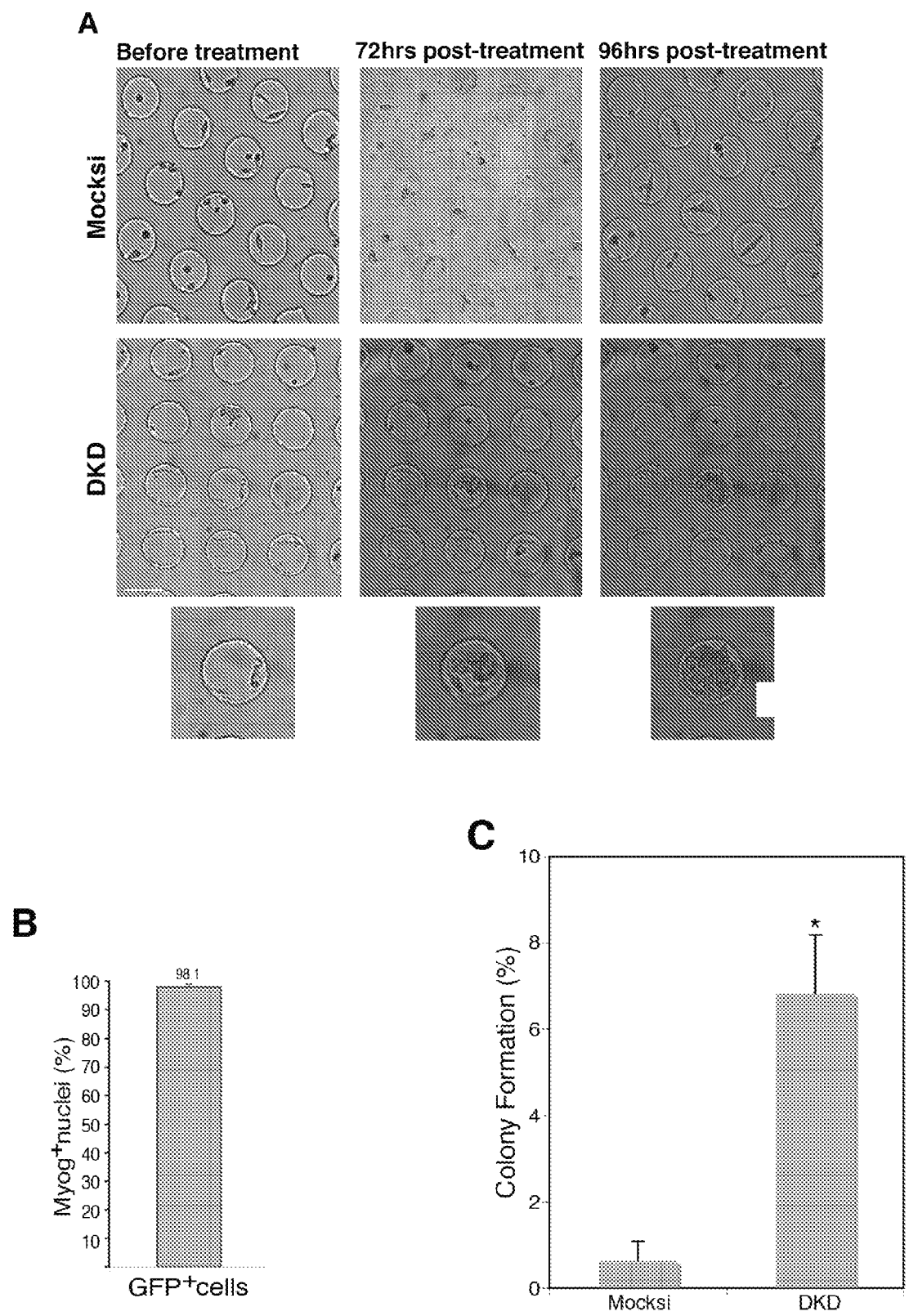
FIG. 17. Myocytes deficient in RB and p16/19 proliferate following FACS isolation. (A) Representative images pLE-myog3R-GFP myocytes FACS sorted directly into microwells, imaged before treatment, as well as 72 and 96 hrs after DKD treatment. Magnified panel, highlights expansion of one well following RBsi and p16/19si treatment. Bar 150 µm. (B) Histogram represents percentage of GFP-positive cells that also express myogenin following FACS isolation of subset of cells sorted into microwells. Individual cells were evaluated for expression of each marker. A minimum of 250 cells were counted from random fields. Error bars indicate the mean±SE of two independent experiments. (C) Histogram represents percent colony formation observed in microwells at 96 hrs after treatment. A minimum of 500 wells with at least one cell before treatment counted for each trial. Error bars indicate the mean±SE of at least three independent experiments. (*P<0.005)

Since mono-nucleated, differentiated myocytes enter S-phase following silencing of RB and p16/19, we assayed whether these cells were capable of completing the cell-cycle and proliferating. We reasoned that if myocytes could divide, they would give rise to clones. However, to rule out cell migration and definitively show that a postmitotic myocyte divided, single-cell resolution and clonal analysis was critical. Accordingly, to assess the proliferative potential of myocytes, we first FACS-purified cells twice in order to isolate individual differentiated GFP+ myocytes which were then sorted directly into microarrays of hydrogel wells. Myocytes were first imaged 12 hrs after sorting into microwells, at which time they were treated with Mocksi or the first application of DKD treatment (FIG. 17A left panels). Images of microwells were captured at 48, 72 and 96 hrs after the completion of DKD treatment. Proliferative myocytes were scored as the percentage of microwells that had a minimum of 8 cells at 96 hrs after treatment. Although overall viability of the cells was impaired due to the toxicity of the slmportter used for RNAi delivery, which could not be adequately removed from the microwells, a clear difference was evident in the percentage of clones generated from myocytes. 6.8% of DKD treated myocytes gave rise to clones whereas only 0.6% of Mocksi treated cells (FIG. 17B). Raw data showed that a total of 109 colonies arose from the DKD treated myocytes, but only 10 colonies arose from the mock treated myocyte population. Taken together these data support the conclusion that myogenin-positive myocytes acquire proliferation potential after suppression of RB and p16/19 expression.

Clonal Expansion and Proliferation of Individually Purified Myocytes after Laser Microdissection and Laser Pressure Catapulting.

We sought to increase the purity of all of our prospectively isolated cells by evaluating each individual myocyte for differentiation prior to capture. FACS sorting in combination with the hydrogel microwell platform described above can be readily used to monitor single-cell proliferation potential. However, several disadvantages precluded subsequent analysis: heterogeneity of the sorted population, disruption of cellular morphology upon detachment from the plate, and lack of post-treatment molecular analysis. These obstacles can be overcome by the use of photoactivated laser microdissection (PALM) and laser pressure catapulting (LPC), which enables pure and homogenous individual cell sample preparation without disruption of cell adhesion and morphology, and permits expansion and molecular analysis after colony establishment. See, for example, Stich, M., et al. (2003) Pathology, research and practice 199(6): 405-409; Schutze, K., et al. (2007) Methods in cell biology 82: 649-673).

Figure 18:
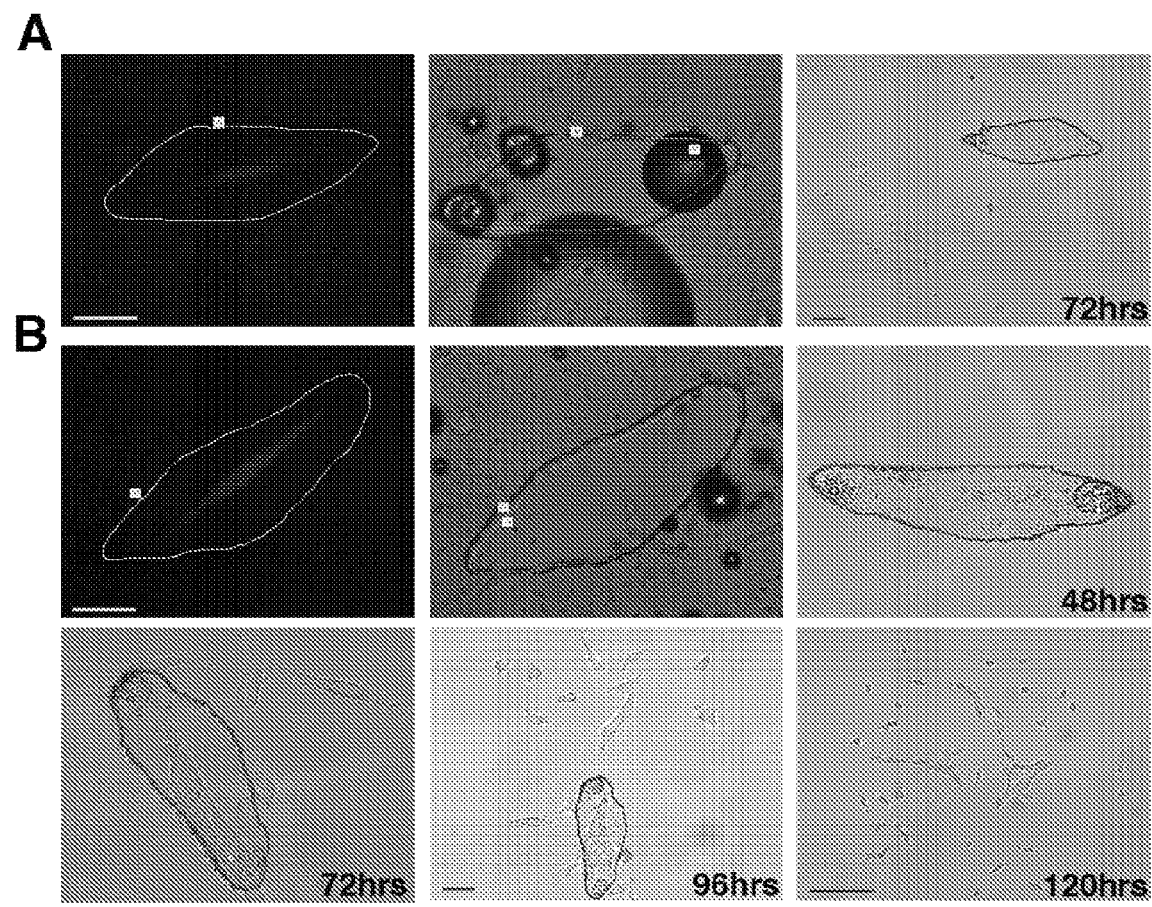
FIG. 18. Single-cell isolation and expansion of dedifferentiated myogenin-GFP myocytes. (A) Representative images of untreated GFP+ myocyte (DM4) prior to microdissection, after LPC, and 72 hrs post-isolation. Bar 50 µm. (B) Representative images of TAM+p16/19si treated GFP+ myocytes, prior to microdissection, after LPC, 48 hrs post-isolation, 72 hrs post-isolation, 96 hrs post-isolation, at which point media was changed, and 120 hrs post-isolation. Bar 50 µm, last panel bar 200 µm.

Laser microdissection and pressure catapulting analysis was performed with myocytes. For this purpose primary myoblasts expressing pLE-myog3R-GFP+ were sparsely seeded and differentiated to become GFP+ myocytes and then treated with either mock siRNA (FIG. 6A) or for suppression of Rb and ARF (FIGS. 5Bi and 5Ci). Individual myocytes were selected based on their differentiated phenotype including elongated morphology evident by phase microscopy (FIG. 6Ai, left) and bright GFP expression (FIGS. 6Bii and 6Cii, left). Laser microdissection was used to mark and cut the membrane surrounding prospectively identified single myocytes (green lines FIG. 6Bii and FIG. 6Cii). Marking and recording membrane shapes allowed for tracking of each membrane and the isolated cell on its surface. The LPC burst locations that lead to catapulting are indicated by the blue dots in the images in FIG. 6Bii, which also serve as a means of identifying the membrane. Typical images obtained during the steps of the PALM and LPC isolation process are shown in FIGS. 6Bii and 6Cii. Myocyte morphology before and after membrane ablation did not significantly change. Note in the example shown that 72 hr after capture, the mocktreated myocyte is still associated with the membrane (FIG. 6Aii, panel 4), and by 96 hr it has left the membrane but still exists as a single adherent cell, although it was cultured in conditioned growth medium since the time of capture (FIG. 6Aii, panel 5). Similarly, in individual myocytes treated for reduction of Rb and ARF, morphology remained intact during the cutting and catapulting (FIGS. 6Bii and 6Cii, left 3 panels). However, in contrast to mock-treated myocytes, reduction of Rb (TAM or siRNA) and ARF (siRNA) led to cell division and colony formation in the immediate vicinity of the membrane (FIG. 6Bii, fourth panel from left, FIG. 6Cii, fourth panel from left). Additional examples of single GFP+ myocyte laser capture are shown in FIG. 18.

Figure 19:
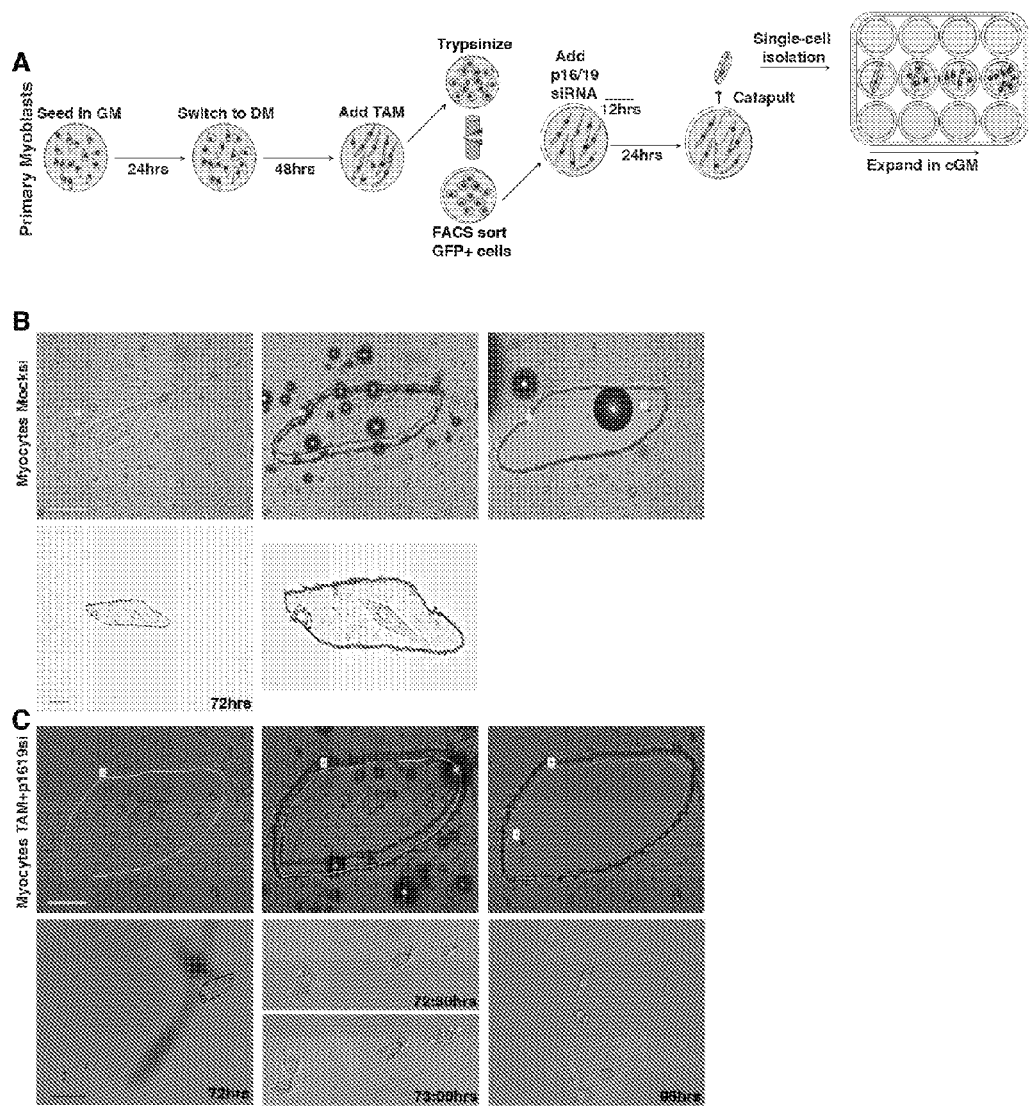
FIG. 19. Single-cell isolation and clonal expansion of FACS sorted myogenin-GFP+ myocytes. (A) Schematic representation of myocyte FACS sorting, treatment and PALM LPC isolation. (B) Representative images of FACS sorted, TAM treated, myocytes (DM4) prior to microdissection, after microdissection, after LPC, and 72 hrs post-isolation. Bar 50 µm. (C) Representative images of FACS sorted myocytes (DM4) treated with TAM+ and 16/19si prior to microdissection, after microdissection, after LPC, and 72 to 73 hrs post-isolation as well as 96 hrs post-isolation. Bar 50 µm, 72 hrs panel bar 200 µm.

In five independent PALM LPC isolation experiments, an analysis of a total of 250 membranes verified that without RB and p16/19 suppression not a single myogenin-GFP+ myocyte captured divided to produce a colony. In contrast, TAM and p16/19si treated myocytes produced 34 colonies, a frequency of 14% colony formation (FIG. 6C). Transient DKD treated myocytes formed colonies at a frequency of 8%, which although lower, corresponds to the frequency of colony formation observed for myocytes obtained by FACS and microwell expansion above (FIG. 13B). One technical problem with live-cell capture by PALM LPC is desiccation of the cells during the LPC phase of cell isolation, which can decrease viability. Finding and documenting the GFP expressing myocytes by microscopy takes time. To overcome this problem, we used FACS to identify and sort myocytes expressing GFP, which were then treated as indicated in the scheme in FIG. 19A. Images of the captured control or TAM and p16/19si treated myocytes are shown which provide further evidence that the control treated myocytes fail to produce colonies in conditioned growth medium (FIG. 19B), while myocytes in which RB and Ink4a genes were silenced (FIG. 19C), exhibited a frequency of 28% colony formation (FIG. 6D). Taken together these results strongly support a role for RB and Ink4a in the maintenance of myogenic differentiation, as their suppression leads to division and expansion of myogenin-expressing differentiated myocytes.

Redifferentiation of Captured Myocyte Colonies after Exposure to Low Serum.

Figure 20:
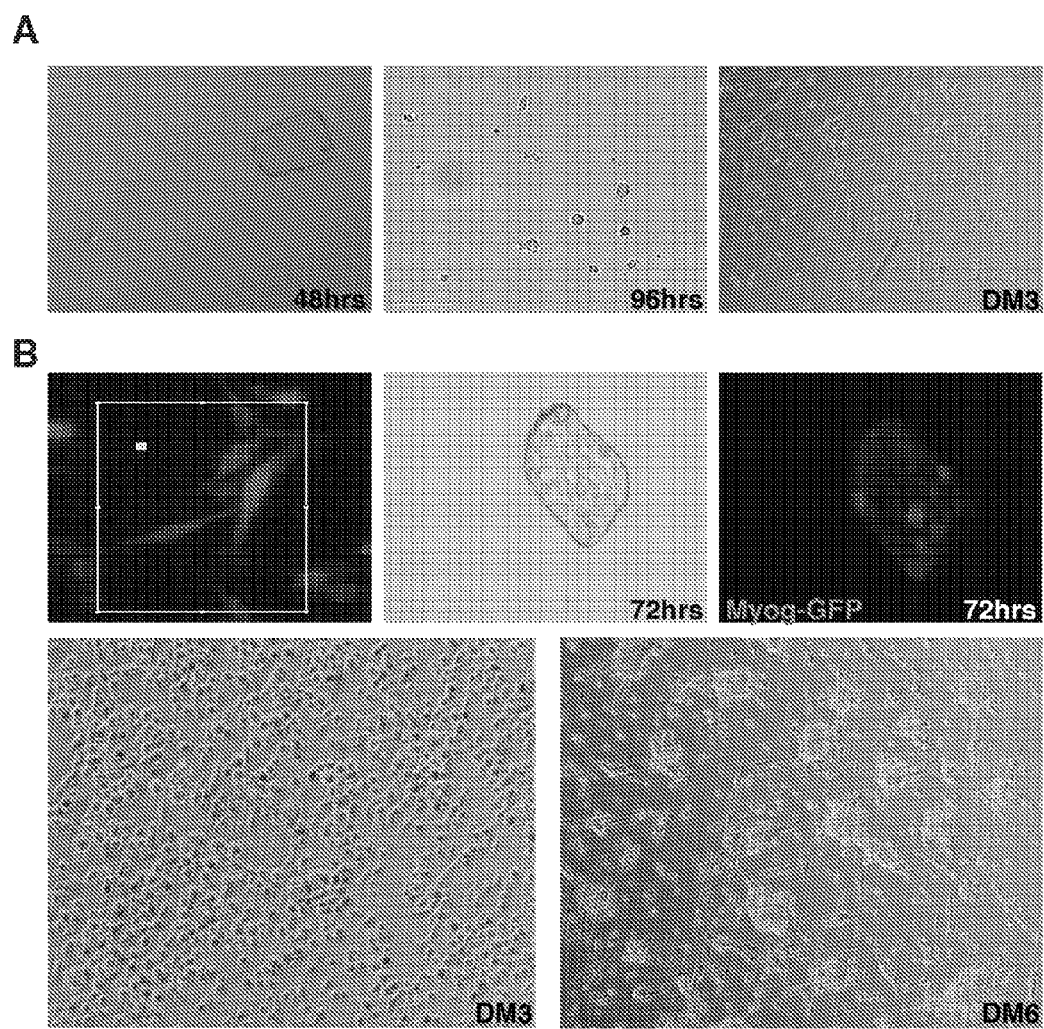
FIG. 20. PALM isolation, expansion and differentiation of primary myoblasts and TAM and p16/19si treated myocytes.

Dedifferentiated muscle cells in axolotls are thought capable of proliferation and contribution to regenerating muscle. To determine if dedifferentiated, actively dividing mammalian myocytes are capable of redifferentiation after expansion, we exposed captured cells to differentiation conditions. After LPC capture, TAM and p16/19si-treated myocytes proliferated rapidly in culture in GM, and most of the cells lost myogenin expression after 72 hrs, evidenced by lack of GFP (FIG. 20B). However, even when exposed to DM for 3 days, these dedifferentiated myocytes continued to proliferate, by comparison with untreated LPC captured myoblasts, which had started to fuse by this time (FIG. 20A). Indeed, the TAM and p16/19si treated population never fused, but instead continued to divide until cellular aggregates were observed by 6 days in differentiation medium (FIG. 20B lower panels). This lack of differentiation is expected because the cells have genetically lost RB expression, which is necessary for differentiation.

In contrast to the TAM-treated captured myocytes, RB suppression in DKD captured myocytes was transient (FIG. 1B). Four colonies derived from single DKD-treated captured myocytes were expanded, split, exposed to DM for four days and then assayed for muscle markers, either by microscopy or biochemically (see scheme in FIG. 6). The DKD colonies spanned the spectrum of differentiation potential, the two extreme ends of which are shown in the top panels of FIG. 7A and FIG. 7C. One colony (DKDcap1) continued to proliferate despite being in DM while another (DKDcap2) differentiated and fused. Heterogeneity in the behavior of captured cells after transient knockdown is expected, as each derived from extensive proliferation.

Figure 7:
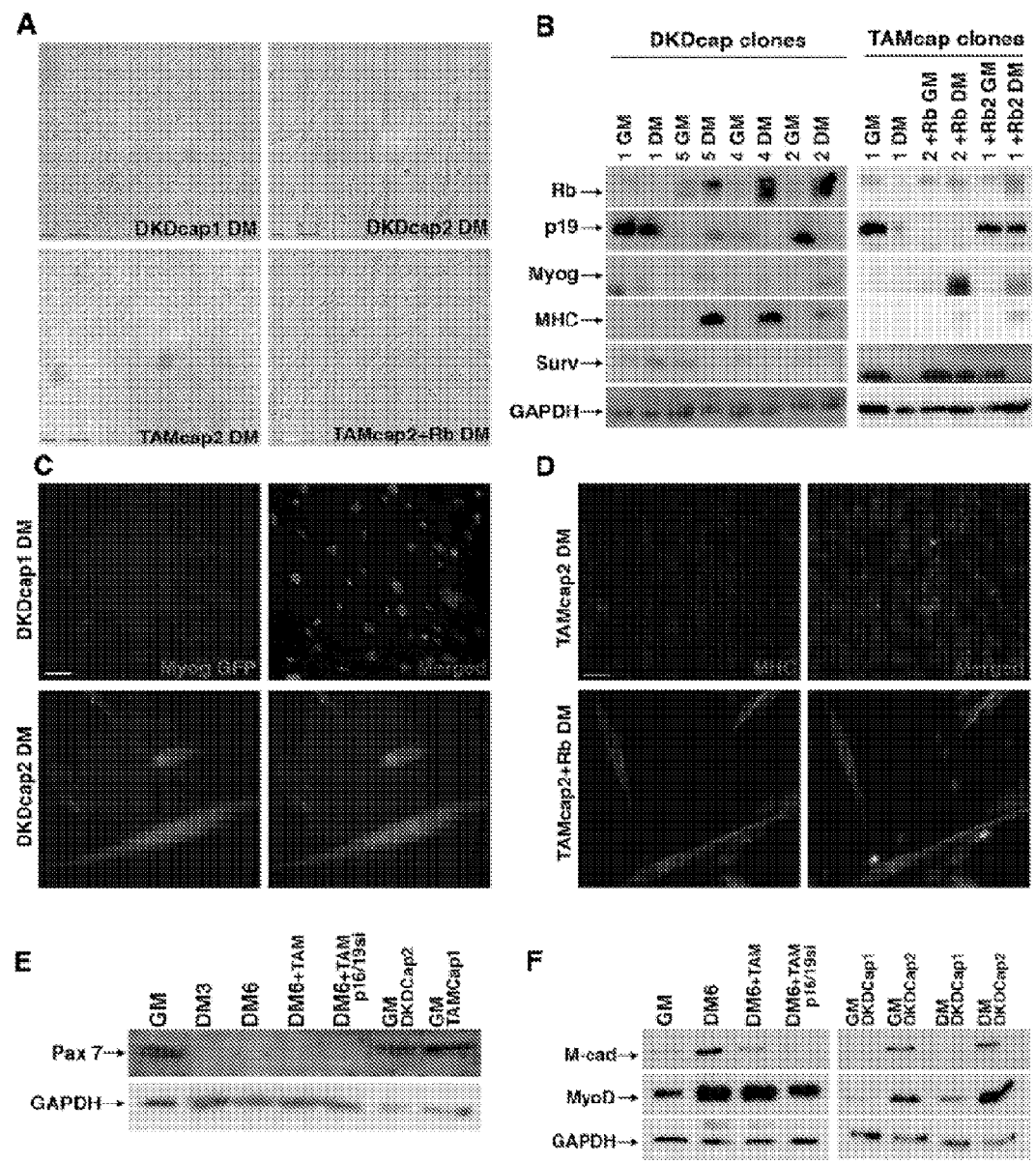
FIG. 7. Dedifferentiated myocytes are capable of expansion and redifferentiation into mature myotubes. (A) Phase contrast images of two DKD captured myocyte colonies and two TAM+p16/19si captured myocyte colonies at DM4, prior to protein harvest for expression analysis. Bar 150 µm (B) Western blot analysis of captured colonies in GM and DM arranged from left to right according to their differentiated morphologies in DM4; protein levels of RB (100 kDa), p19ARF (20 kDa), myogenin (36 kDa), MHC (220 kDa) and Survivin (20 kDa) as well as GAPDH (35 kDa) as a loading control. (C) Representative images of two DKD captured myocyte colonies in DM4, labeled for GFP (green) and myogenin (red) as well as Hoechst 33258 (blue). Bar 25 µm. (D) Representative images of TAMcap2 captured myocyte colony in DM4 labeled for MHC (red) and Hoechst 33358 (blue), a subset of which (lower panels) was infected with retrovirus re-introducing RB expression. Bar 50 µm. (E) Western blot analysis of Pax-7 protein (57 kDa) in muscle cells in GM, DM at indicated time points and with indicated treatments, and in proliferating dedifferentiated clones. (F) Western blot analysis of M-cadherin protein (88 kDa) and MyoD (34 kDa) levels in primary muscle cells under growth conditions (GM), differentiated conditions (DM6) with indicated treatments, and in the isolated dedifferentiated clones (DKDcap1 and DKDcap2) in GM and DM4 (DM).

Protein analysis of the DKD captured colonies supports a function for RB in successful redifferentiation, since DKDcap1 cells have lost RB expression, while the colonies that readily fused and differentiated (DKDcap4 and DKDcap2) expressed high levels of RB in DM (FIG. 7B). p19ARF expression in DKDcap1 was high regardless of media conditions, as expected for highly proliferative cells lacking RB. In contrast, in the colonies that fused to produce large myotubes, the expected downregulation of p19ARF was observed in DM. Expression of myogenin and MHC provided further confirmation of the myogenic potential of the redifferentiated myocytes. Protein levels of myogenin and MHC increased upon exposure of DKDcap4 and DKDcap2 to DM (FIG. 7B), while myogenin and GFP expression, hallmarks of the cells at the time of capture were upregulated only in redifferentiated DKDcap2 myotubes (FIG. 7C). The relative changes in expression patterns of RB, Ink4a and myogenic proteins by the DKDcap2 colony and by captured myoblasts were similar (FIG. 21B).

Figure 8:
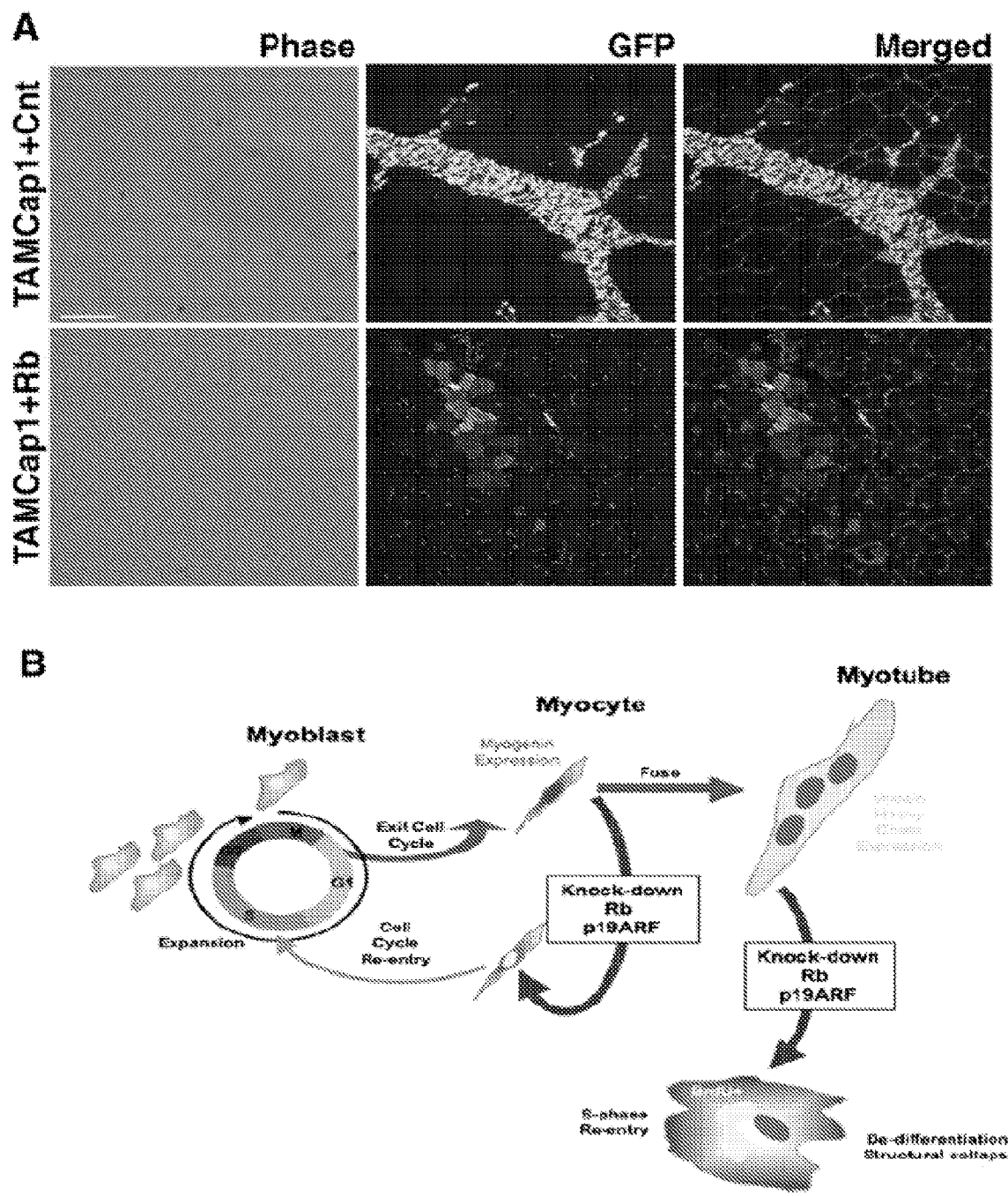
FIG. 8. Dedifferentiated myocytes are capable of fusing to muscle in vivo. (A) Representative cross-sections of tibialis anterior 10 days post-injection of $2.5 \times 10^5$ cells from TAM-cap1 and TAMcap1+RB captured myocytes. Incorporation of dedifferentiated myocytes into pre-existing fibers can be visualized in merged fields by GFP staining (green) of a laminin-bound fibers (red), nuclei (blue); to enhance visualization cells were infected with constitutive-eGFP expressing retroviral vector prior to injection. Bar 50 µm. (B) Schematic representation of the events following suppression of RB and p19ARF in primary differentiated myocytes and multi-nucleated myotubes.

Based on these observations, we reasoned that if RB was re-introduced into the TAM and p16/19si captured cells, redifferentiation and fusion should occur. Thus, we infected a subset of captured colonies with a pMIG retrovirus vector expressing the human RB cDNA. We monitored the TAMcap myoblast colonies after infection with pMIG-RB or control pMIG retrovirus and determined that differentiation and fusion occurred in those colonies that re-expressed RB (FIG. 7A lower panels). Although dedifferentiating myotubes did not reactivate expression of Pax-7 (possibly because of limited duration of viability in culture) isolated dedifferentiated clones did, as evidenced by Western analysis, thus fulfilling this criterion of a proliferating primary myoblast (FIG. 7E). Analysis of RB protein levels harvested in growth and differentiation media from control or pMIG-RB infected TAMcap colonies showed the expected increase in RB protein following pMIG-RB retroviral infection, which occurred in parallel with upregulation of the myogenic proteins, myogenin and MHC (FIG. 7B). While p19ARF levels never acquired the expression pattern observed in the DKDcap colonies, survivin levels decreased in the TAMcap1 colony following pMIG-RB infection (FIG. 7B, lane 6). The myogenic potential of TAMcap colonies infected with pMIG-RB was also verified by IF for MHC (FIG. 7D). Together, these data demonstrate that dedifferentiated myocytes are capable of successful redifferentiation in vitro after capture and expansion, and that this process is dependent upon expression of RB (FIG. 8B).

Captured and Expanded Myocytes are Capable of Contribution to Muscle In Vivo.

Finally, we tested whether PALM LPC isolated, expanded myocytes could contribute to existing muscle in vivo. $1.5 \times 10^5$ DKD derived dedifferentiated myocytes (DKDcap1 and DKDcap2) were injected into the tibialis anterior (TA) of NOD/SCID mice. Myogenin-GFP expression was used to track the injected cells, as this marker was reliably detected in vitro upon differentiation (FIG. 7C). Ten days after injection, DKDcap1 cells, which exhibited no fusion in vitro, proliferated excessively in vivo and caused severe disruption of the muscle laminin network at the site of injection (FIG. 22, top panels). On the other hand, DKDcap2 cells readily fused to the existing muscle fibers and caused no disruption of the laminin network (FIG. 22, bottom panels).

Visualization of the myofibers in which DKDcap2 cells fused was difficult due to weak GFP expression. While in vitro imaging of GFP in redifferentiated myotubes was facilitated by fusion of multiple myogenin-GFP cells, in vivo contribution of a few injected cells to a non-GFP myofiber significantly larger than a culture-derived myotube explains the weak GFP signal observed in vivo. To overcome this problem, we co-infected TAMcap colonies with pMIG-RB and pLE-GFP retrovirus, thus providing these cells with a copy of RB as well as bright constitutive GFP expression. Control TAMcap1 cells, which received control pMIG and pLE-GFP infections, proliferated excessively in vivo (FIG. 8A top panels). By contrast, TAMcap1 cells with re-introduced RB expression, efficiently fused to existing muscle fibers, brightly labeling them with GFP, without any apparent proliferation and without disruption of the existing laminin network (FIG. 8A bottom panels). We conclude that if RB expression is adequately restored dedifferentiated myocytes are capable of redifferentiation and incorporation by fusion to existing muscle in vivo.

DISCUSSION

The molecular basis for the extraordinary disparity between mammals and certain lower vertebrates, such as newts, axolotls and zebrafish, in their capacity to regenerate injured or amputated tissues remains a major unresolved biological question. Mammalian regeneration of a muscle occurs only if that muscle is replaced after mincing or grafting of small muscles, or when chemical agents spare stem cells. Experiments of this type indicate that significant architectural remodeling can occur in lieu of scarring but that the extent of regeneration is limited by the amount of replaced or surviving muscle. Although muscle stem cells can account for some degree of regeneration, they do not seem to suffice. Indeed, to date there is no evidence that the extensive regeneration of entire muscles seen in urodeles can be achieved by any known mammalian mechanism when a significant mass of tissue is removed and not replaced. This limited regenerative potential is in part due to a combination of an excessive demand for cell proliferation at the site of injury in order to replace lost tissue, and an inhibition of architectural remodeling by fibrosis. A possible basis for the failure of regeneration in mammals, which has fascinated scientists for centuries, is a capacity, which newts have retained and mammals have lost: dedifferentiation.

Does dedifferentiation endow urodeles with the regenerative capabilities that mammals lack? This question underscores the need for novel insights into the molecular mechanisms of dedifferentiation in order to discover what is missing in mammals. In urodeles, compelling evidence from studies of skeletal muscle suggests that dedifferentiation is a major mode of tissue regeneration. Dedifferentiation involves two processes, which are separable and independent: muscle cell fragmentation into individual mononuclear cells, and cell cycle re-entry followed by proliferation. In mammalian myotubes produced using the immortalized cell line, C2C12, overexpression of transcriptional factors present in the blastema such as msx1 or twist, or exposure to small molecules that disrupt the cytoskeleton, such as myoseverin, have been reported to result in myotube fragmentation. In the dedifferentiation studies reported here, fragmentation of muscle cells was not observed, which is in good agreement with reports showing that the fragmentation process in newts is independent of cell cycle re-entry (Velloso, C. P., et al. (2000) Differentiation; research in biological diversity 66(4-5): 239-246). In addition, since the trigger and mechanism for muscle fragmentation and cellularization in urodeles remains unknown, it is currently not possible to determine if a similar pathway exists in mammals. Understanding how fragmentation occurs and delineating the dedifferentiation mechanisms are complementary but distinct goals in muscle regeneration biology.

Molecular Regulation of Dedifferentiation by RB and ARF.

Our decision to suppress RB in experiments directed at elucidating the mechanisms underlying muscle dedifferentiation was based on evidence in newts that RB coordinates muscle cell cycle entry in response to damage. In mammals as in newts, cell cycle regulation by RB is dynamic and controlled primarily by its phosphoryation state. There is also a wealth of data firmly establishing the tumor suppressor RB as a necessary player in the orchestration of mammalian muscle cell differentiation, including evidence for a dual role in both muscle cell cycle progression and exit. Indeed, RB null mice die before birth and lack differentiated muscles. Furthermore, RB has also been shown to act not only as a cell cycle regulator, but also to impact differentiation and tissue specific gene expression directly by binding histone deacetylase 1 (HDAC1) and promoting activation of muscle genes such as MyoD. Once differentiation occurs, this state is stably maintained, at least in mammals. This stability is underscored by the inability to reverse differentiation simply by inactivating RB in primary differentiated mammalian muscle cells. Indeed, studies reporting otherwise have been confounded by the use of immortalized cell lines such as C2C12, which we show here do not express the ink4a products. Loss or suppression of RB leads only to moderate dedifferentiation, as demonstrated by the reduced accumulation of myogenin and MHC (FIG. 4). In fact, as shown in this report, it is remarkable how little phenotypic change occurs in primary differentiated skeletal muscle cells when RB is suppressed.

The minimal impact of RB absence alone on muscle dedifferentiation suggested that maintenance of mammalian differentiation is ensured by a separate mechanism. Whereas the RB pathway is intact in lower vertebrates, we reasoned that another component that is absent in regeneration competent vertebrates would be a good candidate regeneration suppressor in mammals. This line of thought led us to focus on the ink4a locus and ARF in particular. Unlike RB, inactivation of ARF alone in knockout mice has no apparent effect on differentiation. In agreement with these reports, we found that ARF alone had no effect on muscle differentiation or dedifferentiation. However, concomitant inactivation of RB and ARF caused extensive dedifferentiation. Differentiated myotubes exhibited robust DNA synthesis and activation of mitotic proteins upon acute loss of RB and p19ARF, suggesting that these proteins are nodal points for intrinsic control of muscle cell cycle reentry. The profound loss of architectural integrity and downregulation of myogenin, MRF-4, MHC and M-CK upon suppression of both RB and p19ARF further suggests that the two together are potent stabilizers of the differentiated state. Notably, alternative approaches that induce cycling by altering growth factor signaling and regeneration in mammalian cardiac muscle cells produce a very moderate effect when compared to regenerating urodele muscle. We speculate that ARF may inhibit robust cycling and regeneration in these settings as well.

Our findings support the hypothesis that tumor suppression mediated by the RB and ink4a loci arose at the expense of regeneration. Both p16ink4a and p19ARF have been recently shown to contribute to the decline in regenerative potential of multiple tissues during aging by affecting stem cell self-renewal. Our study suggests that the ink4a locus has an additional negative impact on tissue regeneration, i.e., suppression of cell cycle re-entry and dedifferentiation. The remarkable combined effect of acute RB and ARF loss strongly suggests (i) that continuous expression of RB itself has an important function in maintaining the differentiated state and (ii) that the maintenance of the differentiated state in mammals depends on complementary activities of RB and ARF. These findings are explicable in view of the known need for continuous regulation of differentiation as well as the documented functions of RB and ARF in preventing inappropriate cycling as tumor suppressors.

Single Cell Analyses of Dedifferentiation.

Bulk cultures do not allow a definitive assessment that a given cell has divided. The cellular complexity and rapid developmental changes observed in the blastema has hindered analysis of dedifferentiation at the single-cell level in urodele regeneration. In mammalian muscle culture systems in which S-phase re-entry was observed, the persistence of cells at earlier stages of differentiation cannot be ruled out; see, for example, Gu, W., et al. (1993) Cell 72(3): 309-324; Schneider, J. W., et al. (1994) Science (New York, N.Y. 264 (5164): 1467-1471; and Blais, A., et al. (2007) The Journal of cell biology 179(7): 1399-1412). In addition, continuous timelapse monitoring and single cell analysis are essential since reports of division of differentiated muscle cells could be the result of cell migration. To overcome these problems we employed (i) dynamic single-cell tracking of myocytes isolated in microwells by time lapse microscopy and (ii) isolation of single myocytes by PALM laser capture microscopy. These single cell studies clearly demonstrated that cell cycle entry and expansion of individual differentiated post-mitotic myocytes occurs after RB and p19ARF loss. We further demonstrated the regenerative potential of dedifferentiated myocytes by inducing redifferentiation. A subset of captured colonies produced by transient inactivation of RB and p19ARF were exposed to differentiation medium in culture and fused to form myotubes. Additionally, in myocytes that had irreversibly lost RB expression due to Cre-mediated excision, reintroduction of RB by retroviral delivery not only induced myotube formation and muscle gene expression in vitro, but also resulted in fusion and regeneration of damaged myofibers in vivo with typical architecture and no evidence of the tumorigenic characteristics of cells that did not receive RB. These findings suggest that transient inactivation of the two tumor suppressors could yield dedifferentiated cells with extensive regenerative potential as depicted in the diagram in FIG. 8B.

We capitalized on evolutionary differences to genetically modify the mammalian cell-cycle regulatory pathways to more closely mimic those found in lower vertebrates. Our results reveal that it is possible to derive regenerative cells from differentiated, post-mitotic muscle in addition to classically defined stem cells. Skeletal muscle cells can alternate between a differentiated, post-mitotic state and a proliferative, regenerative state, retaining the essential characteristics of their cell type of origin during the regenerative cycle. Our experiments implicate ARF in the suppression of regeneration in mammalian cells by impeding dedifferentiation. Thus, a combination of interventions to transiently inactivate the RB pathway in a physiological manner while suppressing ARF may be employed to maximize a mammalian regenerative response.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of producing lineage-restricted mammalian cells (LRCs) from a post-mitotic differentiated mammalian cell (PMD) of the same lineage, comprising:
   contacting a primary culture mammalian myocyte or hepatocyte PMD with an effective amount of a combination of agents comprising a first agent that transiently inhibits the activity of a pocket protein and an effective amount of a second agent that transiently inhibits the activity of the cyclin-dependent kinase inhibitor 2A alternate reading frame protein (ARF), under conditions sufficient to permit the PMD to transiently divide to produce progeny, wherein said progeny are LRCs of the same lineage as the PMD.

2. The method of claim 1, wherein said PMD dedifferentiates prior to dividing.

3. The method of claim 1, wherein said PMD is a myocyte.

4. The method of claim 3, wherein said myocyte is selected from the group consisting of a cardiomyocyte, a smooth muscle myocyte, a skeletal myocyte, and myofiber.

5. The method of claim 1, wherein said pocket protein is retinoblastoma protein (RB).

6. The method of claim 5, wherein said agent that transiently inhibits RB activity is a nucleic acid effective to transiently inhibit said activity, a polypeptide effective to transiently inhibit said activity, or a small molecule effective to transiently inhibit said activity.

7. The method of claim 1, wherein said agent that transiently inhibits ARF activity is a nucleic acid effective to transiently inhibit said activity, a polypeptide effective to transiently inhibit said activity, or a small molecule effective to transiently inhibit said activity.

8. The method of claim 1, wherein about 10% of PMDs of a population that are contacted are induced to transiently divide.

9. The method of claim 1, wherein the PMD are from a human individual with a disease.

10. The method of claim 9, wherein the individual is alive.

11. The method of claim 9, wherein the individual is a cadaver.

12. The method of claim 1, wherein said method further comprises transferring said progeny LRCs to conditions that promote differentiation, wherein the population that is produced is a population of PMDs of the same lineage as the PMD that was contacted in said contacting step.

13. The method of claim 12, wherein said transferring is effected by transplanting said progeny into a subject.

14. The method of claim 13, wherein said subject is in need of tissue regeneration therapy.

15. The method of claim 1, wherein the PMD is a hepatocyte.

* * * * *